United States Patent
Lee et al.

(10) Patent No.: US 11,219,413 B2
(45) Date of Patent: Jan. 11, 2022

(54) SYSTEMS AND METHODS FOR SECURING A CONTINUOUS ANALYTE SENSOR TO A HOST

(71) Applicant: DexCom, Inc., San Diego, CA (US)

(72) Inventors: James Jinwoo Lee, San Diego, CA (US); Leif N. Bowman, Livermore, CA (US); Tim Ray Gackstetter, San Diego, CA (US); Jonathan Hughes, Carlsbad, CA (US); Jeff Jackson, Poway, CA (US); Ted Tang Lee, San Diego, CA (US); Phong Lieu, San Diego, CA (US); Andrew Attila Pal, San Diego, CA (US); James R. Petisce, Westford, MA (US); Jack Pryor, Ladera Ranch, CA (US); Roger Schneider, Encinitas, CA (US); Peter C. Simpson, Cardiff, CA (US); George Vigil, San Diego, CA (US); Matthew D. Wightlin, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 351 days.

(21) Appl. No.: 14/835,603

(22) Filed: Aug. 25, 2015

(65) Prior Publication Data

US 2016/0058380 A1 Mar. 3, 2016

Related U.S. Application Data

(60) Provisional application No. 62/042,170, filed on Aug. 26, 2014.

(51) Int. Cl.
*A61B 5/00* (2006.01)
*A61B 5/145* (2006.01)

(52) U.S. Cl.
CPC .......... *A61B 5/68335* (2017.08); *A61B 5/145* (2013.01); *A61B 5/14532* (2013.01); *A61B 5/6832* (2013.01); *A61B 5/6849* (2013.01); *A61B 2560/0412* (2013.01); *A61B 2562/164* (2013.01)

(58) Field of Classification Search
CPC ................................................. A61B 2562/164
See application file for complete search history.

(56) References Cited

U.S. PATENT DOCUMENTS

| | | | |
|---|---|---|---|
| 6,952,605 B1 * | 10/2005 | Scarberry | A61B 5/0408 600/372 |
| 8,641,618 B2 | 2/2014 | Jennewine et al. | |
| 2003/0050593 A1 * | 3/2003 | Diermann | A61B 5/150503 604/44 |
| 2005/0245839 A1 * | 11/2005 | Stivoric | A61B 5/0008 600/549 |

(Continued)

FOREIGN PATENT DOCUMENTS

WO    WO 2013066401 A1 *  5/2013  ............. A61L 15/42

*Primary Examiner* — Michael R Bloch
(74) *Attorney, Agent, or Firm* — Knobbe Martens Olson & Bear LLP

(57) ABSTRACT

Adhesive pad systems that provide longer lasting adherence of the mounting unit to the host's skin are provided. Some systems include a reinforcing overlay that at least partially covers the adhesive pad. The reinforcing overlay may be removable without disturbing the sensor so that the overlay may be replaceable.

13 Claims, 48 Drawing Sheets

(56) References Cited

U.S. PATENT DOCUMENTS

| | | | |
|---|---|---|---|
| 2006/0020192 A1* | 1/2006 | Brister | A61B 5/0002 600/345 |
| 2007/0123763 A1* | 5/2007 | Al-Ali | A61B 5/14552 600/344 |
| 2007/0219597 A1* | 9/2007 | Kamen | G05D 7/0647 607/60 |
| 2008/0249383 A1* | 10/2008 | Sass | A61B 5/14532 600/345 |
| 2009/0048563 A1* | 2/2009 | Ethelfeld | A61M 5/158 604/174 |
| 2010/0081913 A1* | 4/2010 | Cross | A61B 5/04085 600/386 |
| 2013/0030259 A1* | 1/2013 | Thomsen | A61B 5/02028 600/301 |
| 2013/0267811 A1* | 10/2013 | Pryor | A61B 5/6833 600/365 |
| 2014/0025010 A1* | 1/2014 | Stroup | A61M 25/02 604/179 |
| 2014/0039292 A1* | 2/2014 | Su | A61B 5/0408 600/391 |

* cited by examiner

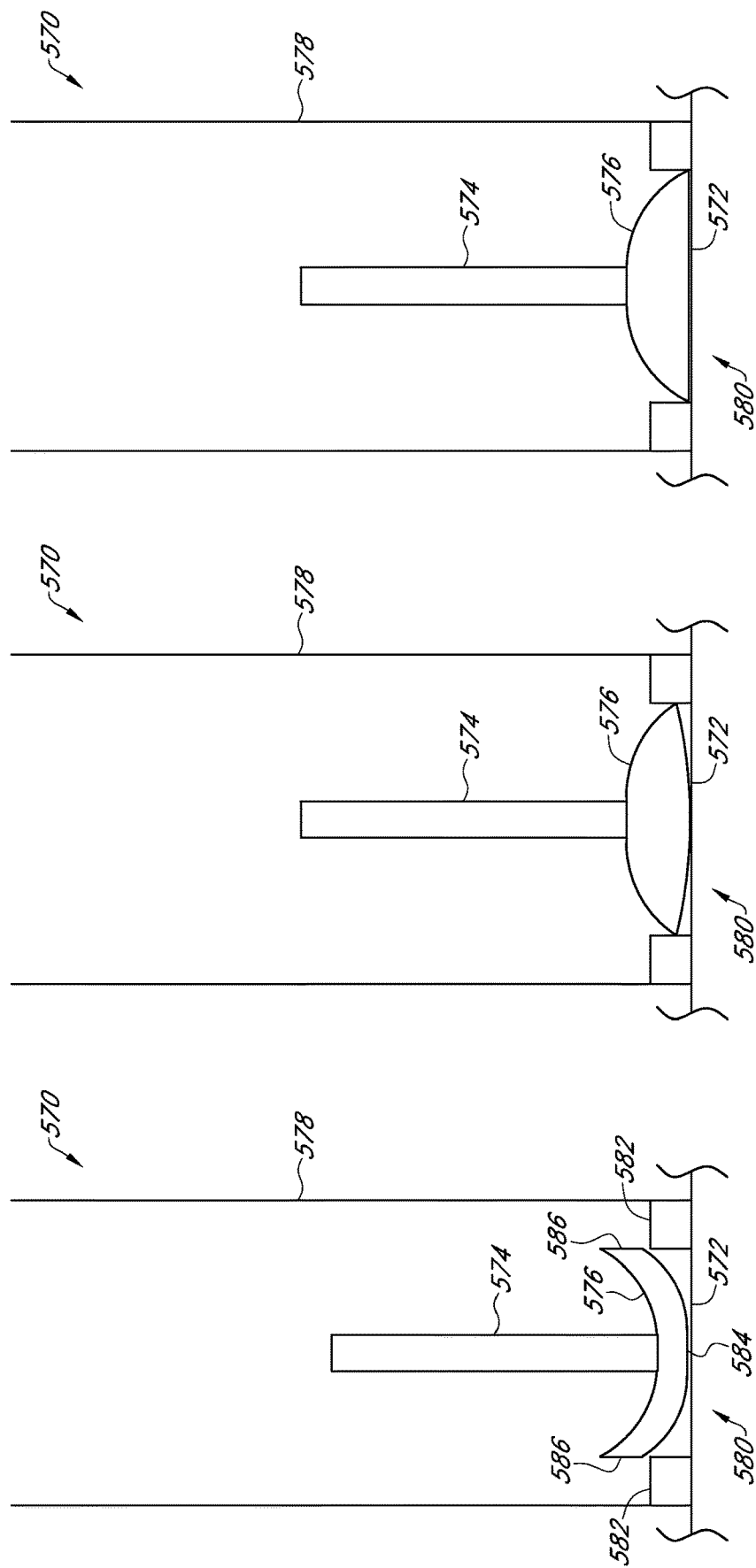

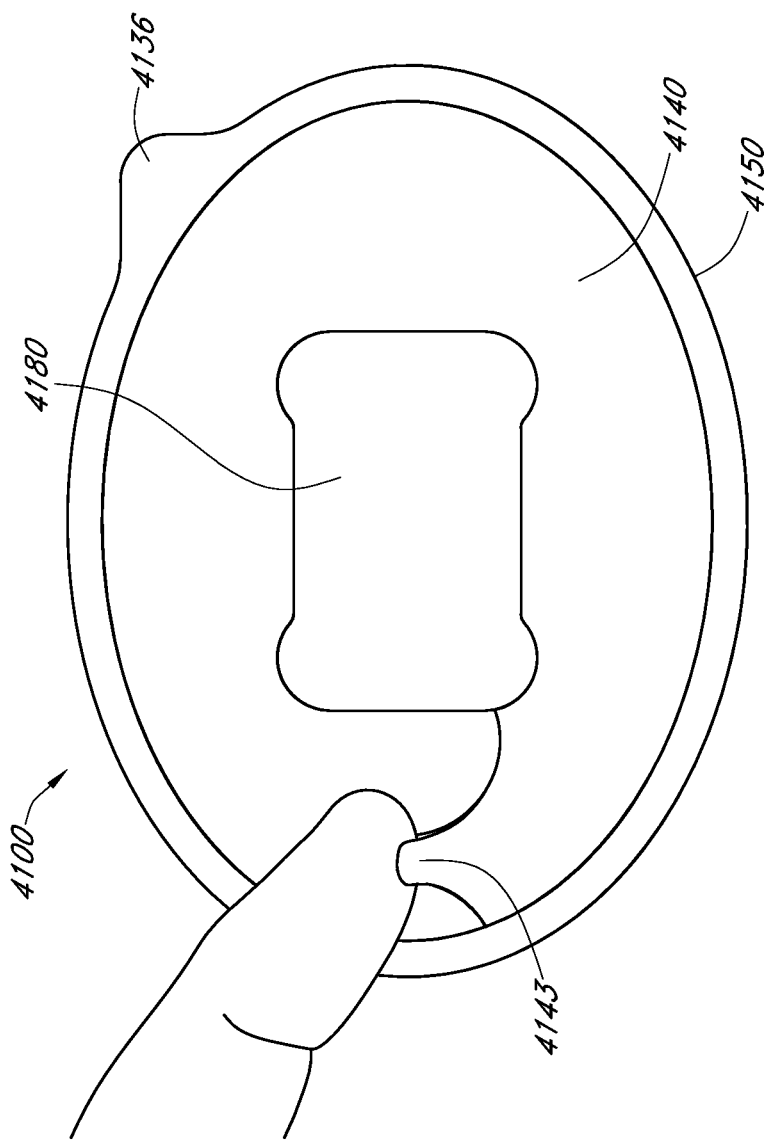
FIG. 41C1

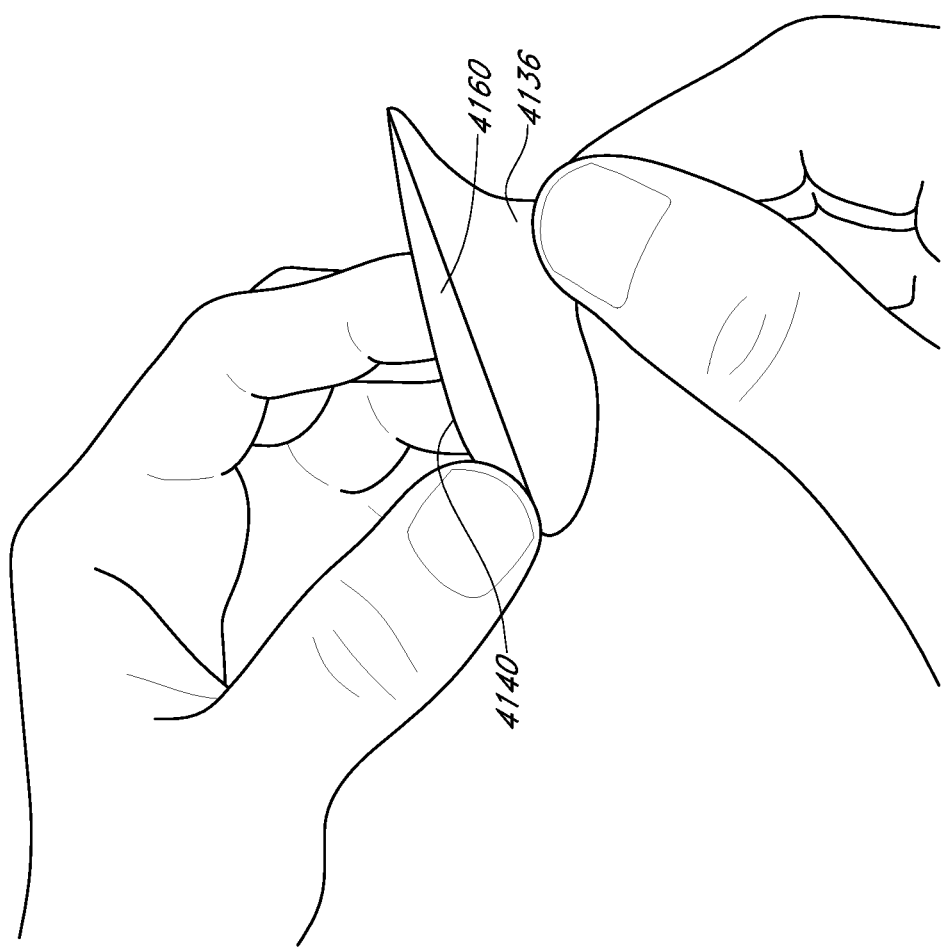
FIG. 41C2

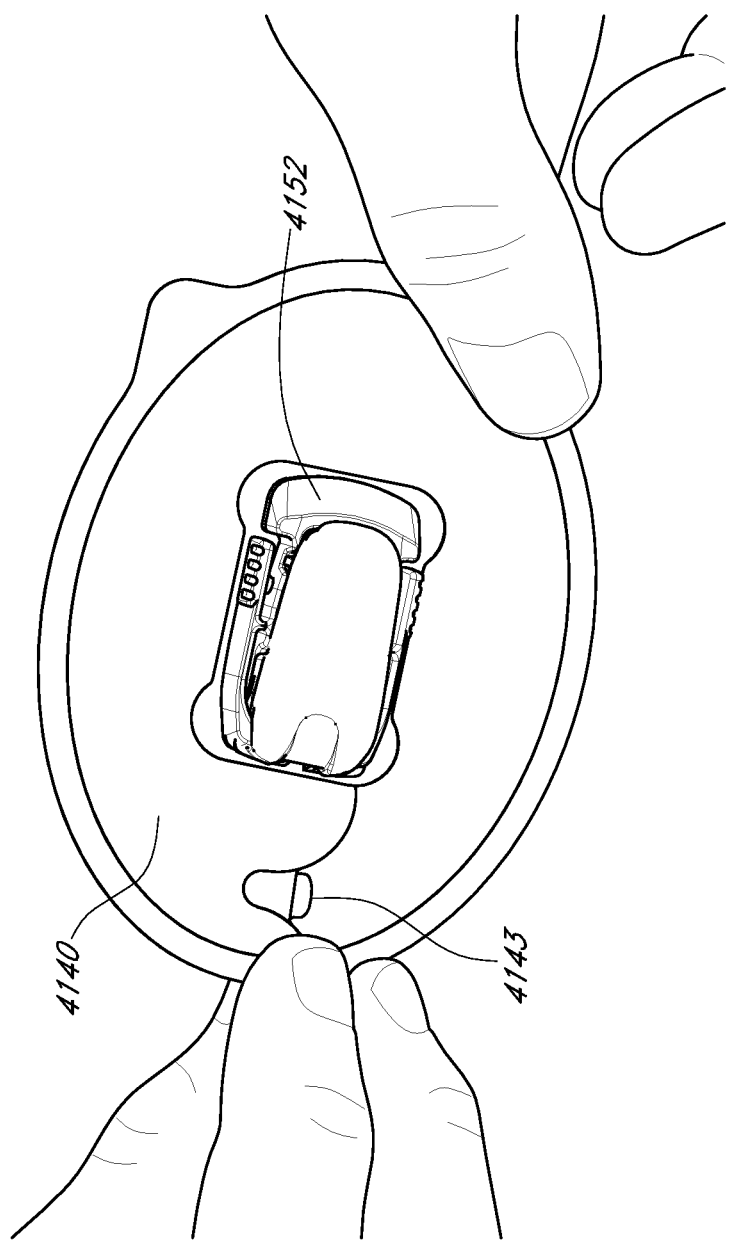
FIG. 41C3

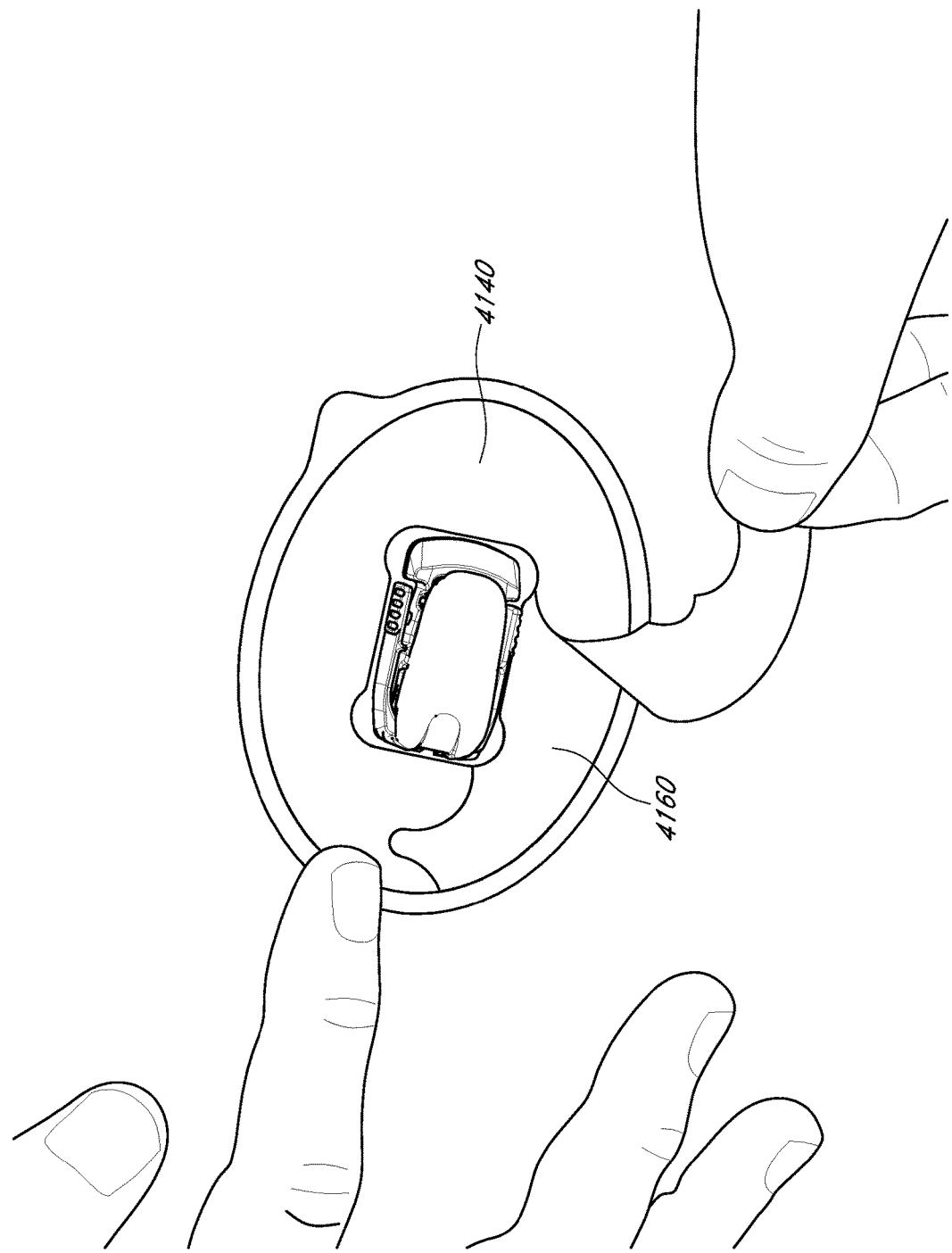
FIG. 41C4

SYSTEMS AND METHODS FOR SECURING A CONTINUOUS ANALYTE SENSOR TO A HOST

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of priority under 35 U.S.C. § 119(e) of U.S. Provisional Application No. 62/042,170 filed Aug. 26, 2014. The aforementioned application is incorporated by reference herein in its entirety, and is hereby expressly made a part of this specification.

TECHNICAL FIELD

The present embodiments relate to systems and methods for measuring an analyte concentration in a host.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements associated with the deterioration of small blood vessels, for example, kidney failure, skin ulcers, or bleeding into the vitreous of the eye. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements may be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

SUMMARY

The various embodiments of the present systems and methods for securing a continuous analyte sensor to a host have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the realization that current adhesive pads may not remain adhered to the host's skin for a desired duration. For example, when a user begins a new sensor session, it is desirable for that sensor to remain within the host for up to about seven days. In the future, the target sensor session length may be even longer, such as up to about fourteen days. Therefore, there is a need for an adhesive pad system that provides longer lasting adherence of the mounting unit to the host's skin. In some embodiments, the adherence desirably persists for about ten days to about fourteen days.

In a first aspect, an adhesive pad system is provided for securing a continuous analyte sensor assembly to skin of a host, the system comprising: a housing configured to receive a sensor electronics unit; an adhesive pad having an upper surface and an undersurface, wherein the housing is secured to the upper surface of the adhesive pad, and wherein the undersurface of the adhesive pad includes an adhesive material configured to adhere the adhesive pad to the skin of the host; and a reinforcing overlay having an upper surface, an undersurface, and a central opening configured to allow at least a portion of the housing to protrude therefrom, wherein the undersurface of the overlay includes an adhesive material configured to adhere the overlay to the adhesive pad and to the skin of the host, wherein the overlay has a larger perimeter dimension than the adhesive pad, such that the overlay extends outwardly on all sides from a periphery of the adhesive pad when the overlay is positioned over the adhesive pad with the housing protruding through the central opening, and wherein a first portion of the overlay adheres to the adhesive pad and a second portion of the overlay adheres to the skin of the host.

In an embodiment of the first aspect, the first portion of the overlay comprises from about 10% to about 65% of a total area of the overlay.

In an embodiment of the first aspect, the first portion of the overlay comprises from about 20% to about 55% of the total area of the overlay.

In an embodiment of the first aspect, the adhesive pad has an area from about 1 square inch to about 2 square inches.

In an embodiment of the first aspect, the overlay has an area from about 4 square inches to about 7 square inches.

In an embodiment of the first aspect, the ultimate adhesive strength of the adhesive pad system immediately after application to a test surface is great than about 12 lbf.

In an embodiment of the first aspect, the test surface is stainless steel.

In an embodiment of the first aspect, application of the overlay onto the adhesive pad results in an increased adhesive strength that is from about 40% to about 45% of the adhesive strength of the adhesive pad alone.

In an embodiment of the first aspect, the overlay is configured to be removed from the adhesive pad and from the skin of the host without disturbing continued operation of the sensor electronics unit.

In a second aspect, a method is provided for securing a continuous analyte sensor assembly to skin of a host, the method comprising: securing the continuous analyte sensor assembly to the skin of the host, wherein the continuous analyte sensor assembly comprises a continuous analyte sensor, an adhesive pad, and a housing configured to receive a sensor electronics unit, wherein the adhesive pad comprises an upper surface and an undersurface, wherein the housing is secured to the upper surface of the adhesive pad, and wherein the undersurface of the adhesive pad includes an adhesive material configured to adhere the adhesive pad to the skin of the host; and applying a reinforcing overlay to the adhesive pad and to the skin, wherein the overlay comprises a top surface and a bottom surface, wherein the overlay includes an upper surface, an undersurface, and a central opening configured to allow at least a portion of the housing to protrude therefrom, wherein the undersurface of the overlay includes an adhesive material configured to adhere the overlay to the adhesive pad and to the skin of the host, wherein the overlay has a larger perimeter dimension than the adhesive pad, such that the overlay extends outwardly on all sides from a periphery of the adhesive pad when the overlay is positioned over the adhesive pad with the housing protruding through the central opening, and wherein a first portion of the overlay adheres to the adhesive pad and a second portion of the overlay adheres to the skin of the host.

In an embodiment of the second aspect, the first portion of the overlay comprises from about 10% to about 65% of a total area of the overlay.

In an embodiment of the second aspect, the first portion of the overlay comprises from about 20% to about 55% of a total area of the overlay.

In an embodiment of the second aspect, the adhesive pad has an area from about 1 square inch to about 2 square inches.

In an embodiment of the second aspect, the overlay has an area from about 4 square inches to about 7 square inches.

In a third aspect, an adhesive pad system is provided for securing a continuous analyte sensor assembly to skin of a host, the system comprising: a housing configured to receive a sensor electronics unit; a frame configured to receive the housing, the frame including a lip that is sized and shaped to receive the housing with the lip extending around the outer edges of the housing, and a flange extending radially outward from a lower end of the lip; and a reinforcing overlay having an upper surface, an undersurface, and a central opening configured to allow at least a portion of the housing and at least a portion of the frame to protrude therefrom, wherein the undersurface of the overlay includes an adhesive material configured to adhere the overlay to the flange and to the skin of the host, wherein the overlay has a larger perimeter dimension than the flange, such that the overlay extends outwardly on all sides from a periphery of the flange when the overlay is positioned over the frame, and wherein a first portion of the overlay adheres to the flange and a second portion of the overlay adheres to the skin of the host.

In an embodiment of the third aspect, the housing comprises a planar bottom wall and a lip that extends around a periphery of the bottom wall.

In an embodiment of the third aspect, the bottom wall includes an opening to accommodate a sensor of the sensor assembly.

In an embodiment of the third aspect, the flange of the frame includes texturing that provides improved breathability.

In a fourth aspect, an adhesive pad system is provided for securing a continuous analyte sensor assembly to skin of a host, the system comprising: a housing configured to receive a sensor electronics unit; an adhesive layer configured to adhere to the host's skin, the adhesive layer having an upper surface and an undersurface, wherein the undersurface of the adhesive layer includes an adhesive material configured to adhere the adhesive layer to the skin of the host; and a cushioning layer configured to adhere to the adhesive layer, the cushioning layer having an upper surface and an undersurface, wherein the undersurface of the cushioning layer includes an adhesive material configured to adhere the cushioning layer to the upper surface of the adhesive layer, the cushioning layer further having a first thickness.

In an embodiment of the fourth aspect, the adhesive layer has a second thickness that is less than the first thickness, and the adhesive layer has a larger perimeter dimension than the cushioning layer, such that the adhesive layer extends outwardly on all sides from a periphery of the cushioning layer when the cushioning layer is positioned over the adhesive layer.

In an embodiment of the fourth aspect, the adhesive pad system comprises a layer of double-sided tape configured to be interposed between the adhesive layer and the sensor electronics unit housing.

In an embodiment of the fourth aspect, the double-sided tape has a smaller perimeter dimension than both the overlay and the cushioning layer.

In an embodiment of the fourth aspect, the upper surface of the cushioning layer abuts and adheres to a bottom surface of the electronics unit housing.

In an embodiment of the fourth aspect, the housing comprises a planar bottom wall and a lip that extends around a periphery of the bottom wall.

In an embodiment of the fourth aspect, the bottom wall includes an opening to accommodate a sensor of the sensor assembly.

In an embodiment of the fourth aspect, the cushioning layer, and the adhesive layer, each include at least one opening, and the openings in the cushioning layer and the adhesive layer align with one another and with the opening in the bottom wall of the housing.

In a fifth aspect, an adhesive pad system is provided for securing a continuous analyte sensor assembly to skin of a host, the system comprising: a housing configured to receive a sensor electronics unit; an adhesive pad having an upper surface and an undersurface, wherein the housing is secured to the upper surface of the adhesive pad, and wherein the undersurface of the adhesive pad includes an adhesive material configured to adhere the adhesive pad to the skin of the host; and a reinforcing overlay configured to cover the adhesive pad, the overlay having an upper surface, an undersurface, and a central opening configured to allow at least a portion of the housing to protrude therefrom, wherein the undersurface of the overlay includes an adhesive material configured to adhere the overlay to the adhesive pad and to the skin of the host, the overlay further having a larger perimeter dimension than the adhesive pad, such that the overlay extends outwardly on all sides from a periphery of the adhesive pad when the overlay is positioned over the adhesive pad, wherein the overlay includes perforations that mark a boundary between a first radially outward portion and a second inner portion.

In an embodiment of the fifth aspect, the perforations facilitate removal of the first radially outward portion from the adhesive pad system without disturbing the adhesive pad.

In an embodiment of the fifth aspect, a path traced by the perforations is substantially the same size and shape as the periphery of the adhesive pad.

In a sixth aspect, a method is provided for securing a continuous analyte sensor assembly to skin of a host, the method comprising: securing the continuous analyte sensor assembly to the skin of the host, wherein the continuous analyte sensor assembly comprises a continuous analyte sensor, an adhesive pad, and a housing configured to receive a sensor electronics unit, wherein the adhesive pad comprises an upper surface and an undersurface, wherein the housing is secured to the upper surface of the adhesive pad, and wherein the undersurface of the adhesive pad includes an adhesive material configured to adhere the adhesive pad to the skin of the host; applying a reinforcing overlay to the adhesive pad and to the skin, wherein the overlay includes an upper surface, an undersurface, and a central opening configured to allow at least a portion of the housing to protrude therefrom, wherein the undersurface of the overlay includes an adhesive material configured to adhere the overlay to the adhesive pad and to the skin of the host, wherein the overlay has a larger perimeter dimension than the adhesive pad, such that the overlay extends outwardly on all sides from a periphery of the adhesive pad when the overlay is positioned over the adhesive pad with the housing protruding through the central opening, and wherein the overlay includes perforations that mark a boundary between a first radially outward portion and a second inner portion; and removing the first radially outward portion of the overlay without removing the second inner portion by tearing the overlay along the perforations.

In an embodiment of the sixth aspect, the overlay comprises a first overlay, the method further comprising applying a second reinforcing overlay over the second inner portion of the first overlay and to the skin of the host.

In an embodiment of the sixth aspect, the second overlay includes an upper surface, an undersurface, and a central opening configured to allow at least a portion of the housing to protrude therefrom, wherein the undersurface of the second overlay includes an adhesive material configured to adhere the second overlay to the second inner portion of the first overlay and to the skin of the host.

In an embodiment of the sixth aspect, the second overlay includes perforations that mark a boundary between a first radially outward portion and a second inner portion.

In a seventh aspect, an adhesive pad system is provided for securing a continuous analyte sensor assembly to skin of a host, the system comprising: a housing configured to receive a sensor electronics unit; and an adhesive pad having an upper surface, wherein the housing is secured to the upper surface of the adhesive pad, and wherein the adhesive pad includes a plurality of layers, and each of the layers includes an undersurface having an adhesive material configured to adhere the adhesive pad to the skin of the host, and wherein the adhesive material on each of the layers has a different strength.

In an embodiment of the seventh aspect, the adhesive pad comprises an innermost layer, an outermost layer, and an intermediate layer.

In an embodiment of the seventh aspect, the innermost layer has a weakest adhesive material, the outermost layer has a strongest adhesive material, and the intermediate layer has an adhesive material with a strength between the weakest adhesive material and the strongest adhesive material.

In an embodiment of the seventh aspect, the innermost layer has a strongest adhesive material, the outermost layer has a weakest adhesive material, and the intermediate layer has an adhesive material with a strength between the weakest adhesive material and the strongest adhesive material.

In an embodiment of the seventh aspect, each of the layers is covered with a removable backing.

In an embodiment of the seventh aspect, each of the removable backings includes a pull-tab at its periphery.

In an eight aspect, a method is provided for securing a continuous analyte sensor assembly onto skin of a host, the method comprising: receiving the continuous analyte sensor assembly, wherein the continuous analyte sensor assembly comprises a housing configured to receive a sensor electronics unit; and an adhesive pad having an upper surface, wherein the housing is secured to the upper surface of the adhesive pad, and wherein the adhesive pad includes a plurality of layers, and each of the layers includes an undersurface having an adhesive material configured to adhere the adhesive pad to the skin of the host, wherein the adhesive material on each of the layers has a different strength, and wherein each of the layers is covered with a removable backing; wherein the method comprises peeling off a first one of the removable backings and adhering the adhesive pad to the host's skin without peeling off a second one of the removable backings.

In an embodiment of the eighth aspect, the adhesive pad comprises an innermost layer, an outermost layer, and an intermediate layer.

In an embodiment of the eighth aspect, the innermost layer has a weakest adhesive material, the outermost layer has a strongest adhesive material, and the intermediate layer has an adhesive material with a strength between the weakest adhesive material and the strongest adhesive material.

In an embodiment of the eighth aspect, the innermost layer has a strongest adhesive material, the outermost layer has a weakest adhesive material, and the intermediate layer has an adhesive material with a strength between the weakest adhesive material and the strongest adhesive material.

In a ninth aspect, a continuous analyte sensor system is provided, the system comprising: a continuous analyte sensor; a mounting unit configured to be placed on skin of a host, the mounting unit including an adhesive pad and a housing secured to an upper surface of the adhesive pad, wherein the adhesive pad includes an undersurface having an adhesive material configured to adhere to the host's skin; and an inserter configured to insert the continuous analyte sensor into the host, wherein the continuous analyte sensor is disposed within the inserter prior to sensor insertion, and wherein the inserter is configured to be secured to the housing of the mounting unit during sensor insertion; wherein the mounting unit is adapted to undergo a different sterilization process than the inserter and/or the continuous analyte sensor.

In a tenth aspect, a method is provided for inserting a continuous analyte sensor into a host, the method comprising: applying a mounting unit onto skin, wherein the mounting unit comprises an adhesive pad and a housing secured to an upper surface of the adhesive pad, wherein the adhesive pad includes an undersurface having an adhesive material configured to adhere to the host's skin; securing an inserter to the housing of the mounting unit, wherein the continuous analyte sensor is disposed within the inserter prior to sensor insertion, and wherein the mounting unit is not sterilized prior to sensor insertion; and activating the inserter to insert the continuous analyte sensor into the host.

In an eleventh aspect, an adhesive pad system is provided for securing a continuous analyte sensor assembly to skin of a host, the system comprising: a housing configured to receive a sensor electronics unit; an adhesive pad having an upper surface and an undersurface, wherein the housing is secured to the upper surface of the adhesive pad, wherein the undersurface of the adhesive pad includes an adhesive material configured to adhere the adhesive pad to the skin of the host, and wherein the adhesive pad comprises a first material; and a reinforcing overlay having an upper surface, an undersurface, and a central opening configured to allow at least a portion of the housing to protrude therefrom, wherein the undersurface of the overlay includes an adhesive material configured to adhere the overlay to the adhesive pad and to the skin of the host, and wherein the overlay comprises a second material.

In an embodiment of the eleventh aspect, the first material is a fabric and the second material is a polymer.

In a twelfth aspect, an adhesive pad system is provided for securing a continuous analyte sensor assembly to skin of a host, the system comprising: a housing configured to receive a sensor electronics unit; and an adhesive pad having an upper surface and an undersurface, wherein the housing is secured to the upper surface of the adhesive pad, wherein the undersurface of the adhesive pad includes an adhesive material configured to adhere the adhesive pad to the skin of the host; wherein a perimeter edge of the adhesive pad includes a reduced thickness relative to an interior portion of the adhesive pad.

In an embodiment of the twelfth aspect, the perimeter edge has a thickness that is from about 5% to about 95% of the thickness of the interior portion.

In an embodiment of the twelfth aspect, the perimeter edge has a thickness that is from about 10% to about 80% of the thickness of the interior portion.

In an embodiment of the twelfth aspect, the perimeter edge has a thickness that is from about 25% to about 75% of the thickness of the interior portion.

In an embodiment of the twelfth aspect, the perimeter edge has a thickness that is from about 33% to about 50% of the thickness of the interior portion.

BRIEF DESCRIPTION OF THE DRAWINGS

The various embodiments of the present systems and methods for securing a continuous analyte sensor to a host now will be discussed in detail with an emphasis on highlighting the advantageous features. These embodiments depict the novel and non-obvious systems and methods for securing a continuous analyte sensor to a host shown in the accompanying drawings, which are for illustrative purposes only. These drawings are not necessarily drawn to scale, and they are provided merely to illustrate the present embodiments. These drawings include the following figures, in which like numerals indicate like parts:

FIGS. 35-40 are schematic side elevation views of one embodiment of an applicator device for an adhesive pad of an adhesive sensor system, showing successive stages of a process for securing the adhesive pad to a host's skin using the applicator device;

FIGS. 41C1-C4 illustrate a method for applying an adhesive pad onto a skin;

DETAILED DESCRIPTION

Figure 1:
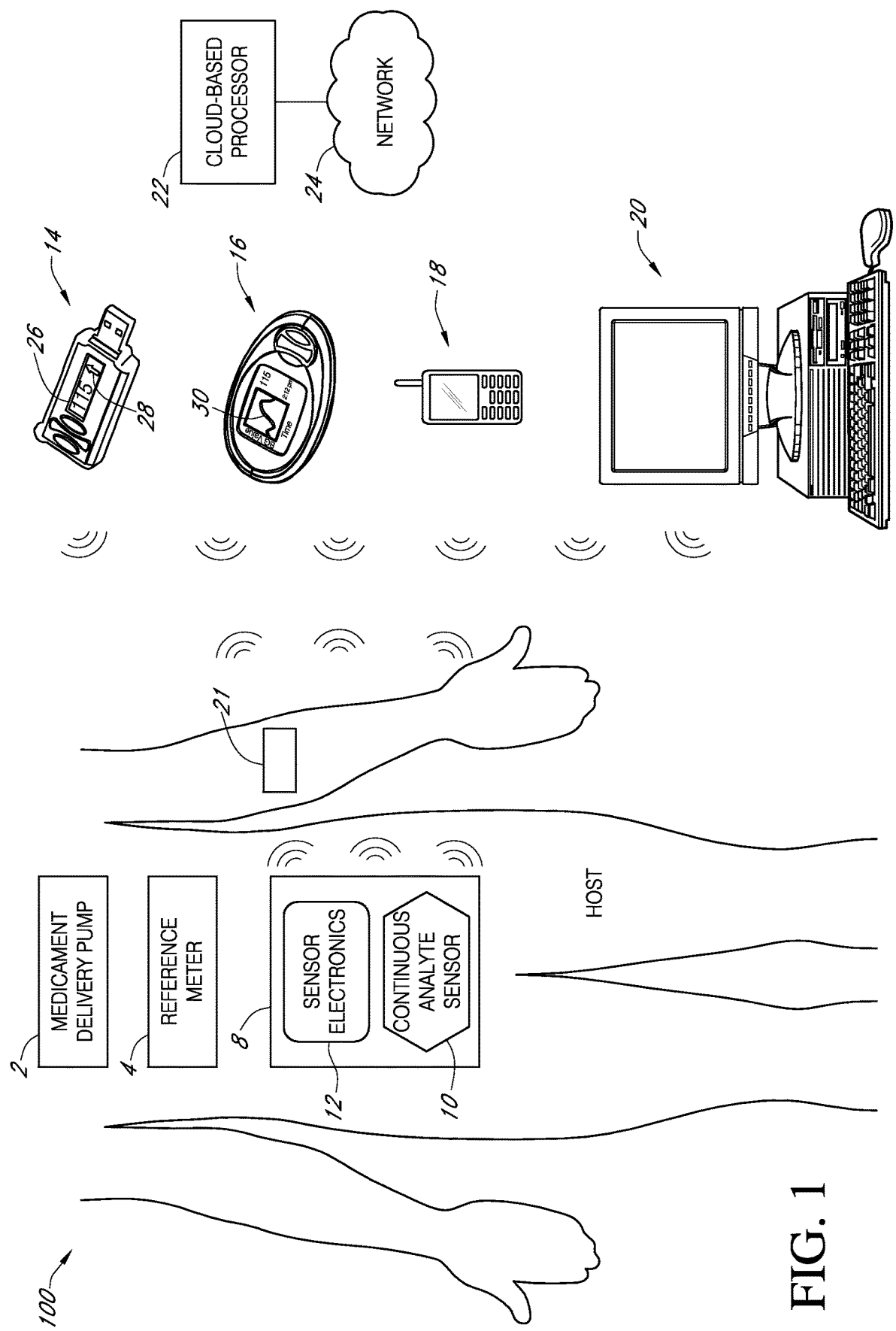
FIG. 1 is a schematic view of a continuous analyte sensor system attached to a host and communicating with other devices.

The following detailed description describes the present embodiments with reference to the drawings. In the drawings, reference numbers label elements of the present embodiments. These reference numbers are reproduced below in connection with the discussion of the corresponding drawing features.

The embodiments of the present systems and methods for securing a continuous analyte sensor to a host are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

The present embodiments include methods of securing a continuous analyte sensor to a host. Some of these embodiments may be performed in connection with treating a human and/or animal body. Others of these embodiments may be performed independently of a human and/or animal body, such as for purposes of testing or demonstration. Accordingly, the present embodiments pertaining to methods of securing a continuous analyte sensor to a host should not be construed as limited to methods of treating a human and/or animal body.

Sensor

The preferred embodiments relate to the use of an analyte sensor that measures a concentration of glucose or a substance indicative of the concentration or presence of an analyte. In some embodiments, the analyte sensor is a continuous device, for example a subcutaneous, transdermal, transcutaneous, and/or intravascular (e.g., intravenous) device. In some embodiments, the device can analyze a plurality of intermittent blood samples. The analyte sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of the preferred embodiments can be applied to any measurable analyte. In some preferred embodiments, the analyte sensor is a glucose sensor capable of measuring the concentration of glucose in a host. One example embodiment is described below, which utilizes an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Application Publication No. 2011/0027127. In another preferred embodiment, the analyte sensor is a transcutaneous glucose sensor, such as described with reference to U.S. Patent Application Publication No. 2006/0020187. In yet another preferred embodiment, the analyte sensor is a dual electrode analyte sensor, such as described with reference to U.S. Patent Application Publication No. 2009/0137887. In still other embodiments, the sensor is configured to be implanted in a host vessel or extracorporeally, such as is described in U.S. Patent Application Publication No. 2007/0027385.

Deposition Techniques

The membrane system can be deposited on the exposed electroactive surfaces using any of a variety of known thin film techniques (for example, vapor deposition, spraying, printing (e.g., pad printing), electro-depositing, dipping, sputtering deposition, spin coating, powder coating, and the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art.

Analyte List

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate or lactic acid; cardiac markers; ketone bodies: acetone; acetoacetic acid; beta hydroxybutyric acid; glucagon, acetyl Co A; intermediaries in the Citric Acid Cycle; choline, testosterone; creatinine; triglycerides; sodium; potassium; chloride; bicarbonate; total protein; alkaline phosphatase; calcium; phosphorus; $PO_2$; $PCO_2$; bilirubin (direct and total); red blood cell count; white blood cell count; hemoglobin; hematocrit; lymphocytes; monocytes; eosinophils; basophils; c-reactive protein; cryoglobulins; fibrinogens; ACTH; aldosterone; ammonia; beta-HCG; magnesium; copper; iron; total cholesterol; low density lipoproteins; high density lipoproteins; lipoprotein A; T4 (total and free); TSH; FSH; LH; ACTH; hepatitis BE antigen; hepatitis B surface antigen; hepatitis A antibody; hepatitis C antibody; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; cortisone, creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, epinephrine, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, Plasmodium *falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

High-Level CGM System Description

For illustrative purposes, reference will now be made to FIG. 1, which is an example environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate to sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18, 20, and 21.

The system 100 of FIG. 1 also includes a cloud-based processor 22 configured to analyze analyte data, medicament delivery data, and/or other patient related data provided over network 24 directly or indirectly from one or more of sensor system 8, medicament delivery pump 2, reference analyte meter 4, and display devices 14-21. Based on the received data, the processor 22 can further process the data, generate reports providing statistic based on the processed data, trigger notifications to electronic devices associated with the host or caretaker of the host, or provide processed information to any of the other devices of FIG. 1. In some example implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

Although the example implementation described with respect to FIG. 1 refers to analyte data being received by processor 22, other types of data processed and raw data may be received as well.

In some example implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, 20, and 21. The display devices 14, 16, 18, 20, and/or 21 may be configured for processing and presenting information, such sensor information transmitted by the sensor electronics module 12 for display at the display device. The display devices 14, 16, 18, 20, and 21 can also trigger alarms based on the analyte sensor data.

In FIG. 1, display device 14 is a key fob-like display device, display device 16 is a hand-held application-specific computing device 16 (e.g. the DexCom G4® Platinum receiver commercially available from DexCom, Inc.), display device 18 is a general purpose smart phone or tablet computing device 20 (e.g. an Apple® iPhone®, iPad®, or iPod Touch® commercially available from Apple, Inc.), display device 20 is a computer workstation 20, and display device 21 is any wearable. In some example implementations, the relatively small, key fob-like display device 14 may be a computing device embodied in a wrist watch, a belt, a necklace, a pendent, a piece of jewelry, an adhesive pad, a pager, a key fob, a plastic card (e.g., credit card), an identification (ID) card, and/or the like. This small display device 14 may include a relatively small display (e.g., smaller than the display device 18) and may be configured to display a limited set of displayable sensor information, such as a numerical value 26 and/or an arrow 28. In contrast, display devices 16, 18, and 20 can be larger display devices that can be capable of displaying a larger set of displayable information, such as a trend graph 30 depicted on the hand-held receiver 16 in addition to other information such as a numerical value and arrow.

Any other user equipment (e.g. computing devices) configured to at least present information (e.g., a medicament delivery information, discrete self-monitoring analyte readings, heart rate monitor, caloric intake monitor, and the like) can be used in addition to or instead of those discussed with reference to FIG. 1.

In some example implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations of FIG. 1, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprised of any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

Adhesion to the Host

One aspect of the present embodiments includes the realization that current adhesive pads with the mounting units (i.e., the sensor assembly disposed on the adhesive pad, including, for example, the sensor electronics housing, the sensor electronics, etc.) adhered thereon may not remain adhered to the host's skin for a desired duration. In fact, issues relating to the adhesive pad adhering to the skin are some of the primary factors that result in shortened sensor life. As the adhesive pad starts to peel off from the skin, movement from the adhesive pad (e.g., from inadvertent pushing or pulling of the mounting unit) can be translated through the length of the sensor to the in vivo portion of the sensor and cause complications and undesired effects. For example, movement translated to the in vivo portion of the sensor can cause irritation and inflammation. In turn, these conditions can cause various forms of wound healing response from the patient's body, all of which can result in sensor inaccuracy, sensor failure, and/or shortened sensor life. If the adhesive pad (and the mounting unit attached thereon) prematurely becomes completely detached from the skin, the sensor, which is attached to the mounting unit, will likely be pulled out of the patient's body, thereby prematurely terminating the sensor session.

When a user begins a new sensor session, it is desirable for that sensor to remain within the host for at least about seven days, preferably at least about 10 days, more preferably at least about 14 days, even more preferably at least about 20 or 21 days, and still even more preferably at least about one month. Without an adhesive pad that is capable of adhering to a patient's skin for the above-described number of days, the sensor may not remain in the host for the desired time. This is problematic because of the inconvenience of having to replace a sensor. If one has to constantly replace sensors because of failure of adhesive pads, this over time can become quite costly to the user. In the future, the target sensor session length may be even longer. Therefore, there is a need for an adhesive pad system that provides long lasting and stable adherence of the mounting unit to the host's skin. In some embodiments, the adherence is capable of persisting from about ten days to about fourteen days when worn under normal conditions.

Another aspect of the present embodiments includes the realization that adhesives present unique design challenges in the context of wearable sensors. For example, as compared to adhesive bandages or other medical patches, the adhesive pad of a wearable sensor has to be capable of supporting the mass and volume of the sensor assembly, and be robust enough to resist pushing and pulling forces on that mass and volume (to resist detachment of the sensor assembly from the skin) Also, in contrast to other conventional patches, bandages, and medical tapes, if the adhesive of the present embodiments fails before a preselected number of days have elapsed since sensor insertion, the wearer cannot simply swap out the failed adhesive pad for another adhesive pad, at least not without possibly destroying the sensor and/or ending the sensor session. But sensors are quite costly. Therefore, it is highly desirable to avoid destroying the sensor before its useful life has elapsed.

Moisture buildup between the wearer's skin and the adhesive pad over-hydrates (macerates) the skin, causing the outer skin layer(s) to shed faster than normal. When the outer layer of the skin sheds, the adhesive pad tends to become detached from the wearer. This premature peel-off of an adhesive pad can be problematic even before the adhesive pad completely detaches from the skin. When the adhesion between the adhesive pad and the skin becomes weak and not sufficiently stable, the electronics housing and the sensor in contact therewith may become susceptible to undesired shaking and movement. Movement at the ex vivo portion of the sensor that contacts the electronics housing can translate across the length of the sensor to the in vivo portion of the sensor and cause complications and undesired effects. For example, movement translated to the in vivo portion of the sensor and cause irritation and inflammation. In turn, these conditions can cause various forms of wound healing response from the patient's body, all of which can result in sensor inaccuracy, sensor failure, and/or shortened sensor life.

Anything that can improve, or at least maintain, skin health helps retain the outer layer(s) of skin, which in turn leads to better long-term adhesion of the sensor system to the wearer. Maintaining normal or near normal breathability for oxygen and moisture transmission through the adhesive pad helps to maintain skin health, and higher MVTR is generally advantageous for longer wear time and better adhesion. Other factors that may improve adhesion include the ability of the adhesive pad to conform to the wearer's skin, and the thickness of the patch.

A. Material Selection

Figure 42A:
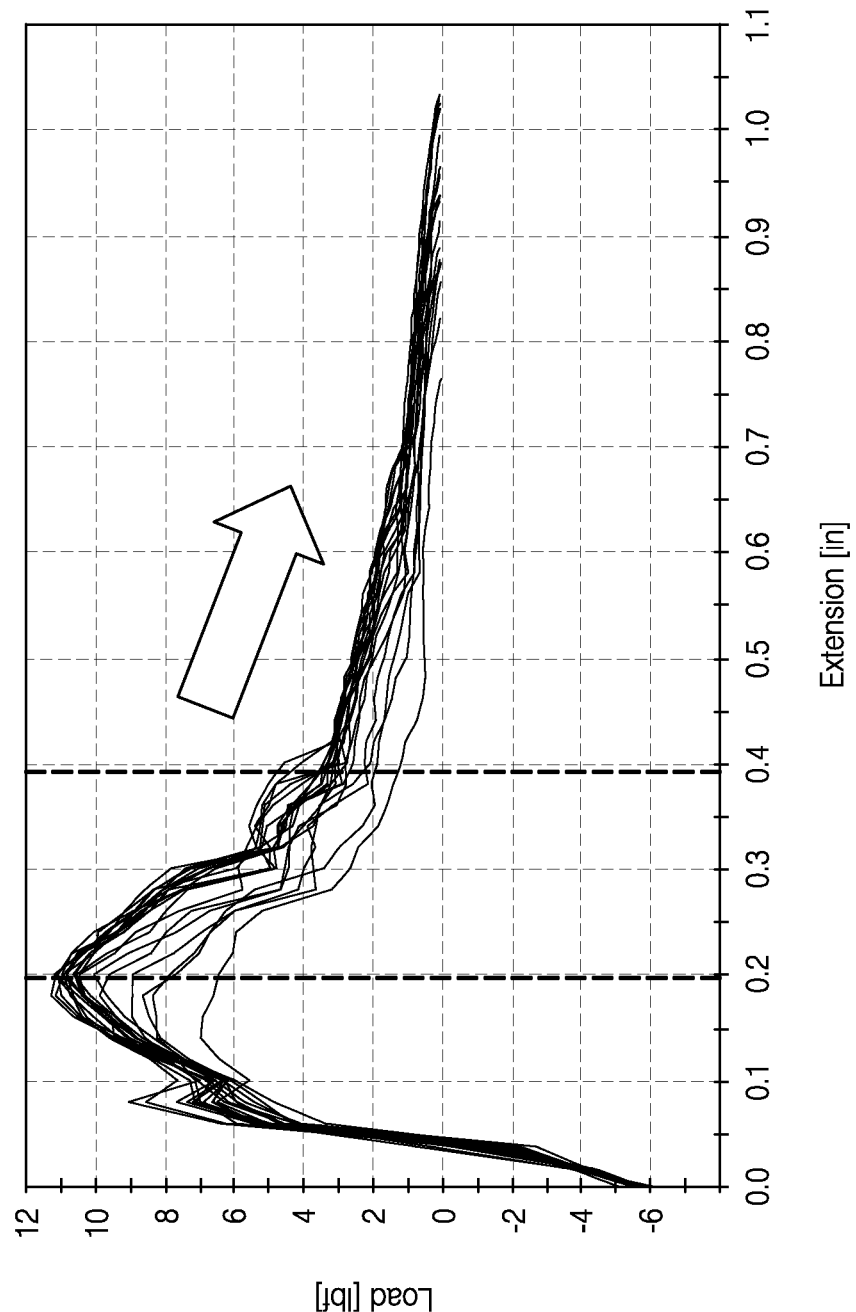
FIGS. 42A-B illustrate results from tests conducted to determine the adhesive strength of adhesive pads, as compared to the strength of adhesive pads reinforced with overlays.
Figure 42B:
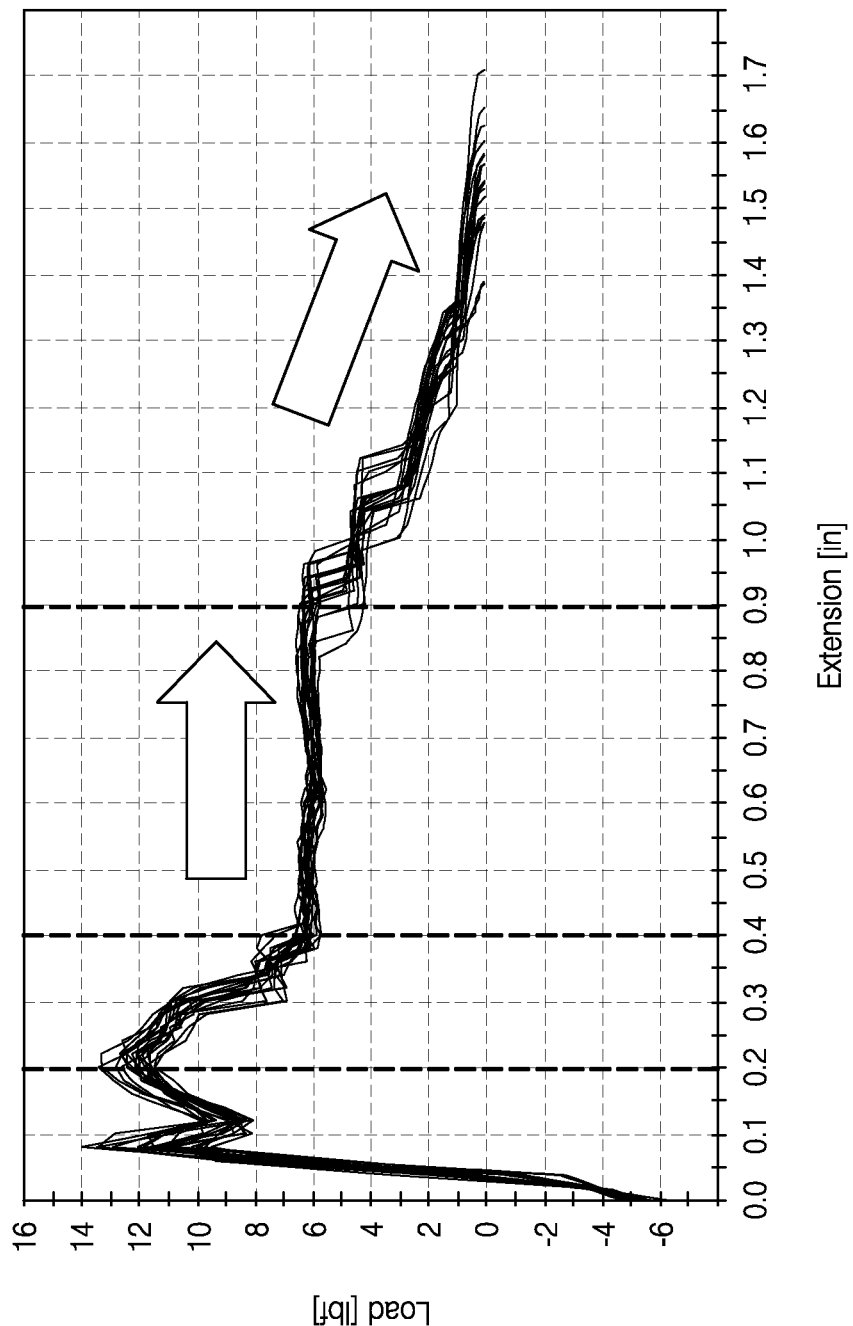

In recognition of the foregoing problem, as well as in recognition of any of the other problems discussed herein, some of the present embodiments may include an adhesive material that is capable of maintaining strong adhesion to the host, even after seven, ten, twelve, fourteen, twenty one, or more days of continuous wear. Such a material can be used to form an adhesive pad capable of adhering to a patient's skin for seven days, ten, twelve, fourteen, twenty-one, or more days, so that the sensor remains the host for the desired number of days. An adhesive pad not capable of providing stable continuous adhesion to the skin for a particular number of days (e.g., 14 days), when the corresponding sensor has a useful life of the aforementioned particular number of days (e.g., 14 days), is problematic because implantable sensors are not without costs. Thus, having to constantly replace sensors designed and approved to work for a particular number of days (e.g., 14 days) prior to that duration can be expensive to the patient and cause great inconvenience. Described herein are certain embodiments of adhesive pad designs that are configured to provide sufficiently stable support for a mounting unit (e.g., the sensor electronics, such as a transmitter, and the sensor electronics housing) with a mass from about 2 grams to about 15 grams, preferably from about 8 to about 12 grams, and preferably from about 9 to about 11 grams. In addition, certain of the present embodiments described herein are configured to provide sufficiently stable support for a mounting unit with a sensor electronics housing with a volume from about 500 $mm^3$ to 2,000 $mm^3$, preferably from about 800 $mm^3$ to 1,500 $mm^3$, and a sensor electronics unit (e.g., transmitter) with a volume from about 1,000 $mm^3$ to about 7,000 $mm^3$, and preferably from about 3,000 $mm^3$ to about 5,000 $mm^3$. Furthermore, certain of the present embodiments described herein are configured to provide sufficiently stable support for a mounting unit with a maximum height (as measured from a base defined by upper surface of the top layer of the sensor adhesive pad) of from about 3 mm to about 20 mm, preferably from about 7 mm to about 15 mm, and more preferably from about 9 mm to about 12 mm. To provide sufficiently stable support, certain embodiments described herein are configured to resist pushing and pulling forces on the mass and volume of the mounting. The above-described resistance provided by certain embodiments is at a level such that the adhesive pad will substantially remain in place and substantially hold the sensor in place and in the correct alignment when the mounting unit is pulled or pushed through routine incidental contact. As illustrated in FIGS. 42A and 42B, in certain embodiments, the adhesive pad system is configured to resist forces, acting on the adhesive pad system, that are greater than about 6 lbf, greater than about 8 lbf, greater than about 10 lbf, greater than about 11 lbf, greater than about 12 lbf, and greater than about 13 lbf and provide stable sensor performance while the above-mentioned levels of forces are applied thereto. It should be understood that the present embodiments described herein are not limited in their performance capabilities to the metrics (e.g., a certain force resistance and support of a mounting unit with a certain height, mass, volume)

described above. Rather, it should be understood that certain embodiments may have performance capabilities that are higher or lower than the metrics described above. By example, in alternative embodiments, the adhesive pad may be configured to support a device with a mounting unit with a mass less than two grams or a mass greater than 15 grams.

An adhesive pad typically comprises a pad, an adhesive that adheres the pad to the skin during use, and one or more backings that are peeled off from an adhesive side of the pad prior to application. The pad may comprise any of a variety of materials, such as, for example, nonwoven spunlace, polyurethane, polyester, and polyethylene. The adhesive layer of the adhesive pad can be formed of any sterile, pressure-sensitive, non-toxic, adhesive suitable for adhesion to healthy human skin. While the adhesive layer adheres to healthy human skin, the adhesive preferably has little or no tendency to adhere to an open wound caused by sensor insertion. Examples of suitable pressure-sensitive adhesives include, but are not limited to, acrylic-based, dextrin-based, urethane-based, rubber-based, polyvinyl-ether-based adhesives, and other adhesives based on natural and synthetic elastomers. Other examples include use of nano/micron scaled textured surfaces for wearable sensor applications. Nano/micron scaled textured surfaces have been demonstrated to provide excellent dry adhesion to contour surfaces.

In selecting an adhesive material, many properties may be considered, such as, and without limitation, adhesive strength, gas permeability, moisture vapor transmission rate (MVTR), appearance (e.g., color, design, texture), tape thickness, elongation, conformability, quality, biocompatibility, manufacturability, and ability to withstand sterilization processes.

Also in recognition of the foregoing problem, as well as in recognition of any of the other problems discussed herein, some of the present embodiments include an adhesive pad having strong adhesiveness with a high peel-off force required to remove the pad from the host. Results of peel tests conducted by the inventors are provided below to quantify the force required to remove selected materials from a test surface.

Adhesive strength or peel adhesion is the force required to remove a pressure sensitive tape from a test panel or its own backing at a controlled angle, at a standard rate, and under standard conditions. The tables below provide test data for peel tests conducted by the inventors to quantify the peel adhesion of example materials that may in some embodiments be used in connection with the adhesive pad system 200. The test sets are single- or double-sided medical tapes. All tests were divided into two groups: unsterilized vs. sterilized. All sets were cut into 1"×12" strips and have 1-mil polyester tape on one side. All sets were tested according to the ASTM D3330 standard Test Method A—Single-Coated Tapes, Peel Adhesion at 180° Angle. In accordance with ASTM D3330 standard Test Method A, a strip of tape was rolled mechanically twice in each lengthwise direction, causing the roller to apply the tape to a standard test panel (stainless steel panel). The tape is peeled from the panel at a 180° angle at a specified rate (12 in/min), during which time the force required to effect peel is measured. The average load per width is a value determined using the average load calculated from peeling off the tape from 1" to 3" of the tape's length along with the tape's width.

The average load per width is a calculated value using the average load calculated from 1" to 3" and the specimen width.

TABLE I

Materials Tested

| Patch Material | Description | Tape | Thickness (mil) | Test Qty. |
|---|---|---|---|---|
| 3M 9907W | Melt Blown Polyurethane | Single-sided | 10 | 10 |
| 3M 9833 | Polyurethane | Single-sided | 2.1 | 10 |
| 3M 9834 | Polyurethane | Single-sided | 1.8 | 10 |
| 3M 1776 | Nonwoven Spunlace | Single-sided | 11.5 | 10 |
| MacTac TM5300 | Polyurethane | Single-sided | 4 | 10 |
| MacTac TM5110 | Polyurethane | Single-sided | 2 | 10 |
| 3M 9917 | Nonwoven Spunlace | Double-sided | 12 | 10 |
| 3M 1526 | Polyethylene | Single-sided | 5 | 10 |
| DM2001 | Nonwoven Spunlace | Single-sided | 10 | 29 |
| DM2001-C | Nonwoven Spunlace | Single-sided | 10 | 29 |

TABLE II

Test Results

| Sets | Sterilization | Test Qty. | Mean (g/inch) | Std Dev (g/inch) |
|---|---|---|---|---|
| 3M 9907W | unsterilized | 10 | 1431.65 | 140.32 |
| 3M 9833 | unsterilized | 10 | 796.62 | 45.22 |
| 3M 9834 | unsterilized | 10 | 569.83 | 54.20 |
| 3M 1776 | unsterilized | 10 | 535.81 | 63.32 |
| MacTac TM5300 | unsterilized | 10 | 1207.69 | 142.19 |
| MacTac TM5110 | unsterilized | 10 | 1122.64 | 50.36 |
| 3M 9917 | unsterilized | 10 | 697.40 | 35.86 |
| 3M 1526 | unsterilized | 10 | 1304.08 | 76.77 |
| DM2001 | unsterilized | 29 | 759.57 | 81.03 |
| DM2001-C | unsterilized | 29 | 777.17 | 67.14 |
| 3M 9907W | sterilized | 10 | 1519.53 | 75.83 |
| 3M 9833 | sterilized | 10 | 700.23 | 32.87 |
| 3M 9834 | sterilized | 10 | 640.70 | 35.86 |
| 3M 1776 | sterilized | 10 | 544.31 | 71.72 |
| MacTac TM5300 | sterilized | 10 | 1080.12 | 86.04 |
| MacTac TM5110 | sterilized | 10 | 853.32 | 41.08 |
| 3M 9917 | sterilized | 10 | 601.01 | 45.91 |
| 3M 1526 | sterilized | 10 | 1570.56 | 58.56 |
| DM2001 | sterilized | 29 | 723.40 | 74.48 |
| DM2001-C | sterilized | 29 | 762.50 | 73.59 |

In the foregoing tests, each of the sterilized test samples were subjected to the following sterilization parameters prior to testing: Test samples were e-beam sterilized and each received a dose from about 25 kGy to about 35 kGy.

Another aspect of the present embodiments includes the realization that it is advantageous for the adhesive pad to remain adhered to the host's skin for a desired duration, but when it is desired to remove the pad, it is advantageous for the removal process to be quick and comfortable. Therefore, there is a need for an adhesive pad system that provides long lasting adherence of the mounting unit to the host's skin, but is also easy to remove when desired. Because of the additional mass and weight of the mounting unit (e.g., sensor electronics housing and the electronics disposed thereon), as compared to a conventional medical bandage not designed to be loaded with additional objects, finding the right balance between strong adhesion and ease or adhesive pad removal can be challenging.

In recognition of the foregoing problem, as well as in recognition of any of the other problems discussed herein, some of the present embodiments enable the adhesiveness of the pad to be selectively reduced or deactivated by the wearer. In some embodiments, adhesiveness of the pad is reduced or deactivated by applying a material, such as a solvent (e.g., dipropylene glycol methyl ether, isoparaffin, and isopropyl alcohol), to the pad. Applying such a material facilitates easy removal of the adhesive pad from the host's skin. Thus, when the host desires to remove the adhesive pad, such as at the end of a sensor session, he or she may apply an adhesive reducing material to the pad prior to peeling the pad off his or her skin. Facilitating easy removal of the pad from the skin may help to reduce or eliminate irritation to the host's skin.

In other embodiments, the adhesive pad comprises an adhesive reducing material held in one or more self-contained selectively rupturable reservoirs (e.g., held by encapsulation in microcapsules). In certain embodiments, one or more adhesion reducing material matrices embedded with the adhesion reducing material are selectively deformable to release the material. The adhesion reducing material may comprise any of a variety of materials capable of reducing the adhesive forces between the wearer's skin and the adhesive pad, thereby reducing pain and body effacement during removal. Examples of adhesion reducing materials include, but are not limited to, oil (e.g., olive oil, safflower oil, cottonseed oil, peanut oil, soybean oil, castor oil, sesame oil, aloe vera, and eucalyptus oil), various forms of hydrocarbons, and solvents (e.g., dipropylene glycol methyl ether, isoparaffin, and isopropyl alcohol) capable of reducing adhesiveness of the adhesive materials described herein.

In certain embodiments, the package provided to patients contains different adhesive pads, each with different adhesive strengths. This arrangement provides users with the opportunity to try various adhesive pads with different adhesives to determine which particular adhesive pad and its corresponding adhesive strength works best. After determining the adhesive pad with the optimal adhesive strength for the user, the user can then order a particular type of package that contains only the selected adhesive pad with the adhesive strength optimized for the user.

In some embodiments, a barrier film is applied to the skin prior to application of the adhesive pad to reduce the likelihood of skin irritation and to make removal of the adhesive pad less painful. The barrier film forms a protective, breathable film barrier between the skin and the adhesive pad. Examples of barrier films include, for example, 3M Cavilon No Sting Barrier Film, ConvaTec AllKare Protective Barrier Wipes, Covidien Webcol Skin Barrier Wipes, and Brava Skin Barrier. In certain embodiments, the barrier film is a sting-free, alcohol-free liquid barrier film that dries quickly to form a breathable, transparent coating on the skin. The barrier film(s) can be breathable and are designed to protect intact or damaged skin from, inter alia, tape trauma, irritation, excoriation, adhesive build-up, and/or friction.

Another aspect of the present embodiments includes the realization that the mounting unit of a continuous analyte monitoring system desirably remains secured to the host's skin for several days, including up to fourteen days. Since the adhesive pad at least partially covers the host's skin throughout this period, the pad desirably has high gas permeability. High gas permeability provides several advantages. For example, air circulation close to the host's skin reduces or prevents moisture buildup between the skin and the adhesive pad, which could undermine the effectiveness of the adhesive. Thus, high gas permeability for the adhesive pad may assist in prolonging the lifespan of the adhesive pad. In another example, air circulation through the adhesive pad provides oxygen to the covered area of the host's skin.

Therefore, there is a need for an adhesive pad system having high gas permeability. High gas permeability can reduce the risk of premature peel-off. As discussed above, premature peel-off of an adhesive pad can be problematic even before the adhesive pad completely detaches from the skin. When the adhesion between the adhesive pad and the skin becomes weak and not sufficiently stable, the electronics housing and the sensor in contact therewith may become susceptible to undesired shaking and movement. Movement at the ex vivo portion of the sensor that contacts the electronics housing can translate across the length of the sensor to the in vivo portion of the sensor and cause complications and undesired effects. For example, movement translated to the in vivo portion of the sensor and cause irritation and inflammation. In turn, these conditions can cause various forms of wound healing response from the patient's body, all of which can result in sensor inaccuracy, sensor failure, and/or shortened sensor life.

In recognition of the foregoing problem, as well as in recognition of any of the other problems discussed herein, some of the present embodiments are designed to provide improved gas permeability. For example, in some embodiments, at least a portion of the adhesive pad is formed from a suitable porous material, such as, knits, wovens (e.g., cheesecloth and gauze), nonwovens (including spun-bonded nonwovens), extruded porous sheets (e.g., polyurethane), and perforated sheets (e.g., polyurethane), for example. The apertures (e.g., openings) in the porous material are preferably of sufficient size and sufficient number to facilitate high breathability. The apertures can be through-holes or slit cuts, for example. The size and pitch of the aperture preferably is large enough to allow sweat and moisture from the body to evaporate quickly and effectively. While not wishing to be bound by theory, it is believed that if the size of the apertures is too large water can enter from external sources and the skin will get wet, thereby resulting in weaker adhesive pad adhesion. If the pitch (or the distance from one aperture to the next) is too close, the apertures may weaken the integrity of the adhesive pad system and cause it to tear and break apart. For certain embodiments, the porous materials have between about 1 and about 200 apertures per square centimeter, sometimes between about 25 and about 75 apertures, and other times between about 115 and 175 apertures. In some embodiments, the apertures have an average opening size (the largest dimension of the opening) of at least about 0.01 mm, about 0.05 mm, or about 0.1 mm. For certain embodiments, the apertures have an average opening size (the largest dimension of the opening) of no greater than about 0.05 cm, no greater than about 0.1 cm, or no greater than about 0.5 cm. In some embodiments, the adhesive pad has a Moisture Vapor Transmission Rate (MVTR) between about 1,000 g/24 hrs/m$^2$ and about 3,000 g/24 hrs/m$^2$, preferably from about 1,500 g/24 hrs/m$^2$ to about 2,500 g/24 hrs/m$^2$, and more preferably from about 2,000 g/24 hrs/m$^2$ to about 2,300 g/24 hrs/m$^2$.

In some embodiments, to improve breathability and gas permeability, the adhesive coating applied to the adhesive pad may possess a patterned adhesive coating. Instead of having an adhesive pad with uniform gas permeability across its entire surface, a pattern (e.g., a pattern corresponding to a layout of the pores) may be introduced during coating of an adhesive material onto the pad to provide variations in gas permeability across the pad, for example, in the form of a pattern that promotes breathability while still maintaining sufficient mechanical strength to prevent susceptibility to damage. While not wishing to be bound by theory, it is believed that greater air permeation to the skin will reduce skin cell death rate, which is accelerated when the skin is unable to breathe while covered by a conventional bandage. The dead skin cells, in turn, accumulate into clumps, which in turn, reduces adhesion between the adhesive pad and the skin. By having the above-described materials and/or porous pad design, the skin's ability to "breathe" better is increased, thereby resulting in less dead skin cells and thus a slower death rate. As a result, the useful life is the adhesion pad is increased.

Another aspect of the present embodiments includes the realization that, according to current practice, the mounting unit of a continuous analyte monitoring system typically undergoes sterilization after assembly, e.g., after the adhesive pad has been assembled to the mounting unit. One type of sterilization process is electron beam processing, also referred to as electron irradiation or e-beaming. E-beaming is a process involving the use of electrons, usually of high energy, to kill microbes that may be resident on the object being irradiated. The e-beaming process, which may take place under elevated temperature and/or in a nitrogen atmosphere, typically weakens the adhesiveness of the adhesive pad.

In recognition of the foregoing problem, as well as in recognition of any of the other problems discussed herein, some of the present embodiments provide adhesive pad systems having resistance to e-beaming. For example, Table II discloses certain materials that are resistant to decreased adhesiveness after exposure to e-beam sterilization. In some embodiments, an adhesive pad may include a backing layer (the part that is peeled off to expose the adhesive material) having a layer of a material that reflects or redirects the e-beam. Example reflective materials include, without limitation, aluminum foil, biaxially-oriented polyethylene terephthalate (BoPET, available under the trade name MYLAR), and polytetrafluoroethylene.

In some embodiments, an antiseptic or disinfectant may be incorporated into the adhesive pad. Examples of antiseptics and disinfectants are hexachlorophene, cationic bisiguanides (e.g., chlorhexidine, cyclohexidine) iodine and iodophores (e.g., povidoneiodine), para-chloro-meta-xylenol, triclosan, furan medical preparations (e.g., nitrofurantoin, nitrofurazone), methenamine, aldehydes (glutaraldehyde, formaldehyde) and alcohols. Other examples of antiseptics and disinfectants will readily suggest themselves to those of ordinary skill in the art.

In certain embodiments, medicament may be incorporated into the adhesive pad, which releases the medicament over time while adhered to the skin. The medicament can be any of a variety of drugs, such as, for example, insulin or other drugs for treating diabetes. To facilitate transdermal passage, different mechanisms and systems may be used, such as e.g. techniques involving formation of microchannels or micropores in the skin, such as e.g. iontophoresis (based on low-level electrical current), sonophoresis (based on low-frequency ultrasound) or microneedling, or the use of drug-carrier agents (e.g. elastic or lipid vesicles such as transfersomes) or permeation enhancers.

It should be understood that any of the materials described herein (e.g., materials for the pad or for the adhesive material) and their associated properties (e.g., resistance to decreased weaknesses as a result of exposure to e-beam sterilization) may be used and/or are applicable to other adhesive sensor systems described herein.

B. Adhesive Sensor Systems

One aspect of the present embodiments includes the realization that certain adhesive pads may not remain adhered to the host's skin for a desired duration. For example, when a user begins a new sensor session, it is desirable for that sensor to remain within the host for up to about seven days. In the future, the target sensor session length may be even longer, such as up to about fourteen days or twenty one days. Therefore, there is a need for an adhesive pad system that provides long lasting adherence of the mounting unit (i.e., the wearable ex vivo portion of the sensor system) to the host's skin. In some embodiments, the adherence is capable of persisting for about ten days to about fourteen days.

1. Replaceable Reinforcing Overlay

In recognition of the foregoing problem, as well as in recognition of any of the other problems discussed herein, some of the present embodiments provide one or more reinforcing overlays covering an adhesive pad. Advantageously, the reinforcing overlay can be periodically replaced if it loses adhesiveness.

Figure 2:
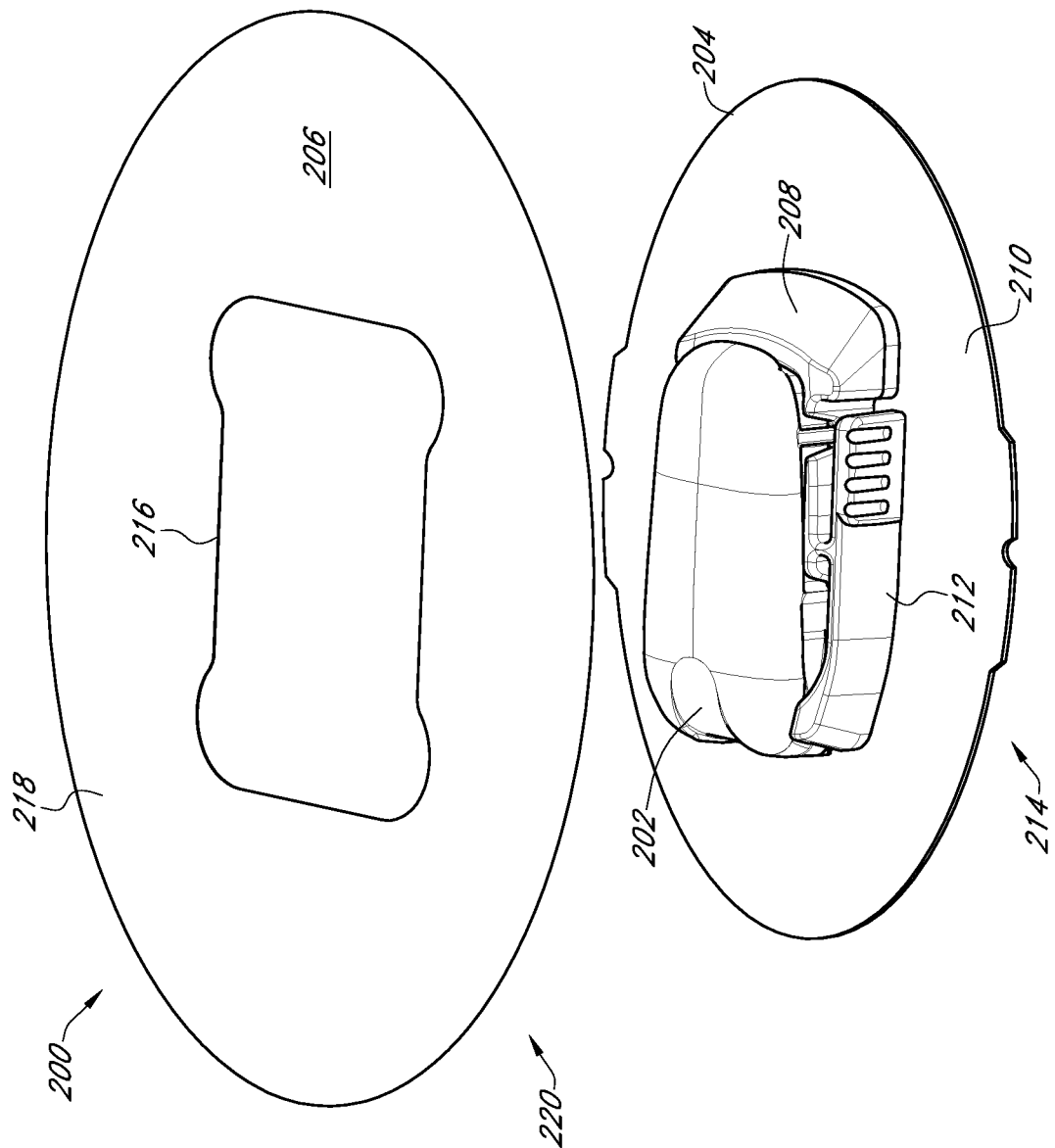
FIG. 2 is a partially exploded upper perspective view of one embodiment of an adhesive sensor system including a replaceable reinforcing overlay.
Figure 3:
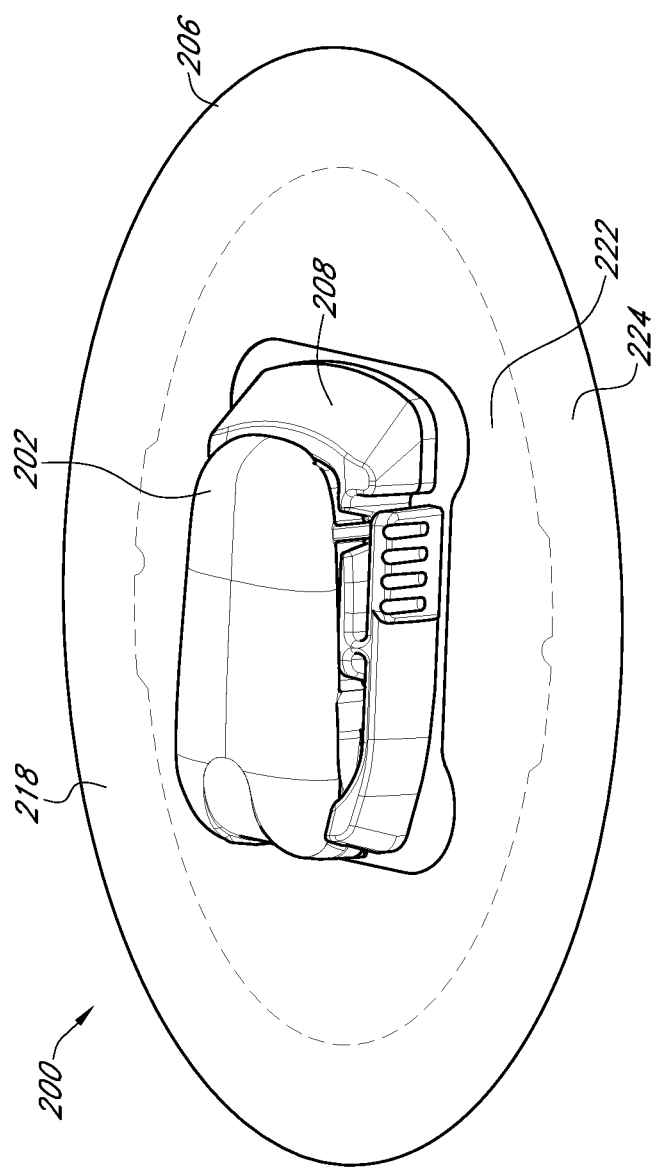
FIG. 3 is an assembled upper perspective view of the adhesive sensor system of FIG. 2.

FIGS. 2 and 3 illustrate an example embodiment of an adhesive sensor system 200 including a sensor electronics unit 202 secured to an adhesive pad 204 and a replaceable reinforcing overlay 206. With reference to FIG. 2, the sensor electronics unit 202 is received within an electronics housing 208 that is secured to an upper surface 210 of the adhesive pad 204. The electronics housing 208 may be secured to the adhesive pad 204 by any of a variety of methods. In one embodiment, the adhesive pad 204 is joined to the electronics housing 208 with glue. In another embodiment, a thermoplastic staking process is used instead. During this process, the electronics housing 208 is heated to a predetermined temperature, which softens the housing 208. Thereafter, the electronics housing 208 is pressed against an adhesive pad 204 at a predetermined pressure and allowed to cool. Heat-staking is often a preferred technique for adhering the electronics housing to a component of the adhesive pad, because the technique allows for automation, which in turn allows for scaling up. It should be understood that use of heat-staking is not limited to the manufacturing of the embodiment illustrated in FIG. 2, but instead can be used in any of the embodiments described herein.

The adhesive pad 204 is shaped substantially as a thin, flat, sheet that extends beneath the housing 208 and extends outwardly on all sides from a periphery 212 of the electronics housing 208. The adhesive pad 204 includes at least one opening (not shown) beneath the electronics housing 208. The sensor (not shown) passes through the opening so that a portion of the sensor extends into the host's skin. In the illustrated embodiment, the adhesive pad 204 is shaped substantially as an oval in plan view, but the illustrated shape is just one non-limiting example. In other embodiments, the adhesive pad may have a shape that is circular, rectangular, square, or any other polygonal shape. In another embodiment, the adhesive pad may have a shape that corresponds to the shape of the electronics housing, but with dimensions equal to or greater than the corresponding dimensions of the electronics housing 208.

The adhesive pad 204 comprises a sheet of flexible and resilient material. In some embodiments, the adhesive pad 204 comprises a single layer of material. In other embodiments, the adhesive pad 204 may comprise a plurality of layers. In some of these embodiments, one or more layers can be waterproof or water-resistant, and/or one or more other layers can be moisture absorbent. Example materials for the adhesive pad 204 include, without limitation, fabrics (e.g. spunlace), polymers (e.g., polyurethane, polyethylene, polyester, etc.), film, paper, cotton, silk, and/or any other desired material and combinations thereof. In some embodiments, the adhesive pad 204 can be smooth, but in other embodiments the adhesive pad 204 can be textured. The adhesive pad 204 may be hypoallergenic and/or impregnated with anti-bacterial properties. In some embodiments, the adhesive pad are designed to make the sensor waterproof by using a piece that surrounds a section of the ex vivo portion of the sensor that can be exposed to water. For example, in one embodiment, the adhesive pad includes a silicone O-ring that surrounds a portion of the sensor so that when the adhesive pad is adhered to the skin, a downward force holds the O-ring against the skin and provides a barrier against water entry that may occur from certain activities (e.g., swimming, showering, etc.). Although a silicone O-ring is described, it should be understood that the piece that surrounds the section of the ex vivo portion of the sensor can have any of a variety of shapes (e.g., a polygon) and any of a variety of materials. In another embodiment, a gel (e.g., a silicone gel), adhered on top of the adhesive pad and positioned around the sensor base, is used to provide a waterproof seal around the sensor.

The adhesive pad 204 may also comprise an absorbent layer or absorbents capable of absorbing water and moisture (e.g., sweat). Absorbent materials can include materials such as, but not limited to, a carboxylic acid-containing organic polymer, an amine-containing organic polymer (e.g., poly (quaternary amine), a polylactam, a polyamide), polyethylene terephthalate (PET), polypropylene (PP), or blends of viscose rayon and polyolefins, cellulose fiber, cotton, wool, combinations thereof, or other materials that are absorbent. In some embodiments, the absorbent material will absorb at least 50% of its weight, at least 80% of its weight, or at least 100% of its weight.

An undersurface 214 of the adhesive pad 204 includes an adhesive material, such that the adhesive pad 204 is configured to adhere to the host's skin. The adhesive material on the undersurface 214 of the adhesive pad 204 may comprise any adhesive material, including, but not limited to, any of those described herein, and/or any other material(s) not described herein. The adhesive pad 204 preferably has a slight thickness to enhance the wearability of the pad as well as to render it difficult to peel off the host's skin. For example, the adhesive pad 204 may have a thickness in the range of from about 0.05 mm to about 1 mm, preferably from about 0.1 mm to about 0.7 mm, and more preferably from about 0.2 mm to about 0.5 mm.

With reference to FIGS. 2 and 3, the adhesive sensor system 200 further comprises a reinforcing overlay 206 that at least partially covers the adhesive pad 204. FIG. 2 is a partially exploded view that illustrates the overlay 206 separately from the sensor electronics unit 202 and the adhesive pad 204, while FIG. 3 is an assembled view. With reference to FIG. 2, the overlay 206 is shaped substantially as a thin, flat, sheet and includes a central opening 216. The opening 216 is sized and shaped to accommodate the sensor electronics unit 202 so that the overlay 206 can be placed over the adhesive pad 204, as shown in FIG. 3. Although illustrated in FIG. 3 with a particular shape, the overlay may have any of a variety of shapes that include straight and/or curved lines. In some embodiments, the opening 216 has a shape that substantially corresponds to the shape of the electronics housing 208.

The overlay 206 comprises a sheet of flexible and resilient material. Example materials for the overlay 206 include, without limitation, polymers such as polyurethane film and an adhesive material on at least a portion of one or more sides of the polyurethane film. The polyurethane film can be a breathable material. In example embodiments, the adhesive pad 204 comprises spunlace and the overlay 206 comprises polyurethane.

The overlay 206 has a larger perimeter dimension than the adhesive pad 204, such that the overlay 206 extends outwardly on all sides from a periphery of the adhesive pad 204 when the overlay 206 is positioned over the adhesive pad 204, as shown in FIG. 3. It has been found that premature detachment of the adhesive pad is often caused by unintended contact (e.g. rubbing) with the adhesive pad's edge, which is typically the portion of the adhesive pad that is the first to peel off from the skin. It has also been found that greater adhesive pad thickness can result in a greater likelihood of contact, and thus greater likelihood of premature detachment.

To reduce this problem, in some embodiments, a portion of the overlay that comprises the perimeter edge of the overlay has a thickness that is less than that of the interior portion of the overlay. In some embodiments, the perimeter edge of the overlay has a thickness that is less than about 75% of the thickness of the interior portion of the overlay, preferably less than about 50%, and more preferably less than about 25%.

An upper surface 218 of the overlay 206 is non-adhesive, while an undersurface 220 of the overlay 206 includes an adhesive material, such that the overlay 206 is configured to adhere to the host's skin. The adhesive material may cover the entirety of the undersurface 220 of the overlay 206. Alternatively, the adhesive material may cover only a portion of the undersurface 220 of the overlay 206. For example, portions of the overlay 206 that abut the adhesive pad 204 in the assembled configuration of FIG. 3 may not include any adhesive material, such that the overlay 206 does not adhere directly to the adhesive pad 204. The adhesive material on the undersurface 220 of the overlay 206 may comprise any adhesive material, including any of those described herein, and/or any other material(s) not described herein. The overlay 206 preferably has a slight thickness to enhance the wearability of the adhesive sensor system 200 as well as to render it difficult to peel the overlay 206 off the host's skin. For example, the overlay 206 may have a thickness in the range of about 0.01 mm to about 0.1 mm, preferably from about 0.3 mm to about 0.8 mm, and more preferably from about 0.4 mm to about 0.6 mm. As the thickness of the overlay 206 decreases, it becomes more and more difficult to peel off the host's skin. Thus, the overlay 206 is preferably as thin as possible without compromising its ability to reinforce the adherence of the adhesive pad 204 to the host's skin.

In an alternative embodiment, instead of having an overlay 206 designed to adhere to the upper surface 210 of the adhesive pad 204, the overlay piece (or now more appropriately labeled the underlay) may be designed to be disposed under the adhesive pad 204 during use. The underside of the adhesive pad is then attached to the top surface of the underlay tape. In this embodiment, the underlay (not shown) may not need a central opening 216. This configuration has several possible advantages. The underside of the adhesive pad can be attached to the upper surface of the underlay. Since the underlay may be formed of a thermoplastic material, such as polyurethane, and the adhesive pad often uses a spun-lace thermoplastic acrylic-based adhesive, this design allows for strong bonding between similar materials. In other words, it leverages the benefits of stronger bond strengths between similar materials. Furthermore, if the underlay is comprised of a thin material, such as polyurethane, the thinner underlay creates a lower edge on the body which reduces mechanical friction or rubbing against the edge of the adhesive patch where most peel failures start. In addition, the underlay, which may be better at adhering to the skin than the adhesive pad, can provide an upper surface for the adhesive pad 204 to adhere to. Through this use, because of improved adherent properties of the underlay, the likelihood of premature detachment by the underlay may be reduced. Although in the embodiments described here, the overlay is applied on top of the adhesive, other configurations are also possible.

As illustrated in FIG. 3, a first portion 222 of the overlay 206 overlies the adhesive pad 204, and may adhere to the adhesive pad 204, and a second portion 224 of the overlay 206 lies radially outward of the adhesive pad 204 and may adhere to the skin of the host. In some embodiments, the first portion 222 may comprise from about 10% to about 75% of the total area of the overlay 206, and in further embodiments the first portion 222 may comprise from about 15% to about 55% of the total area of the overlay 206, preferably from about 20% to about 50%. In some embodiments, the adhesive pad 204 may have an area from about 1 square inch to about 2 square inches, such as about 1.6 square inches, and the overlay 206 may have an area from about 4 square inches to about 7 square inches, such as about 5.6 square inches.

The overlay 206 advantageously reinforces the adherence of the adhesive pad 204 to the host's skin. For example, in some embodiments, application of the overlay 206 onto the adhesive pad 204 results in an increased adhesive strength when measured according to average load and maximum load. Tests conducted by the inventors compared the average load and maximum load for a sample set of adhesive pads without reinforcing overlay versus a sample set of adhesive pads with reinforcing overlay.

For the control patches associated with FIG. 42A, the tests conducted involved the use of Instron 3345 Series Test System. During the test, an assembly comprising an adhesive pad and a sensor electronics unit housing attached thereto are secured to the clamps of the Instron 3345 Series Test System. Securement is achieved by having the clamps grasp the sensor electronics unit housing. Next, the backing layer of the adhesive pad is peeled off and removed. Thereafter, the clamps are lowered to a position (i.e., the initial position) that permits the adhesive pad to be applied and adhered onto a standard test panel (stainless steel panel). Next, the clamps are programmed to raise the assembly at a speed of 12 inches/min. As the clamps are raised, data is collected. The extension described in FIG. 42A corresponds to the distance moved by the clamps from its initial position. The program provided an output of the maximum and average load (lbf), which correspond to adhesive strength.

For the test patches (i.e., use of a control patch in conjunction with an overlay) associated with FIG. 42B, the tests conducted also used the Instron 3345 Series Test System. During the test, an assembly comprising an adhesive pad and a sensor electronics unit housing attached thereto are secured to the clamps of the Instron 3345 Series Test System. In addition, an overlay patch is disposed on top of the adhesive pad. Securement is achieved by having the clamps grasp the sensor electronics unit housing. Next, the backing layer of the adhesive pad is peeled off and removed. Thereafter, the clamps are lowered to a position (i.e., the initial position) that permits the adhesive pad to be applied and adhered onto a standard test panel (stainless steel panel). Thereafter, the backing of the overlay patch is removed, and the overlay patch is adhered both to a portion of the adhesive pad and a portion of the standard test panel. Next, the clamps are programmed to raise the assembly at a speed of 12 inches/min. As the clamps are raised, data is collected. The extension described in FIG. 42B corresponds to the distance moved by the clamps from its initial position. The program provided an output of the maximum and average load (lbf), which correspond to adhesive strength.

Test results, which are provided below and in FIGS. 42A and 42B, showed an increase in average load of about 42% and an increase in maximum load of about 17% for the sample set of adhesive pads with reinforcing overlay as compared to the sample set of adhesive pads without reinforcing overlay.

Both control patch and overlay patch samples were tested according to were tested with the method described above, as shown below in Table III. The control patches corresponding to P1 each comprise an adhesive pad and a sensor electronics unit housing attached thereto. Set P2, which used an overlay patch on a control patch, produced higher adhesive strength compared to Set P1 (control patch by itself). FIGS. 42A and 42B are plots of extension (inches) vs. load (lbf) generated by Instron BlueHill software. FIG. 42A illustrates extension vs. load for Set P1, while FIG. 42B illustrates extension vs. load for Set P2. As shown, there exists a clear difference in the adhesive strength profile between Sets P1 and P2. Both sets reach the maximum adhesive strength around 0.2" of extension and then start to decline. Set P1 continues to decline in adhesive strength value and finally gives way around 1.0". But in Set P2 the adhesive strength value is maintained from 0.4" to 0.9". From 0.9" the adhesive strength reduces in a step function-like pattern. The adhesive strength of Set P2 does not reach zero until 1.3". The statistical data analysis and adhesive strength profiles suggest that using the overlay patch on the control patch may yield extended adhesion of the control patch on skin as well as provide extra support on patch contact with user skin.

TABLE III

Test Set Description

| Set ID | Set Description | Sterilization | Test Qty. |
|---|---|---|---|
| P1 | Control Patch | Control Patches are sterilized | 30 |
| P2 | Control Patch + Overlay Patch | Control Patches are sterilized. Overlay Patches are NOT sterilized. | 30 |

TABLE IV

Avg and Max Adhesive strength (lbf)

| Set ID | Avg Adhesive strength (lbf) | Max Adhesive strength (lbf) | Test Qty |
|---|---|---|---|
| P1 | 3.935 +/− 0.447 | 10.504 +/− 1.013 | 30 |
| P2 | 5.570 +/− 0.277 | 12.311 +/− 0.682 | 30 |

Further, because the overlay 206 is a separate component from the sensor electronics unit 202 and the adhesive pad 204, the overlay 206 can be removed at any time and replaced with a fresh overlay 206 without disturbing the continued operation of the sensor electronics unit 202 and without removing the adhesive pad 204 from the host's skin. The overlay 206 can thus serve as an outer, replaceable, sacrificial layer that protects the underlying adhesive pad 204 and prolongs the lifespan of the adhesive pad 204.

In various embodiments, the shape of the central opening 216 in the overlay 206 may vary. For example, the opening 216 may be shaped to conform to the perimeter shape of any of a variety of different sensor electronics units. Also in various embodiments, the perimeter shape of the adhesive pad 204 and/or the overlay 206 may be a shape other than the illustrated oval shapes, such as circular, or any other polygonal shape. Also in various embodiments, the thickness of the overlay 206 may vary. For example, the overlay 206 may include a lesser thickness in the first portion 222 that directly overlies the adhesive pad 204, and a greater thickness in the second portion 224 that is positioned radially outward from the adhesive pad 204, so that the perimeter outline of the adhesive pad 204 is not visible through the overlay 206. However, in other embodiments, the second portion 224 of the overlay 206 may have a thickness less than that of the first portion 222, thereby providing a configuration that reduces the likelihood of premature detachment of the overlay 206, which typically peels off at the perimeter edge.

In various embodiments, the overlay 206 may be transparent or opaque. Also in various embodiments, the adhesive material on the underside 220 of the overlay 206 may be the same as the adhesive material on the underside 214 of the adhesive pad 204. Alternatively, the adhesive material on the underside 220 of the overlay 206 may be different from the adhesive material on the underside 214 of the adhesive pad 204. For example, the adhesive material on the underside 220 of the overlay 206 may have stronger or weaker adhesive properties from the adhesive material on the underside 214 of the adhesive pad 204.

Figure 4:
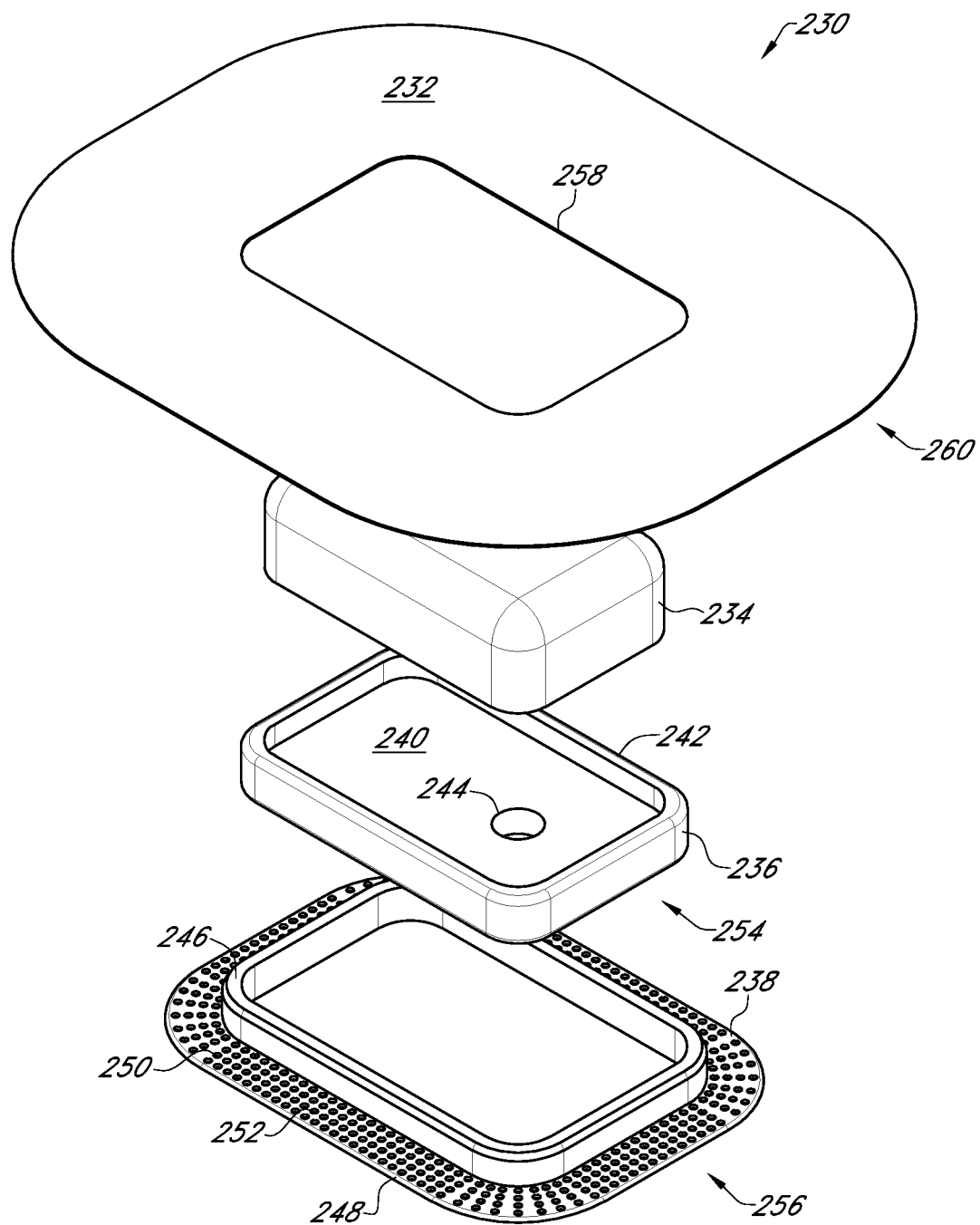
FIG. 4 is a partially exploded upper perspective view of another embodiment of an adhesive sensor system including a replaceable reinforcing overlay.
Figure 5:
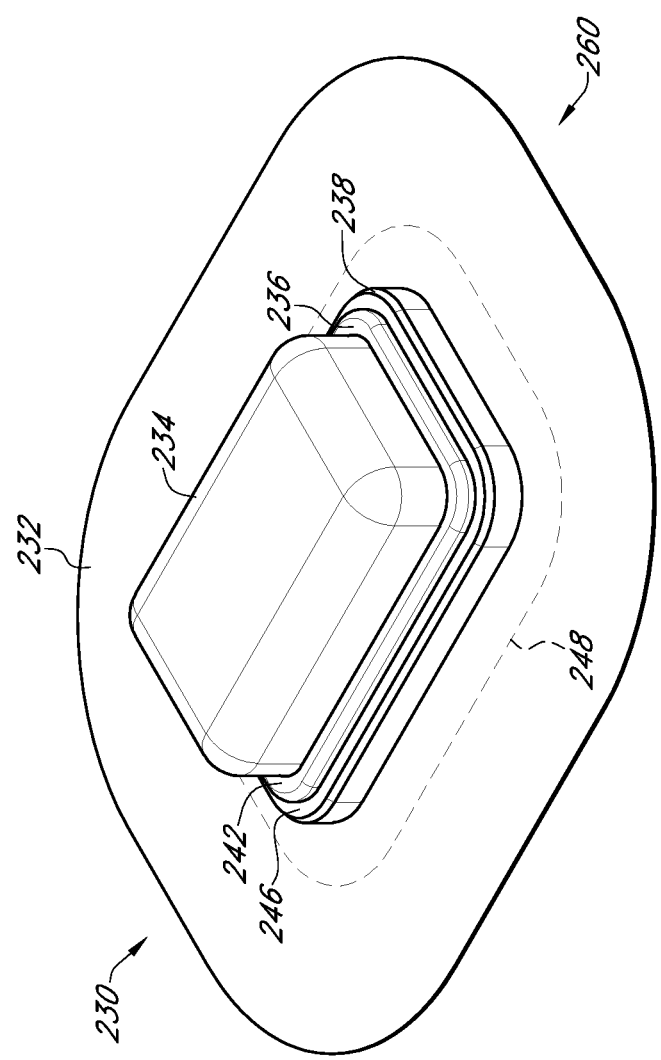
FIG. 5 is an assembled upper perspective view of the adhesive sensor system of FIG. 4.

FIGS. 4 and 5 illustrate another example embodiment of an adhesive sensor system 230 including a replaceable reinforcing overlay 232. The system 230 includes a sensor electronics unit 234, a sensor electronics unit housing 236 that receives the sensor electronics unit 234, a frame 238 that receives the housing 236, and a replaceable reinforcing overlay 232 that seats around the sensor electronics unit 234, the housing 236, and the frame 238, and partially covers the frame 238. FIG. 4 is an exploded view of the components of the system 230, while FIG. 5 is an assembled view.

With reference to FIG. 4, the housing 236 comprises a planar bottom wall 240 and a lip 242 that extends around the periphery of the bottom wall 240. The housing 236 is substantially rectangular in plan view to match the shape of the sensor electronics unit 234, but could be any shape in other embodiments. The bottom wall 240 includes an opening 244 to accommodate the sensor (not shown), which passes through the opening 244 so that a portion of the sensor extends into the host's skin. A height of the lip 242 is greater than a thickness of the bottom wall 240, such that the sensor electronics unit 234 seats within the housing 236 with the underside of the sensor electronics unit 234 abutting the upper face of the bottom wall 240 and the lip 242 extending around the outer edges of the sensor electronics unit 234, as shown in FIG. 5.

With further reference to FIG. 4, the frame 238 comprises a lip 246 that is sized and shaped to receive the housing 236 with the lip 246 extending around the outer edges of the housing 236, as shown in FIG. 5. With reference back to FIG. 4, the frame 238 further comprises a flange 248 that extends radially outward from a lower end of the lip 242. An upper surface 250 of the flange 248 includes texturing 252 that provides improved breathability. In the illustrated embodiment, the texturing 252 comprises a plurality of small apertures arranged substantially in a grid pattern. However, the illustrated configuration of the texturing 252 is just one example and is not limiting.

An undersurface 254 of the housing 236 and/or an undersurface 256 of the frame 238 may include an adhesive material to facilitate securing the adhesive sensor system 230 to the host's skin. The adhesive material may comprise any adhesive material, including any of those described herein, and/or any other material(s) not described herein. The housing 236 and/or the frame 238 may comprise various materials having desired properties, such as, without limitation, flexibility, rigidity, low density, etc. Example materials include, without limitation, polymers such as polycarbonate, polyester, and polyvinyl chloride.

With reference to FIGS. 4 and 5, the overlay 232 at least partially covers the flange 248 of the frame 238. The overlay 232 is shaped substantially as a thin, flat, sheet and includes a central opening 258. The opening 258 is sized and shaped to accommodate the sensor electronics unit 234, the housing 236, and the frame 238 so that the overlay 232 can be placed over the flange 248, as shown in FIG. 5.

The overlay 232 comprises a sheet of flexible and resilient material. Example materials for the overlay 232 include, without limitation, fabrics, polymers such as, for example, polyurethane, and other materials that can be formed into a very thin layer.

The overlay 232 has a larger perimeter dimension than the flange 248, such that the overlay 232 extends outwardly on all sides from a periphery of the flange 248, as shown in FIG. 5. An undersurface 260 of the overlay 232 includes an adhesive material, such that the overlay 232 is configured to adhere to the host's skin. The adhesive material may cover the entirety of the undersurface 260 of the overlay 232. Alternatively, the adhesive material may cover only a portion of the undersurface 260 of the overlay 232. For example, portions of the overlay 232 that abut the flange 248 in the assembled configuration of FIG. 5 may not include any adhesive material, such that the overlay 232 does not adhere directly to the flange 248. The adhesive material on the undersurface 260 of the overlay 232 may comprise any adhesive material, including any of those described herein, and/or any other material(s) not described herein. The overlay 232 preferably has a slight thickness to enhance the wearability of the adhesive sensor system 230 as well as to render it difficult to peel the overlay 232 off the host's skin. For example, the overlay 232 may have a thickness in the range of about 0.01 mm to about 0.1 mm, preferably from about 0.3 mm to about 0.8 mm, and more preferably from about 0.4 mm to about 0.6 mm. As the thickness of the overlay 206 decreases, it becomes more and more difficult to peel off the host's skin. Thus, the overlay 206 is preferably as thin as possible without compromising its ability to reinforce the adherence of the adhesive pad 204 to the host's skin.

The overlay 232 advantageously reinforces the adherence of the system 230 to the host's skin. Further, because the overlay 232 is a separate component from the sensor electronics unit 234, the housing 236, and the frame 238, the overlay 232 can be removed at any time and replaced with a fresh overlay 232 without disturbing the continued operation of the sensor electronics unit 234 and without removing any other components of the adhesive sensor system 230 from the host's skin. The overlay 232 can thus serve as an outer, replaceable, sacrificial layer that protects the other components and prolongs the lifespan of the system 230.

In various embodiments, the shape of the central opening 258 in the overlay 232 may vary. For example, the opening 258 may be shaped to conform to the perimeter shape of any of a variety of different sensor electronics units. Also in various embodiments, the perimeter shape of the flange 248 and/or the overlay 232 may be a shape other than the illustrated rectangular shapes, such as circular, or any other polygonal shape. Also in various embodiments, the thickness of the overlay 232 may vary. For example, the overlay 232 may include a lesser thickness in a portion that directly overlies the flange 248, and a greater thickness in portions that are positioned radially outward from the flange 248, so that the perimeter outline of the flange 248 is not visible through the overlay 232. In various embodiments, the overlay 232 may be transparent or opaque. Also in various embodiments, the adhesive material on the underside 260 of the overlay 232 may be the same as the adhesive material on the underside 254 of the housing 236 and/or the underside 256 of the frame 238. Alternatively, the adhesive material on the underside 260 of the overlay 232 may be different from the adhesive material on the underside 254 of the housing 236 and/or the underside 256 of the frame 238. For example, the adhesive material on the underside 260 of the overlay 232 may have stronger or weaker adhesive properties from the adhesive material on the underside 254 of the housing 236 and/or the underside 256 of the frame 238.

3. Island Placement

Another aspect of the present embodiments includes the realization that a thin adhesive pad that conforms to the contours of the host's skin provides advantages, but can also create discomfort for the host. For example, the sensor electronics unit typically includes a hard plastic outer housing. The thinner the adhesive pad is, the less able it is to provide a cushioning layer between the housing of the sensor electronics unit and the host's skin.

In recognition of the foregoing problem, as well as in recognition of any of the other problems discussed herein, some of the present embodiments provide a multilayer adhesive pad. In one embodiment, the adhesive pad system is configured to support a sensor assembly adhered thereon and is configured to resist pushing and pulling forces on the mass and volume of the sensor assembly. The adhesive pad system is also configured to maintain a sensor insertion for at least 14 days of ambulatory use.

In some embodiments, the multilayer adhesive pad may be configured to provide support and comfort to the patient from a hard plastic sensor electronics housing. The multilayer adhesive pad may comprise one or more layer(s) of spunlace (or another material) that provides a cushioning and comfortable layer that prevents or reduces abrasion of the electronics housing unit against the host's skin, and another layer of the adhesive pad may comprise polyurethane (or another material) to provide strong adhesion with a thin, skin-conforming layer.

Figure 6:
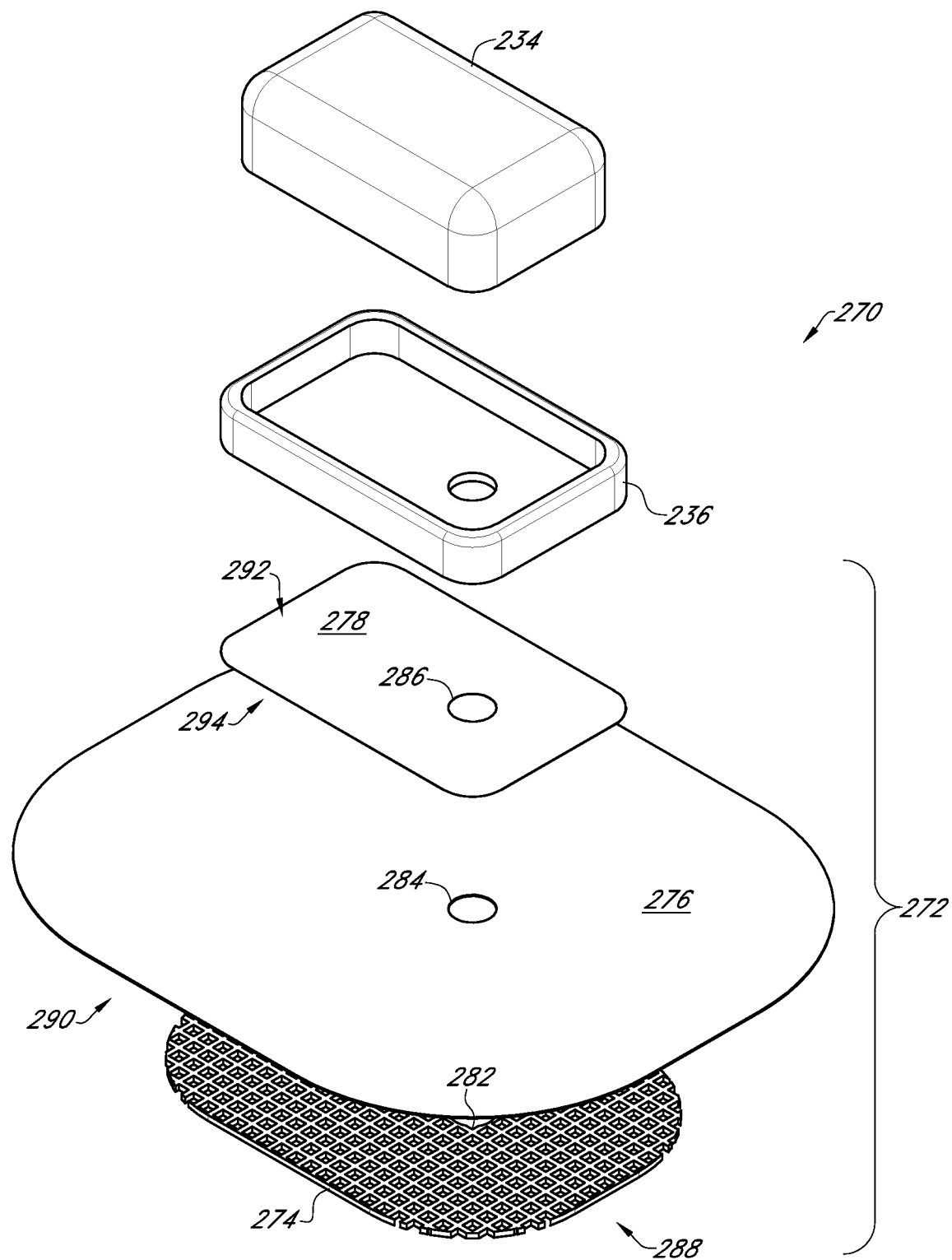
FIG. 6 is an exploded upper perspective view of one embodiment of an adhesive sensor system including a multilayer adhesive pad.
Figure 7:
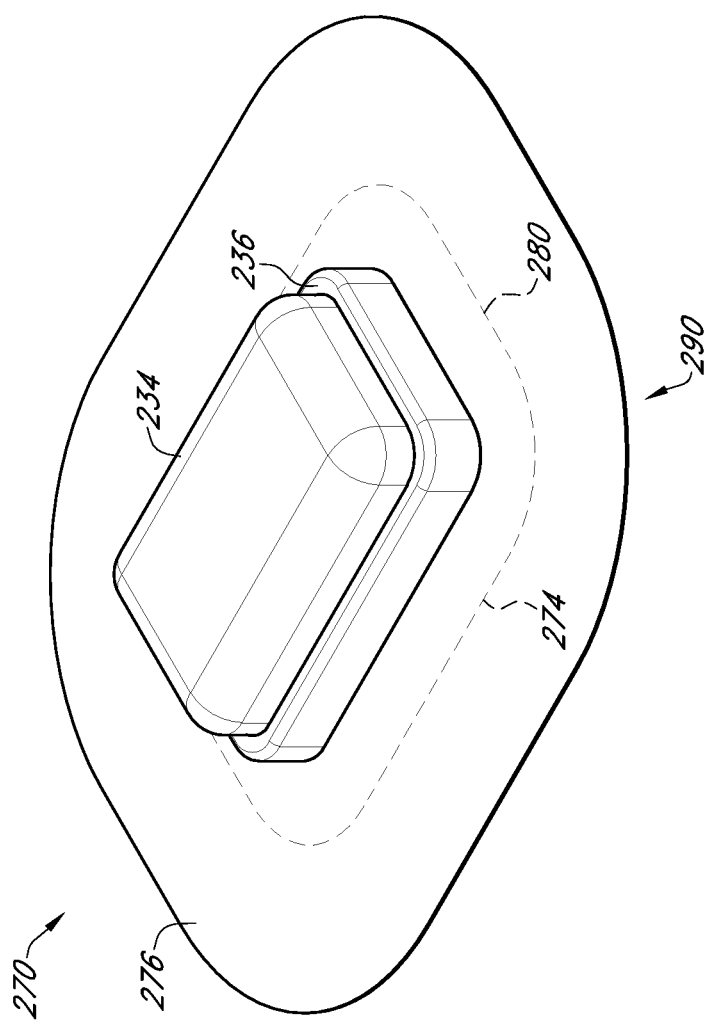
FIG. 7 is an assembled upper perspective view of the adhesive sensor system of FIG. 6.

FIGS. 6 and 7 illustrate one example embodiment of an adhesive sensor system 270 including a multilayer adhesive pad 272 (FIG. 6). The system 270 includes a sensor electronics unit 234, a sensor electronics unit housing 236 that receives the sensor electronics unit 234, a cushioning layer 274 that seats against the host's skin, an adhesive layer 276 that covers the cushioning layer 274, and a layer of double-sided tape 278 (FIG. 6) interposed between the adhesive layer 276 and the sensor electronics unit housing 236. FIG. 6 is an exploded view of the components of the system 270, while FIG. 7 is an assembled view.

With reference to FIG. 6, the sensor electronics unit housing 236 is similar to the sensor electronics unit housing 236 shown and described in preceding embodiments, and therefore will not be further described here. The cushioning layer 274, the adhesive layer 276, and the double-sided tape 278 each comprise a thin, flat, sheet of flexible and resilient material. All are substantially rectangular in plan view, but the illustrated shapes are merely examples and are not limiting. The adhesive layer 276 has a larger perimeter dimension than the cushioning layer 274, and extends outwardly on all sides from a periphery 280 of the cushioning layer 274, as shown in FIG. 7. With reference back to FIG. 6, the double-sided tape 278 has substantially the same size and shape as the sensor electronics unit housing 236 in plan view, and has a smaller perimeter dimension than both the adhesive layer 276 and the cushioning layer 274. The cushioning layer 274, the adhesive layer 276, and the double-sided tape 278 each include at least one opening 282, 284, 286, and the openings in each layer 274, 276, 278 align with one another when these layers are assembled as in FIG. 7. The sensor (not shown) passes through the aligned openings 282, 284, 286 so that a portion of the sensor extends into the host's skin.

The cushioning layer 274 preferably comprises a material that is comfortable to wear directly against skin, and that has sufficient thickness and resilience to provide cushioning between the sensor electronics unit housing 236 and the host's skin. Example materials for the cushioning layer 274 include, without limitation, spunlace (e.g. polyester spunlace), polymers such as polyurethane, fabrics such as non-woven fabrics, and other suitable materials. A thickness of the cushioning layer 274 may be, for example, in the range of 10-12 mils (1 mil=0.001 inches). With reference to FIG. 6, an undersurface 288 of the cushioning layer 274 may include an adhesive material, such that the cushioning layer 274 is configured to adhere to the host's skin. The adhesive material on the undersurface 288 of the cushioning layer 274 may comprise any adhesive material, including any of those described herein, and/or any other material(s) not described herein.

The adhesive layer 276 preferably comprises a material that provides strong adhesion to skin and that has sufficient resilience to closely conform to the contours of the host's skin. Example materials for the adhesive layer 276 include, without limitation, polymers such as polyurethane, fabrics such as non-woven fabrics, and other suitable materials. In example embodiments, the cushioning layer 274 comprises spunlace and the adhesive layer 276 comprises polyurethane. The adhesive layer 276 preferably has a slight thickness to enhance the wearability of the adhesive layer 276 as well as to render it difficult to peel off the host's skin. For example, the adhesive layer 276 may have a thickness in the range of 1-4 mils. An undersurface 290 of the adhesive layer 276 may include an adhesive material, such that the adhesive layer 276 is configured to adhere to the host's skin. The adhesive material on the undersurface 290 of the adhesive layer 276 may comprise any adhesive material, including any of those described herein, and/or any other material(s) not described herein. Example materials for the double-sided tape 278 include 3M® 1567 High Adhesion Double Coated Polyester Medical Tape, and MacTac® TM9720 High Adhesion Double Coated Polyester Medical Tape.

With reference to FIG. 6, opposite facing surfaces 292, 294 of the double-sided tape 278 include an adhesive material, such that the double-sided tape 278 assists in securing the sensor electronics unit housing 236 to the adhesive layer 276. The adhesive material of the double-sided tape 278 may comprise any adhesive material, including any of those described herein, and/or any other material(s) not described herein. The opposite facing surfaces 292, 294 of the double-sided tape 278 may include the same adhesive material, or different adhesive materials. In some embodiments, a spunlace pad having adhesive material on opposite surfaces may be substituted for the double-sided tape 278.

The adhesive sensor system 270 described above and shown in FIGS. 6 and 7 advantageously combines the cushioning layer 274 with the adhesive layer 276. The cushioning layer 274 seats directly against the host's skin and provides a comfortable interface between the host and the sensor electronics unit housing 236, which typically comprises hard plastic. The adhesive layer 276 covers the cushioning layer 274 and provides strong adhesion to the host's skin and also conformity with the skin. The adhesive layer 276 in some embodiments is very thin compared to the cushioning layer 274 and therefore more difficult to peel off from the skin.

Figure 8:
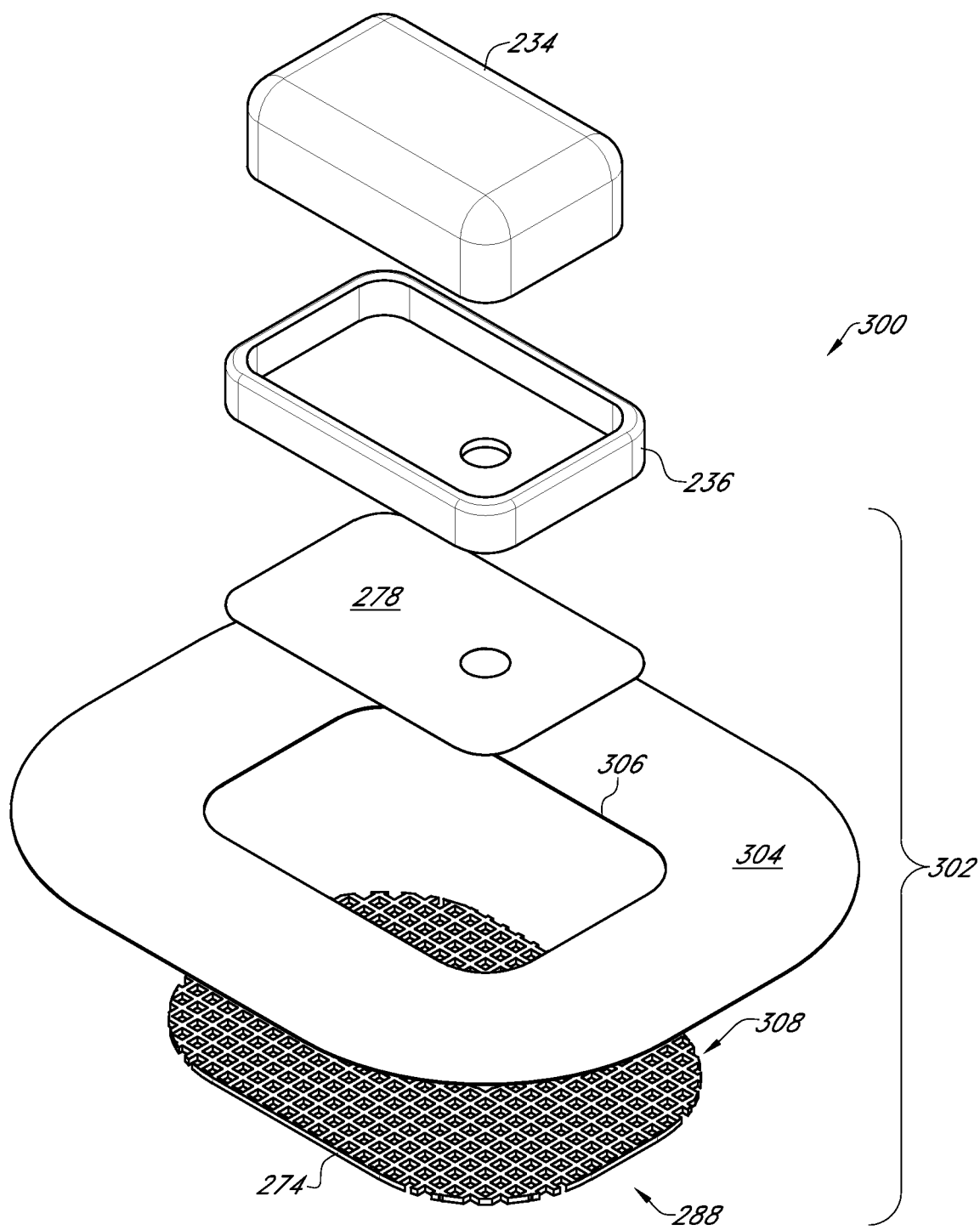
FIG. 8 is an exploded upper perspective view of another embodiment of an adhesive sensor system including a multilayer adhesive pad.
Figure 9:
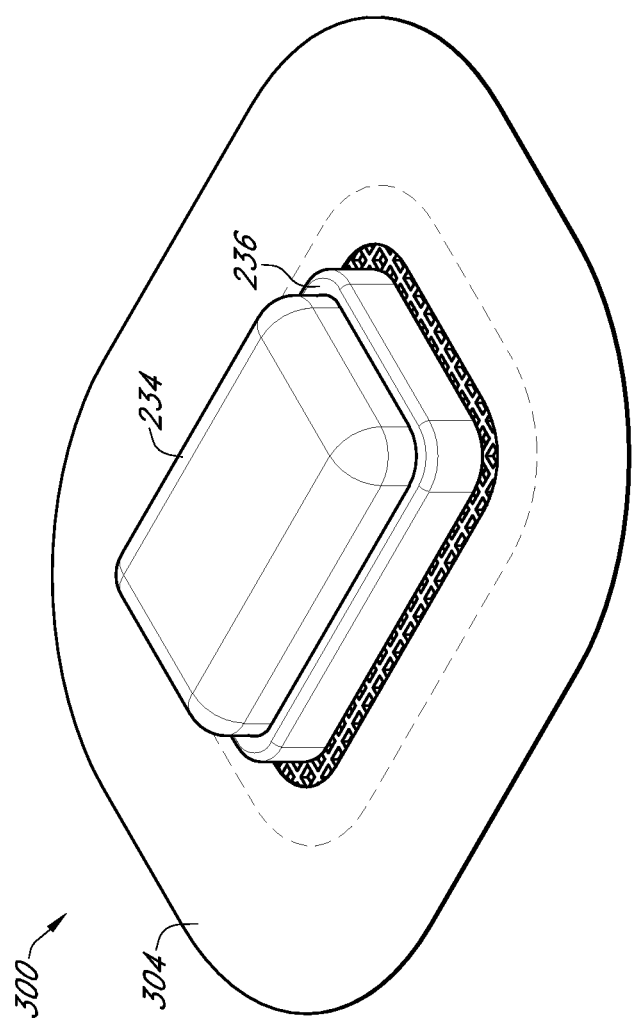
FIG. 9 is an assembled upper perspective view of the adhesive sensor system of FIG. 8.

FIGS. 8 and 9 illustrate another example embodiment of an adhesive sensor system 300 including a multilayer adhesive pad 302 (FIG. 8). The system 300 of FIGS. 8 and 9 is similar to the system 270 of FIGS. 6 and 7, except for the configuration of the adhesive layer 304. With reference to FIG. 8, the adhesive layer 304 includes a central opening 306 that is substantially the same size and shape as the double-sided tape 278. The double-sided tape 278 thus directly abuts and adheres to the cushioning layer 274, rather than the adhesive layer 304. This configuration provides added breathability (gas permeability) through the central opening 306 in the adhesive layer 304, which can help to reduce moisture buildup between the sensor electronics unit 234 and the host's skin.

In variations of the embodiments of FIGS. 6-9, the double-sided tape 278 may be omitted. In such variations, the sensor electronics unit housing 236 can be secured to the adhesive layer 276 (FIGS. 6 and 7) or the cushioning layer 274 (FIGS. 8 and 9) through any of a variety of techniques, including, for example, transfer adhesive, heat-staking, ultrasonic welding, and others. In the embodiment of FIGS. 8 and 9, the cushioning layer 274, which may be a spunlace pad, may have adhesive material on both opposite surfaces 288, 308 for securing the cushioning layer 274 to the host's skin and for securing the sensor electronics unit housing 236 to the cushioning layer 274.

Figure 45:
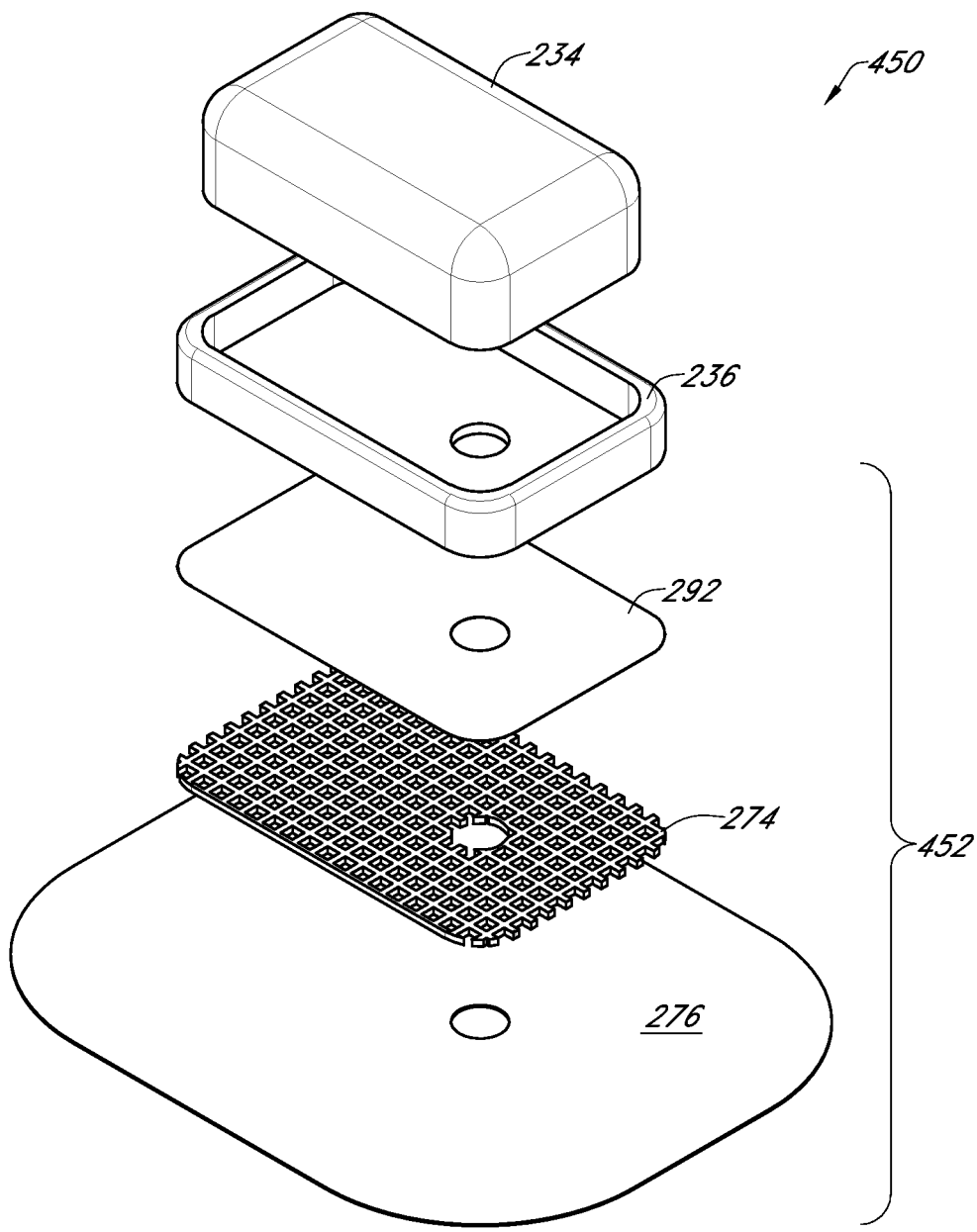
FIG. 45 is an exploded upper perspective view of another embodiment of an adhesive sensor system including a multilayer adhesive pad.

FIG. 45 illustrates yet another example embodiment of an adhesive sensor system 450 including a multilayer adhesive pad 452. The system 450 of FIG. 45 is similar to the system 270 of FIG. 6, with a difference in the position of the adhesive layer 276 relative to the cushioning layer 274. With the system 450 illustrated in FIG. 45, the adhesive layer 276 is positioned below the cushioning layer 274. The double-sided tape 292 directly adheres to the cushioning layer 274, rather than the adhesive layer 276.

In other embodiments, the double-sided tape 292 shown in FIG. 45 may be omitted. In such variations, the sensor electronics unit housing 236 configured to receive the electronics unit 234 can be secured to the adhesive layer 276 and/or the cushioning layer 274 through any of a variety of techniques, including, for example, transfer adhesive, heat-staking, ultrasonic welding, and other techniques. In one embodiment, the cushioning layer 274, which may be a spunlace pad, may have adhesive material on one or both opposite surfaces for securing the cushioning layer 274 to the adhesive layer 276 and for securing the sensor electronics unit housing 236 to the cushioning layer 274.

Figure 46A:
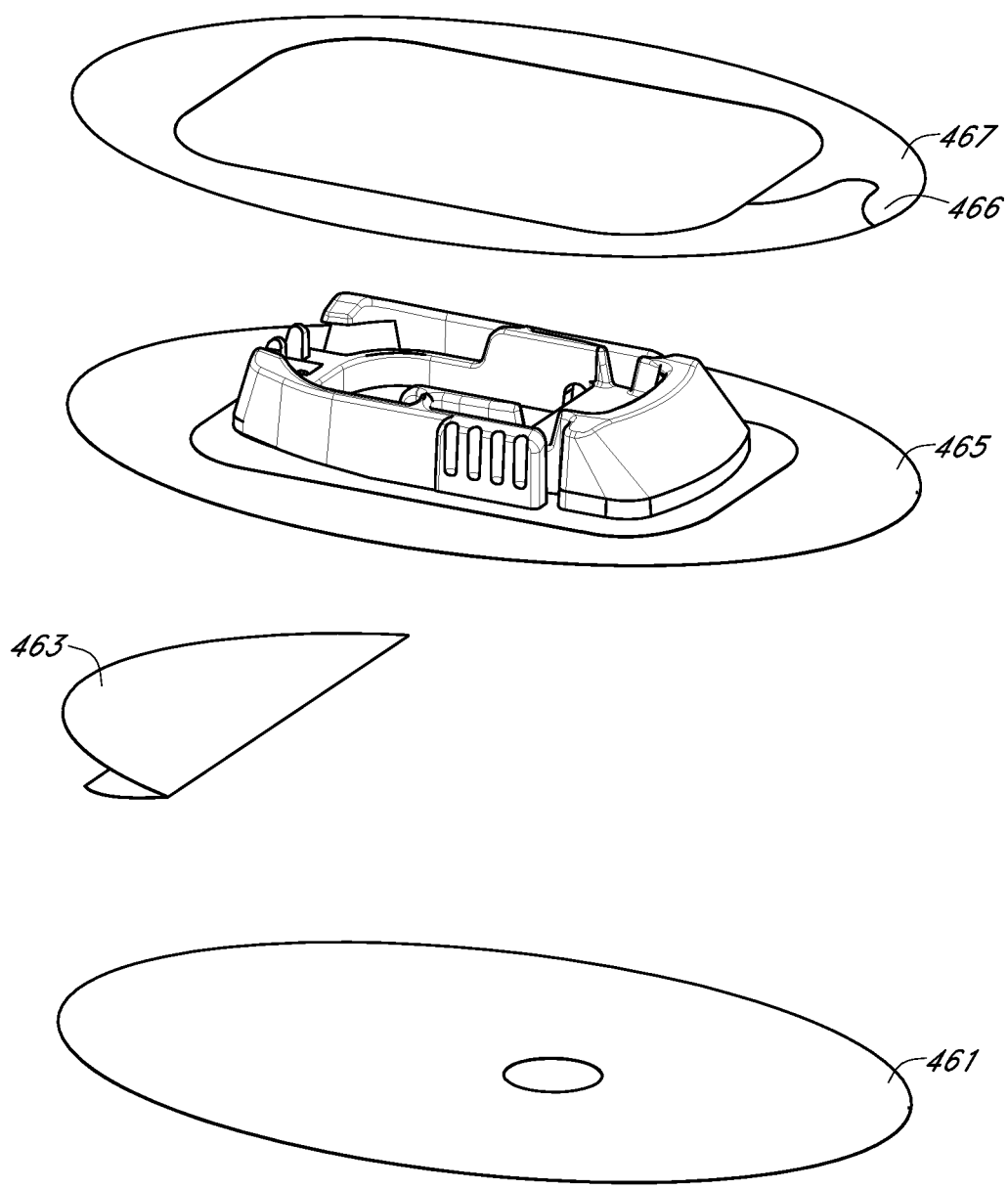
FIG. 46A is an exploded upper perspective view of an assembly comprising an adhesive sensor system and a liner system.
Figure 46B:
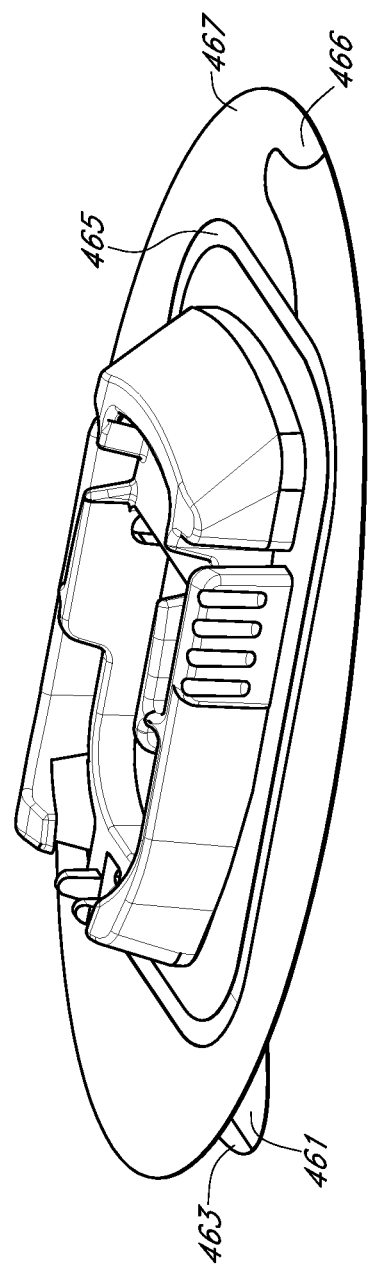
FIG. 46B is an assembled upper perspective view of the assembly illustrated in FIG. 46A.
Figure 46C:
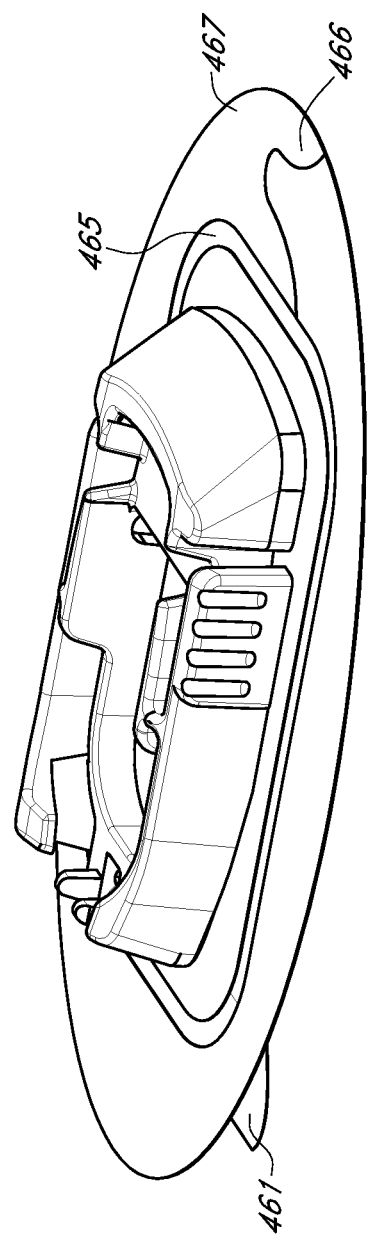
FIG. 46C is an assembled upper perspective view of the assembly illustrated in FIG. 46B after a first bottom liner has been removed.
Figure 46D:
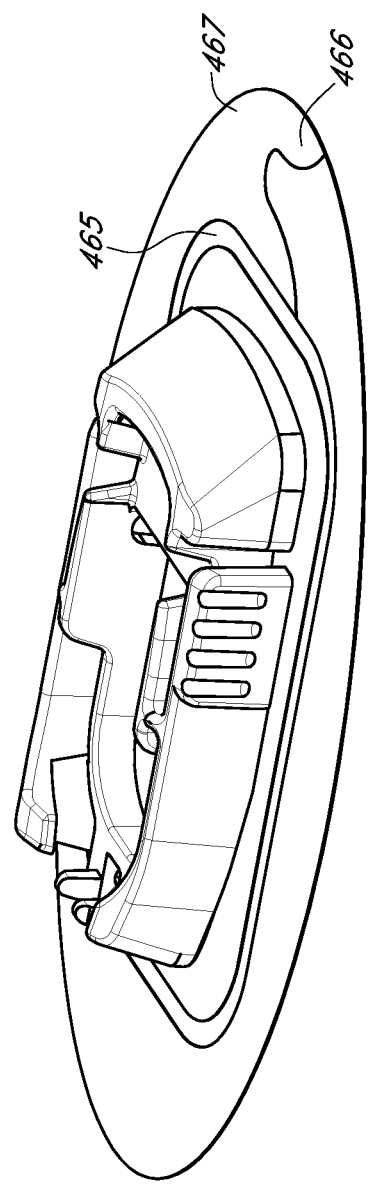
FIG. 46D is an assembled upper perspective view of the assembly illustrated in FIG. 46C after a second bottom liner has been removed.
Figure 46E:
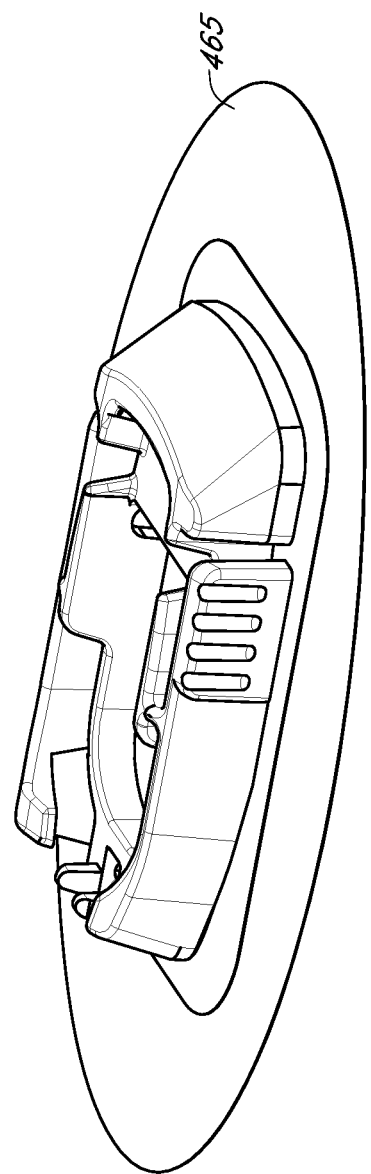
FIG. 46E is an assembled upper perspective view of the assembly illustrated in FIG. 46B after all the liners have been removed.

FIGS. 46A-46E illustrate an example embodiment of an adhesive sensor system 465 along with a liner system that covers a portion of the adhesive sensor system 465 prior to use. The adhesive sensor system may any described herein, including, but not limited to those illustrated in FIGS. 6-9, 44A, and 45. In this particular embodiment, the liner system comprises an upper liner 467, a bottom folded liner 463, and a bottom covering liner 461. FIG. 46A provides an exploded perspective view of the overall assembly comprising the adhesive sensor system 465 and the liner system, and FIG. 46B provides an assembled perspective of the assembly of FIG. 46A. With reference to FIGS. 46B and 46C, during use the user first peels off the bottom folded liner 463. The bottom folded liner only covers a portion of the bottom surface of the adhesive sensor system 465. Its presence separates a portion of the bottom covering liner 461 from the bottom surface of the adhesive sensor system 465, thereby making it easier for the user to peel off the bottom covering liner 461, which has a circumference and surface area that substantially covers the bottom surface of the adhesive sensor system 465. FIG. 46B illustrates the assembly prior to the bottom folded liner 463 being peeled off, and FIG. 46C illustrates the assembly after the bottom folded liner 463 has been peeled. After the bottom folded liner 463 has been peeled off, the user can easily grasp the portion of the bottom covering liner 461 separated from the bottom surface of the sensor adhesive system and remove the bottom covering liner 461 from the bottom surface of the sensor adhesive system 465. FIG. 46D illustrates the assembly after the bottom covering liner 461 has been peeled off. Next, the user applies the adhesive sensor system 465 to the skin. Afterwards, the user grasps the portion of the upper liner's peel tab 466 that was earlier bent back, and slowly removes the upper liner 467 from adhesive sensor system 465, which then remains adhered to the user's skin. The peel tab on the liner can be formed from any of a variety of methods and have any of a variety of configurations. For example, in one embodiment, the peel tab is formed from a cut-out or a perforated line or curve formed on the liner. FIG. 46E illustrates the assembly after all the liners have been peeled off, leaving only the adhesive sensor system 465.

Although in the embodiment shown in FIGS. 46A-46E, the liner system comprises three liners, with two bottom liners and one upper liner, it should be understood that any combination of liners can be used. For example, in one embodiment, the liner system can comprise one upper liner and one bottom liner. In another embodiment, the liner system can comprise two upper liners (e.g., one that is folded and the other full) and one bottom liner. In yet another embodiment, the liner system can comprise two upper liners and two bottom liners. It should also be understood that the peel tab illustrated in FIGS. 46A-D can be used in any liner. For example, it can be used as an upper liner or a bottom liner.

Figure 10:
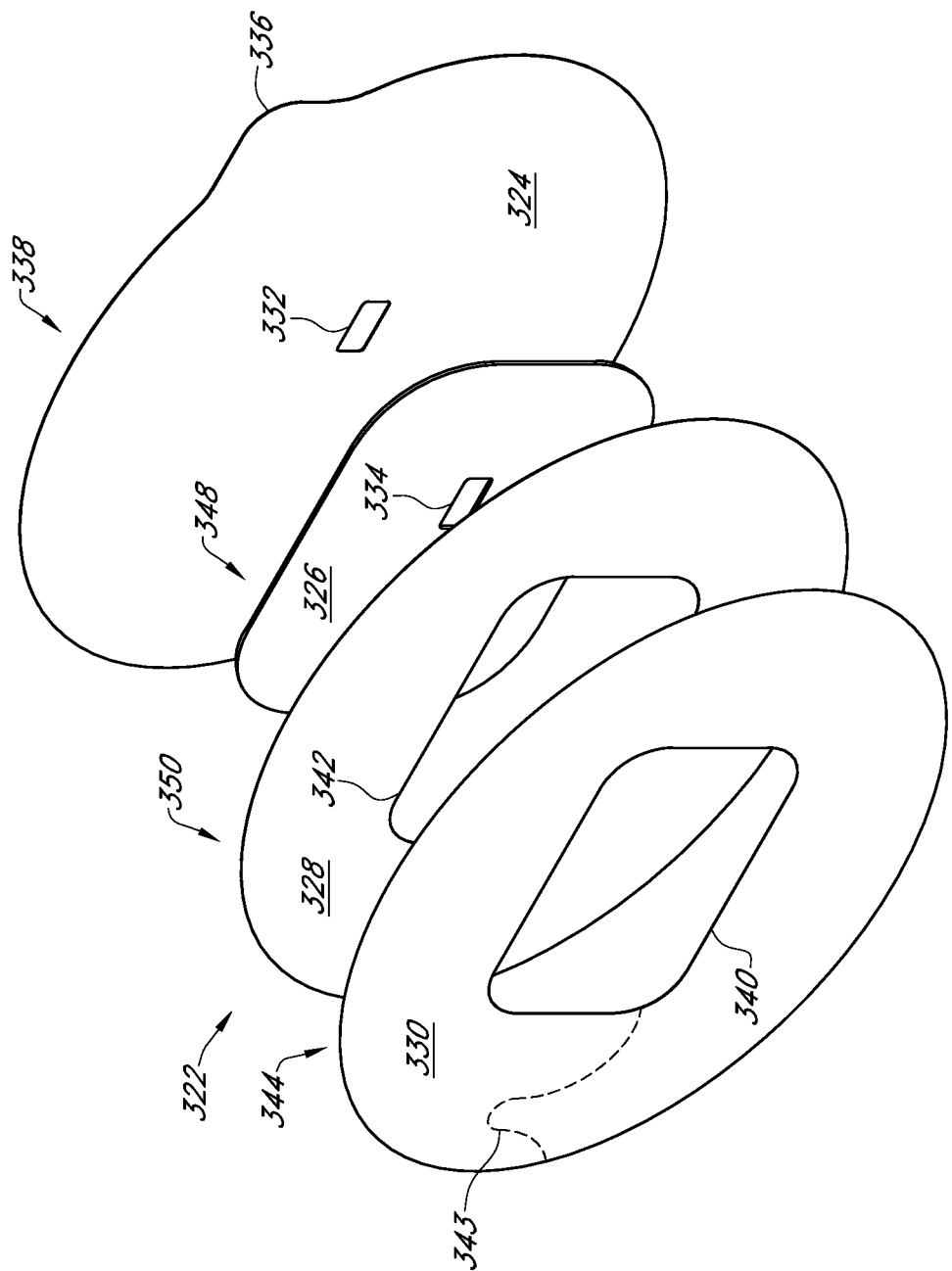
FIG. 10 is an exploded upper perspective view of another embodiment of a multilayer adhesive pad for an adhesive sensor system.
Figure 11:
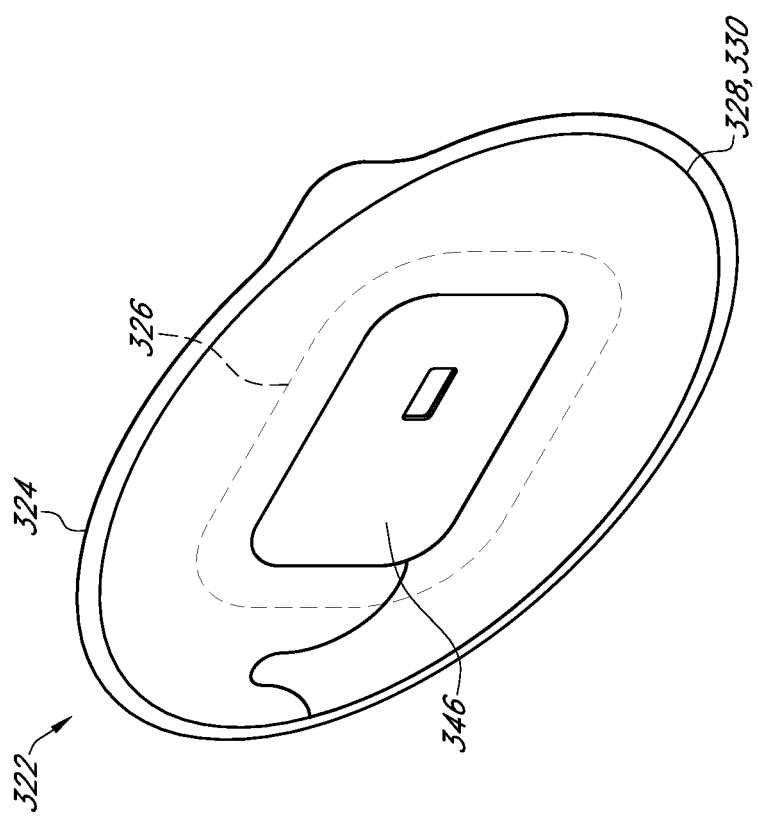
FIG. 11 is an assembled upper perspective view of the multilayer adhesive pad of FIG. 10.

FIGS. 10-13 illustrate another example embodiment of an adhesive sensor system 320 (FIGS. 12-13) including a multilayer adhesive pad 322. FIG. 10 is an exploded view of the layers of the adhesive pad 322, while FIG. 11 is an assembled view. With reference to FIG. 10, the multilayer adhesive pad 322 includes an inner liner 324, a cushioning layer 326, a reinforcing overlay 328, and an outer liner 330. The cushioning layer 326 and the reinforcing overlay 328 may be similar to the corresponding components described above with respect to the previous embodiments. Therefore, only those characteristics of the cushioning layer 326 and/or the reinforcing overlay 328 that vary from the previous embodiments will be described below.

With continued reference to FIG. 10, the inner liner 324 is a thin, flat, sheet of flexible and resilient material. The inner liner 324 is preferably thin and coated with silicone (or other material with similar properties) on one side only in order to provide easy separation from the patch. Example materials for the inner liner 324 include, without limitation, 3.2 mils siliconized release liner. The inner liner 324 includes an opening 332 that aligns with the opening 334 in the cushioning layer 326 to accommodate the sensor (not shown) so that a portion of the sensor extends into the host's skin. In the illustrated embodiment, the inner liner 324 is shaped substantially as an oval in plan view, but the illustrated shape is just one non-limiting example. An edge of the inner liner 324 includes a protruding tab 336 that provides a convenient location for the host to grasp the inner liner 324 when peeling the adhesive pad 322 off of his or her skin.

An undersurface 338 of the inner liner 324 may include an adhesive material to facilitate securing the adhesive sensor system 320 to the host's skin. The adhesive material may comprise any adhesive material, including any of those described herein, and/or any other material(s) not described herein.

With continued reference to FIG. 10, the outer liner 330 is a thin, flat, sheet of flexible and resilient material. The outer liner 330 is preferably thin and coated with silicone (or other material with similar properties) on one side only in order to provide easy separation from the patch. Example materials for the outer liner 330 include, without limitation, white poly-coated paper carrier having silicone (or other material with similar properties) on one side (4.8 mils/0.12 mm). The outer liner 330 includes a central opening 340 that aligns with the opening 342 in the overlay 328 to accommodate the sensor and to expose a portion of the cushioning layer 326 so that the sensor electronics unit housing (described with respect to subsequent figures) can be secured directly to the cushioning layer 326, as described below. In the illustrated embodiment, the outer liner 330 is shaped substantially as an oval in plan view, but the illustrated shape is just one non-limiting example. The dashed line 343 indicates the location of a peel tab on a backing (not shown) that covers the upper surface of the outer liner 330. Removal of the peel tab 343 from the backing is described below with reference to FIGS. 41A-D, which illustrate one example of a method for securing the outer liner 330 to skin of a wearer.

An undersurface 344 of the outer liner 330 may include an adhesive material to facilitate securing the outer liner 330 to the other layers of the multilayer adhesive pad 322. The adhesive material may comprise any adhesive material, including any of those described herein, and/or any other material(s) not described herein.

With reference to FIGS. 10 and 11, the shapes and sizes of the perimeters of the outer liner 330 and the overlay 328 are substantially identical. Similarly, the inner liner 324 has a perimeter shape that is substantially identical to that of the outer liner 330 and the overlay 328, but slightly larger, as shown in the assembled view of FIG. 11. The inner liner 324 thus extends outwardly on all sides from a periphery of the outer liner 330 and the overlay 328, as shown in FIG. 11. This feature advantageously protects the edge of the overlay 328 from potential damage from handling.

With reference to FIGS. 10 and 11, the outer liner 330 and the overlay 328 have substantially identical shapes and sizes. A shape of the central openings 340, 342 in the overlay 328 and the outer liner 330 is substantially identical to, but smaller than, the perimeter shape of the cushioning layer 326. Thus, when the layers 324, 326, 328, 330 of the multilayer adhesive pad 322 are secured to one another, as shown in FIG. 11, the outer liner 330 and the overlay 328 overlap the edges of the cushioning layer 326 and leave a central portion 346 of the cushioning layer 326 exposed. As described below, the sensor electronics unit housing is secured to the exposed portion 346 of the cushioning layer 326.

Figure 12:
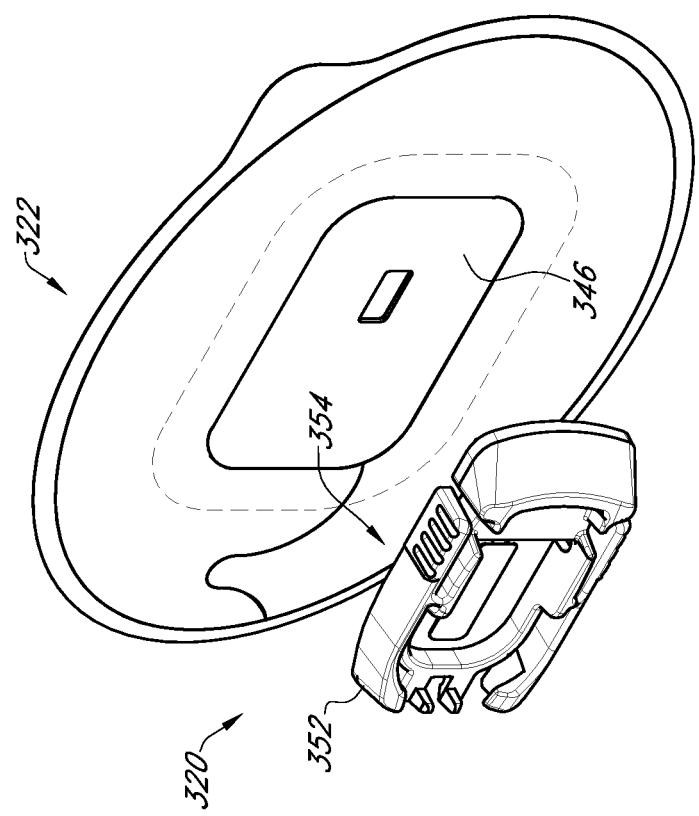
FIG. 12 is a partially exploded upper perspective view of the multilayer adhesive pad of FIG. 11 and a housing for a sensor electronics unit.
Figure 13:
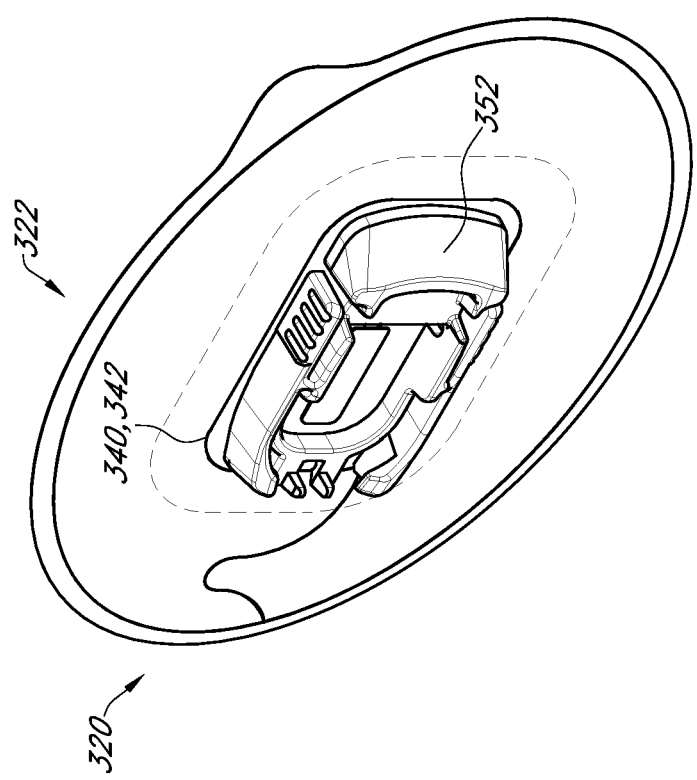
FIG. 13 is an assembled upper perspective view of the multilayer adhesive pad and the housing of FIG. 12.

When all the layers 324, 326, 328, 330 of the multilayer adhesive pad 322 are assembled, as shown in FIG. 11, the adhesive material on the undersurface 348 (FIG. 10) of the cushioning layer 326 secures the cushioning layer 326 to the inner liner 324. Similarly, the adhesive material on the undersurface 350 (FIG. 10) of the overlay 328 secures the overlay 328 to the cushioning layer 326 and to the inner liner 324, and the adhesive material on the undersurface 344 (FIG. 10) of the outer liner 330 secures the outer liner 330 to the overlay 328. With reference to FIGS. 12 and 13, the sensor electronics unit housing 352 is secured to the exposed portion 346 of the cushioning layer 326. FIG. 12 is a partially exploded view that illustrates the sensor electronics unit housing 352 separately from the multilayer adhesive pad 322, while FIG. 13 is an assembled view.

With reference to FIG. 13, a footprint of the sensor electronics unit housing 352 is sized to fit within the central openings 340, 342 of the outer liner 330 and the overlay 328, such that the undersurface 354 (FIG. 12) of the sensor electronics unit housing 352 directly abuts only the cushioning layer 326. The undersurface 354 of the housing 352 may be secured to the cushioning layer 326 using a variety of different techniques. For example, the housing 352 may be secured to the cushioning layer 326 through heat staking Features on the sensor electronics unit housing 352 can be added to facilitate the bonding method; for example, energy director ridges can be placed at the sites of welding (e.g., ultrasonic welding) or an additional bonding layer can be used to facilitate thermal bonding. During heat staking, a combination of applied conditions (e.g. heat, pressure, and time) are used to melt thermoplastic energy directors to then form a bond to another component upon cooling. To bond a pad to a sensor electronics unit housing, the housing and pad are placed on top of each other. Heat and pressure are then applied for a specified amount of time, melting the housing's energy directors and causing the melted thermoplastic to flow around and among the pad material. When cooled, the housing and pad are bonded together. In another embodiment, bonding of the housing to the adhesive pad is performed by gluing. In still other embodiments, sonic welding (e.g. using high frequency vibration to cause melting), double sided tape, or mechanical methods such as, for example, use of small hooks or hook-and-loop material. Uses of the above-described techniques for bonding the housing to the adhesive pad are not limited to the embodiment illustrated in FIG. 13, but may be employed in any of the embodiments described herein.

The inner liner 324 may be designed to protect the adhesive on the pads 326, 328. In some embodiments, the pad 328 has an extremely thin thickness, such that it has very low rigidity. In such embodiments, without the outer liner 330, the pad 328 would wrinkle up and stick to itself once the liner 324 is removed. Wrinkling of the pad 328 can result in early peel-off and/or premature detachment of the adhesive pad from the skin. As described elsewhere herein, early peel-off of the adhesive pad can be problematic even before the adhesive pad completely detaches from the skin. When the adhesion between the adhesive pad and the skin becomes weak and not sufficiently stable, the electronics housing and the sensor in contact therewith may become susceptible to undesired shaking and movement. Movement at the ex vivo portion of the sensor that contacts the electronics housing can translate across the length of the sensor to the in vivo portion of the sensor and cause complications and undesired effects. For example, movement translated to the in vivo portion of the sensor and cause complications, such as, irritation and inflammation, for example. In turn, these conditions can cause various forms of wound healing response from the patient's body, all of which can result in sensor inaccuracy, sensor failure, and/or shortened sensor life. To overcome this problem, an outer liner 330 may be provided to lend additional support to the pad 328.

Figure 41A:
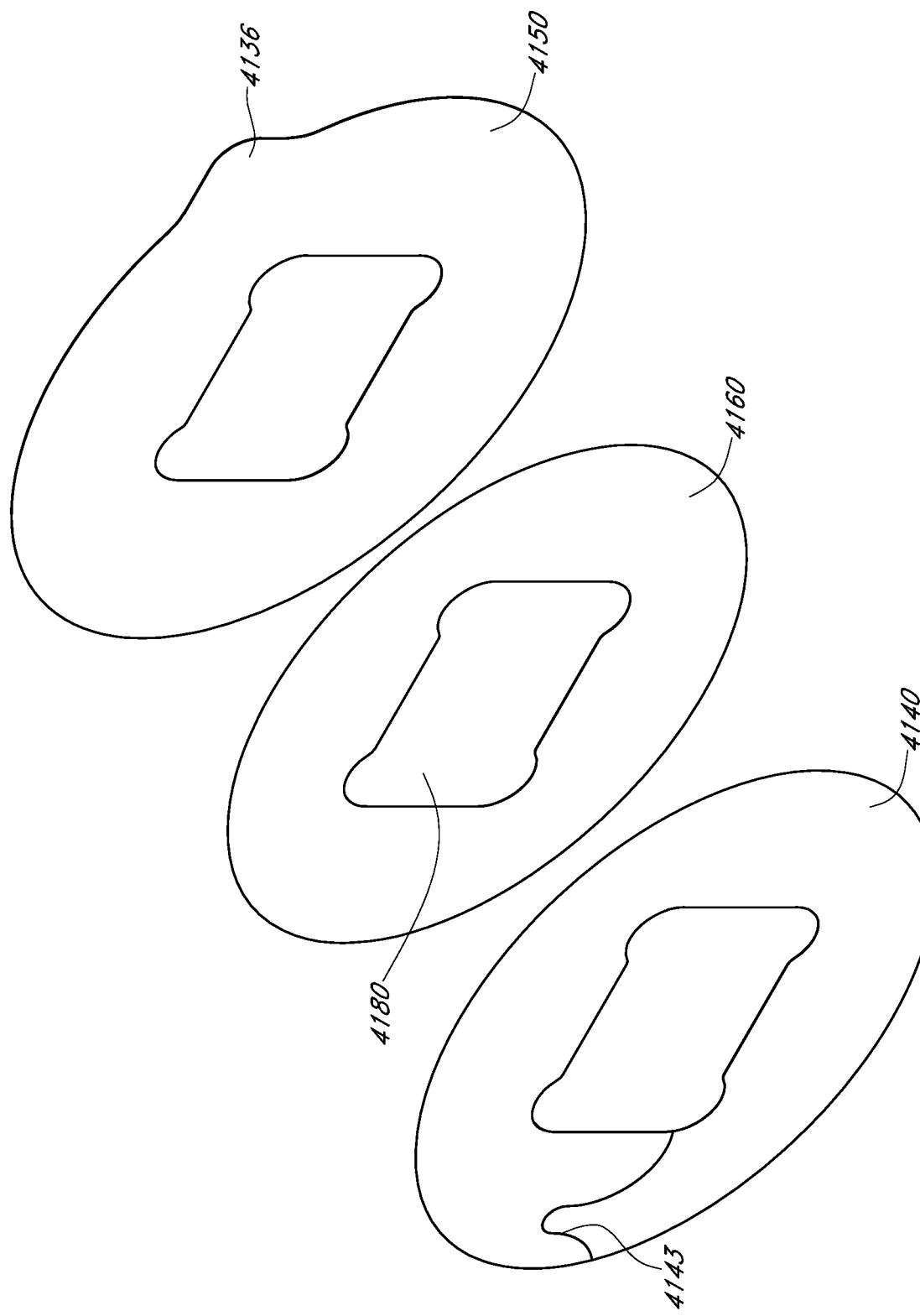
FIG. 41A is an exploded perspective view of the overlay assembly.
Figure 41B:
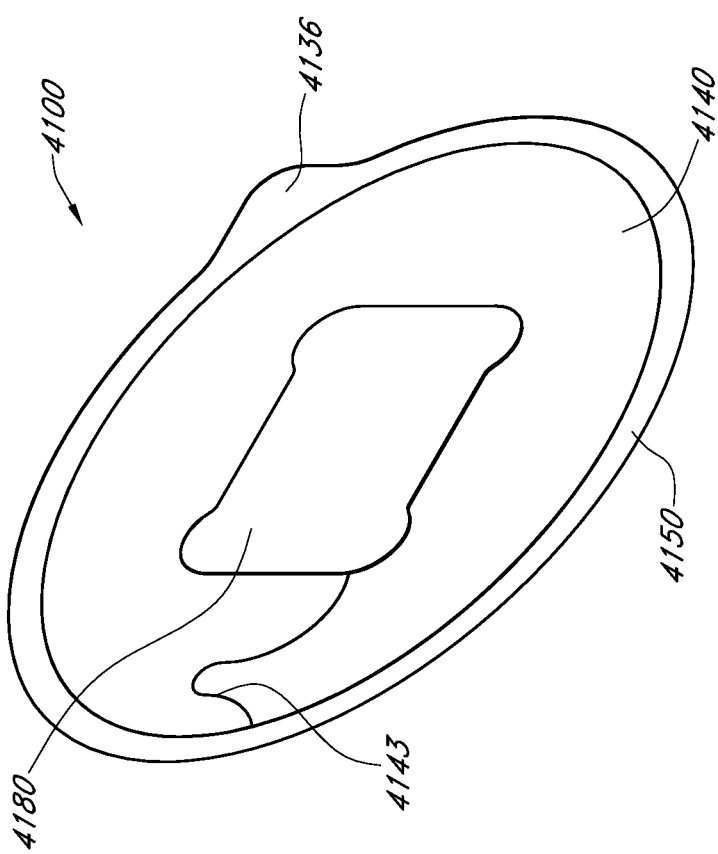
FIG. 41B is an assembled perspective of the overlay assembly of FIG. 41A.

FIGS. 41C1-C4 illustrate steps in one example of a method for applying an overlay 4160 over an adhesive pad with a sensor electronics unit housing affixed thereto 4152. The user is provided with an overlay assembly 4100 comprising an overlay 4160 covered on a first side by an upper liner 4140 and on a second side by a bottom liner 4150. FIG. 41A provides an exploded perspective view of the overlay assembly, and FIG. 41B provides an assembled perspective of the overlay assembly of FIG. 41A. The overlay 4160 comprises a central opening 4180 in its interior. With reference to FIG. 41C1, the user bends back the peel tab 4143 formed on the upper liner 4140. With reference to FIG. 41C2, the user next grasps the protruding tab 4136 on the bottom liner 4150 and removes the bottom liner 4150 from the remaining portions of the overlay assembly. With reference to FIG. 41C3, the user next places the remaining portions of the overlay assembly, which now includes the upper liner 4140 and the overlay 4160, around the sensor electronics unit housing 4152, such that the central opening 4180 of the overlay 4160 surrounds the sensor electronics unit housing 4152. The user preferably presses down firmly on the upper liner 4140 to securely adhere the overlay 4160 to the skin. With reference to FIG. 41C4, the user grasps the portion of the upper liner's 4140 peel tab 4143 that was earlier bent back, and slowly removes the upper liner 4140 from the overlay 4160, which then remains adhered to the user's skin.

Figure 14A:
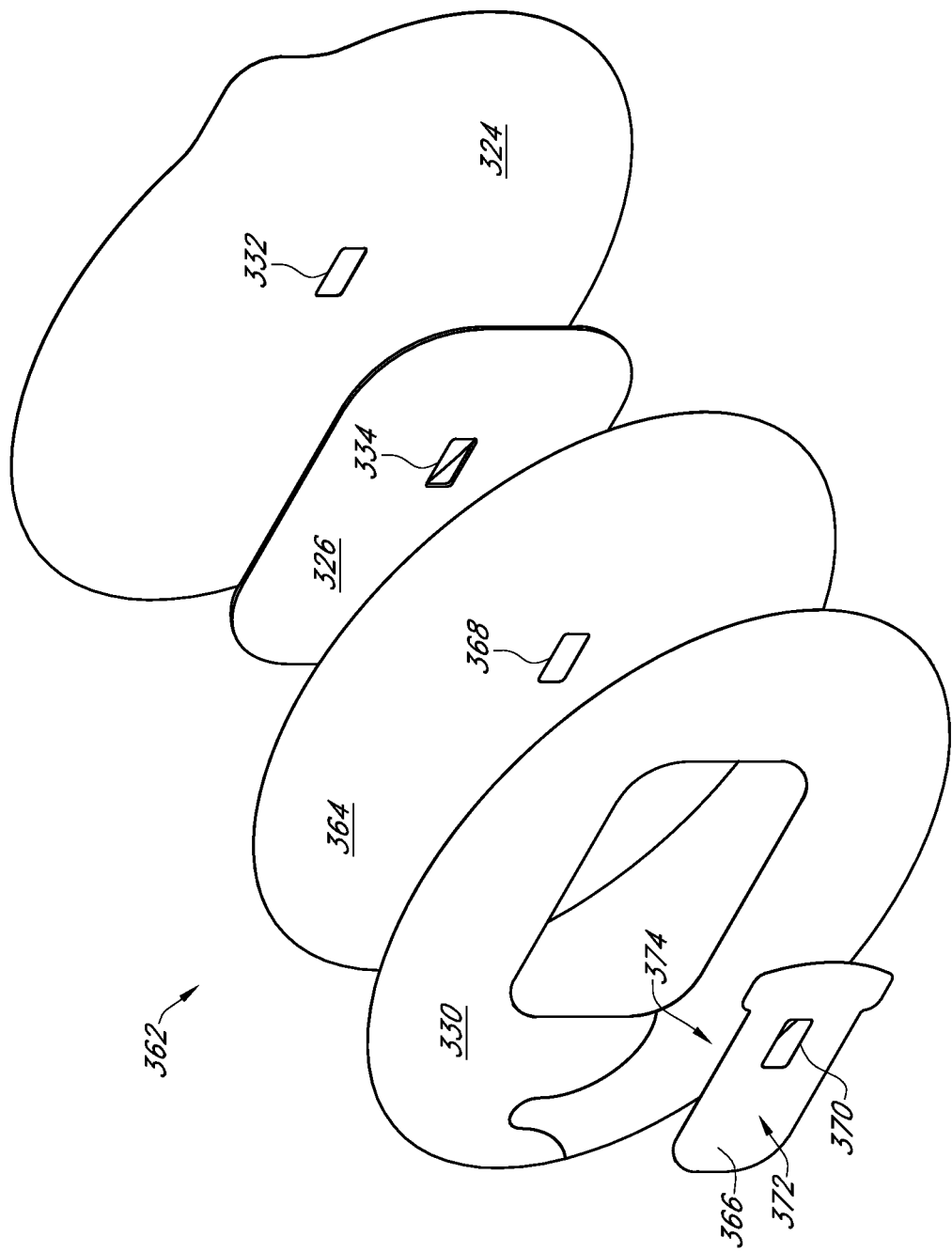
FIG. 14A is an exploded upper perspective view of another embodiment of a multilayer adhesive pad for an adhesive sensor system.
Figure 14B:
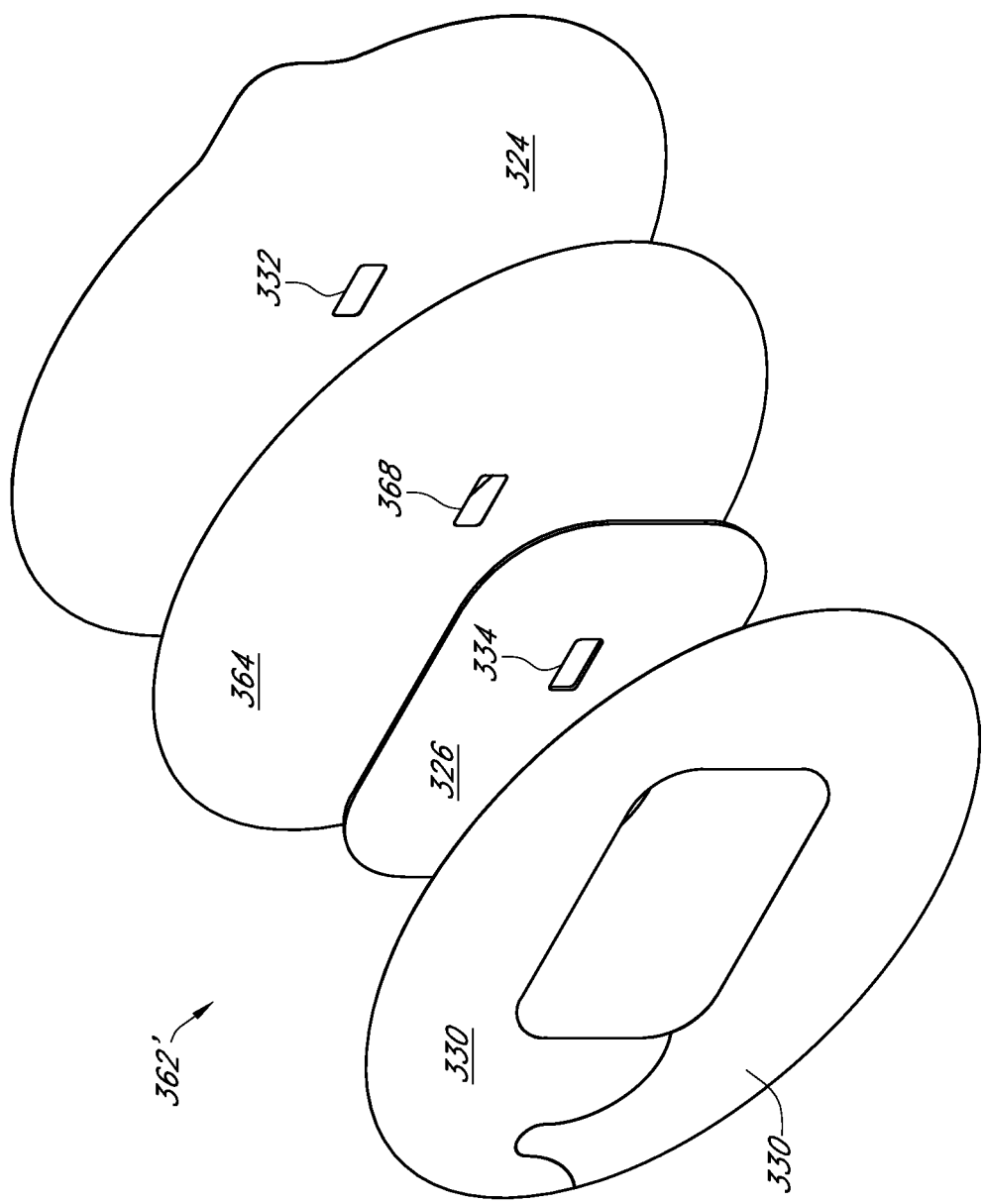
FIG. 14B is an exploded upper perspective view of still another embodiment of a multilayer adhesive pad for an adhesive sensor system.
Figure 15:
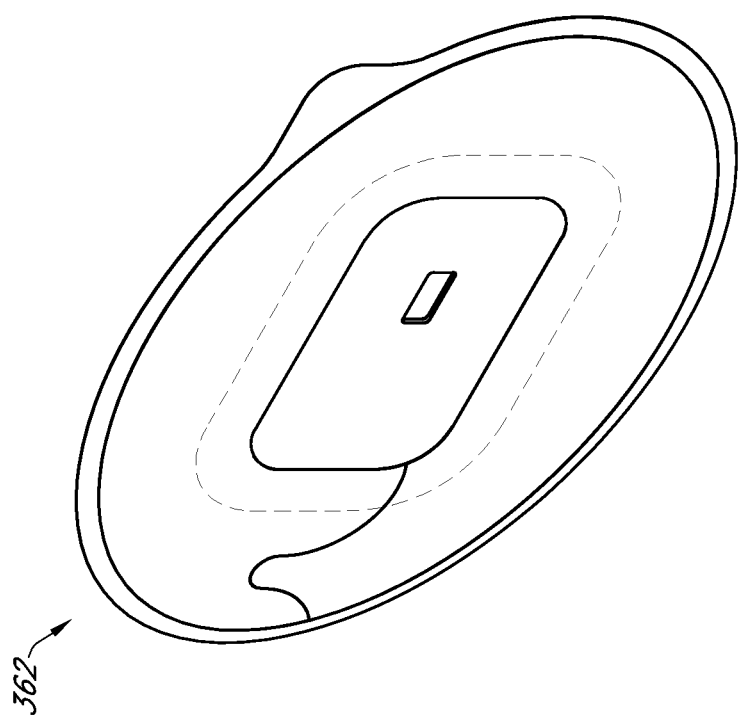
FIG. 15 is an assembled upper perspective view of the multilayer adhesive pad of FIG. 14A.

FIGS. 14-17 illustrate another example embodiment of an adhesive sensor system 360 (FIGS. 16-17) including a multilayer adhesive pad 362. The system 360 of FIG. 14A and FIGS. 15-17 is similar to the system 320 of FIGS. 10-13, except for a change in the configuration of the overlay 364 and the addition of a layer of double-sided tape 366. With reference to FIG. 14A, the overlay 364 includes an opening 368 having a substantially smaller size as compared to the embodiment of FIGS. 10-13. The opening 368 in the overlay 364 is substantially the same size and shape as the openings 332, 334 in the cushioning layer 326 and the inner liner 324. The opening 368 in the overlay 364 aligns with the openings 332, 334 in the cushioning layer 326 and the inner liner 324, as shown in FIG. 15, to accommodate the sensor.

Figure 16:
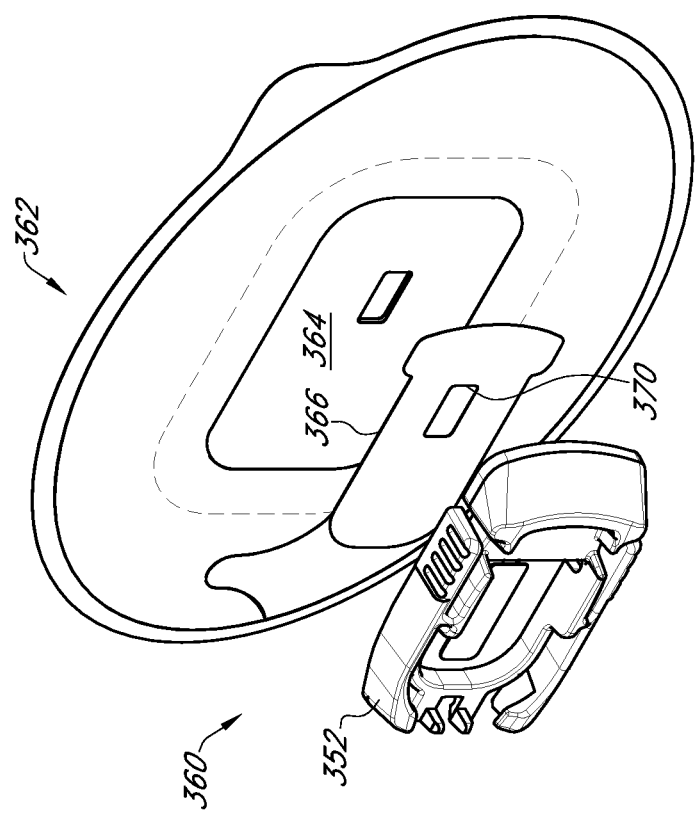
FIG. 16 is a partially exploded upper perspective view of the multilayer adhesive pad of FIG. 15 and a housing for a sensor electronics unit.
Figure 17:
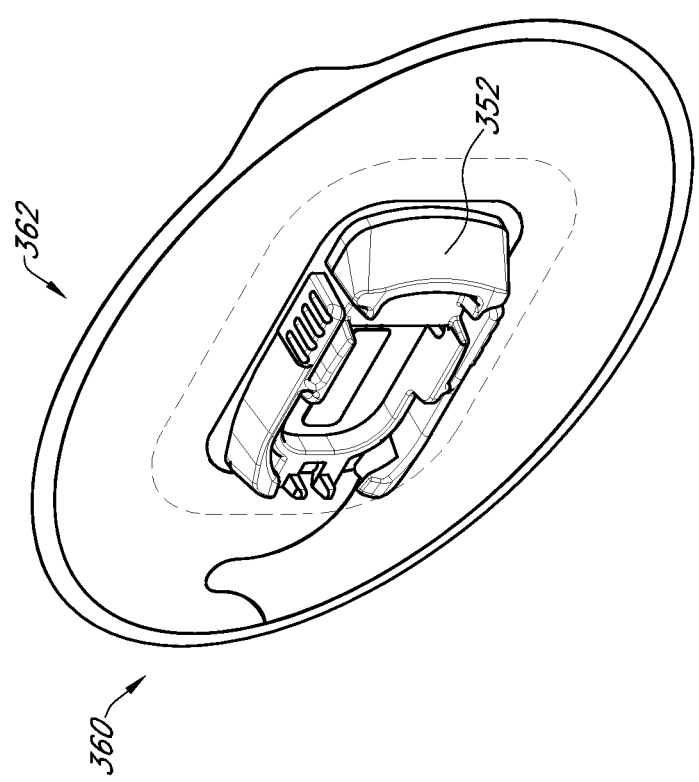
FIG. 17 is an assembled upper perspective view of the multilayer adhesive pad and the housing of FIG. 16.
Figure 18:
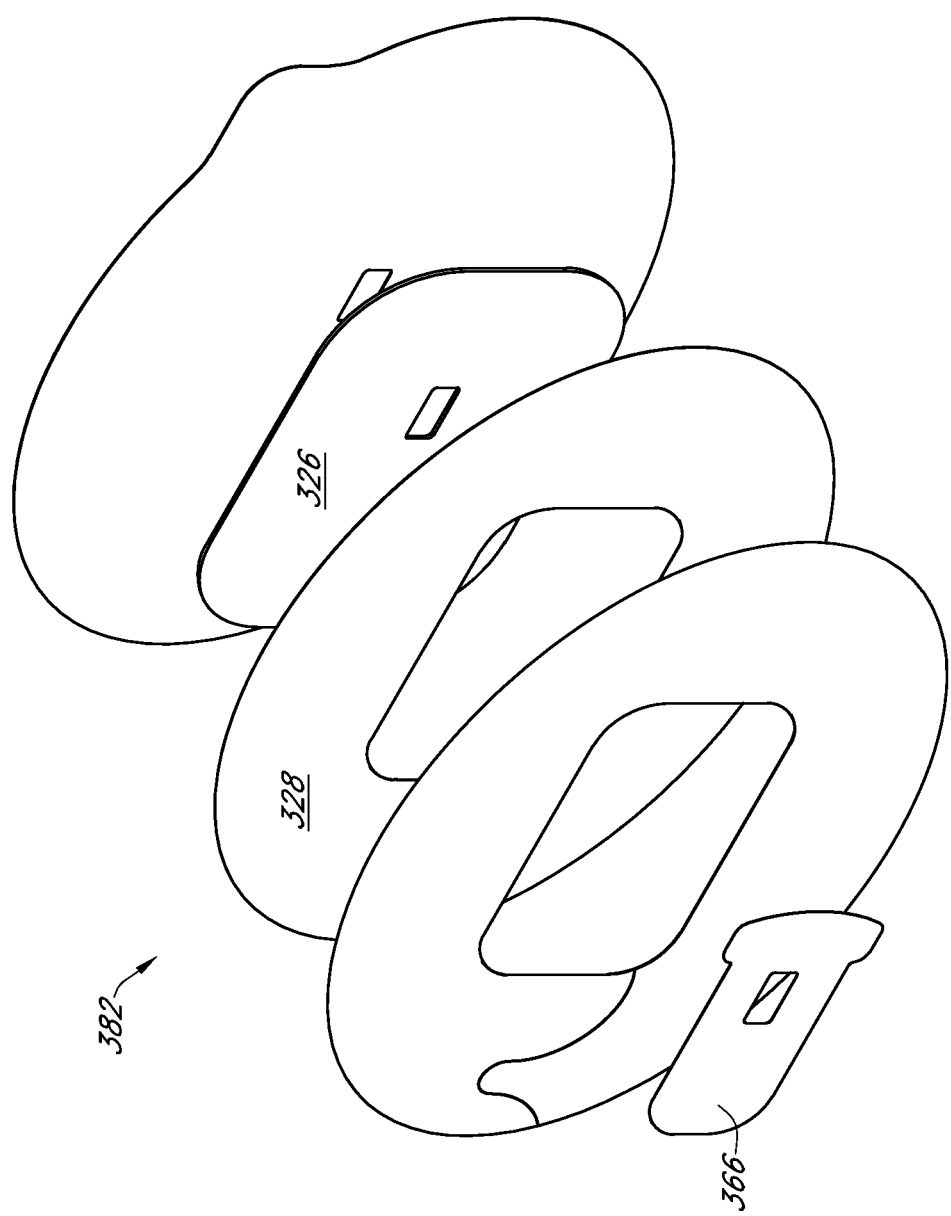
FIG. 18 is an exploded upper perspective view of another embodiment of a multilayer adhesive pad for an adhesive sensor system.
Figure 19:
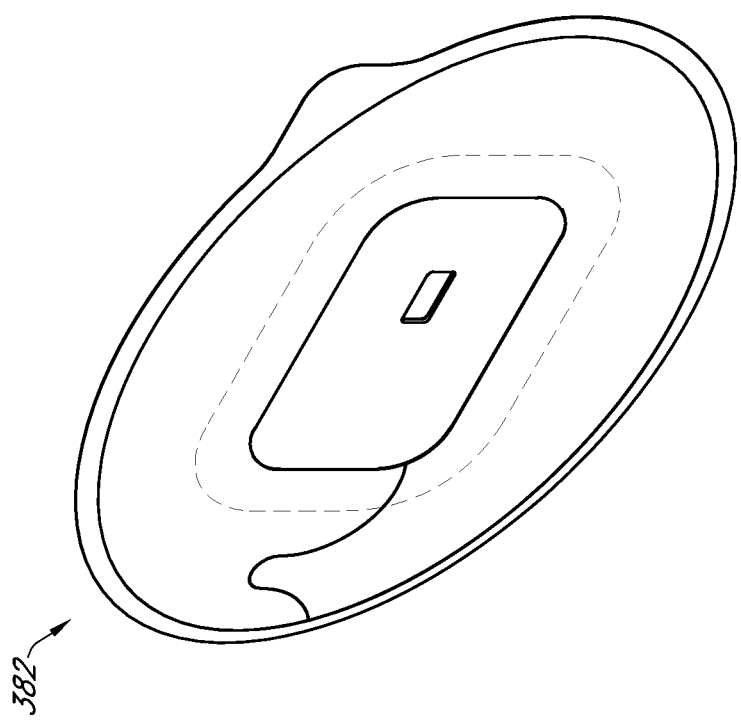
FIG. 19 is an assembled upper perspective view of the multilayer adhesive pad of FIG. 18.

Because of the reduced size of the opening 368 in the overlay 364, the sensor electronics unit housing 352 is not directly secured to the cushioning layer 326. Rather, with reference to FIGS. 16 and 17, the layer of double-sided tape 366 secures the sensor electronics unit housing 352 to the overlay 364. With reference to FIG. 16, the double-sided tape 366 includes an opening 370 that is substantially the same size and shape as the openings 332, 334, 368 in the overlay 364, the cushioning layer 326, and the inner liner 324. The opening 370 in the double-sided tape 366 aligns with the openings 332, 334, 368 in the overlay 364, the cushioning layer 326, and the inner liner 324 to accommodate the sensor. The double-sided tape 366 includes an adhesive material on its opposite surfaces 372, 374 (FIG. 14A) to facilitate securing the sensor electronics unit housing 352 to the overlay 364. The adhesive material may comprise any adhesive material, including any of those described herein, and/or any other material(s) not described herein. The double-sided tape 366 may include the same adhesive material on both surfaces 372, 374, or may include different adhesive materials on its opposite surfaces 372, 374. With reference to FIG. 16, an outer perimeter of the double-sided tape 366 may have a smaller perimeter than the outer perimeter of the sensor electronics unit housing 352. If the double-sided tape 366 has a tape with a larger outer perimeter (or a tape with the same outer perimeter but is not applied onto the sensor electronics unit housing 352 correctly to prevent an extended edge), the extended edges of the double-sided tape 366 could collect dust and debris. Additionally, the smaller outer perimeter of the double-sided tape 366 allows for manufacturing tolerances.

With reference to FIG. 14A, the overlay 364 includes an opening 368 having a substantially smaller size as compared to the embodiment of FIGS. 10-13. The opening 368 in the overlay 364 is substantially the same size and shape as the openings 332, 334 in the cushioning layer 326 and the inner liner 324. The opening 368 in the overlay 364 aligns with the openings 332, 334 in the cushioning layer 326 and the inner liner 324, as shown in FIG. 15, to accommodate the sensor.

The embodiment illustrated in FIGS. 14A and 15-17 provides several advantages. For example, omitting the large central opening in the overlay 364 permits a larger smooth surface area to bond the sensor electronics unit housing 352 to the pad for improved adhesion between the sensor electronics unit housing 352 and the pad. This design also simplifies manufacturing, as compared to a design with a large central opening. The double-sided tape design also provides several advantages. Use of the double-sided tape 366 eliminates the need for a heat stake process. It is generally easier and quicker to bond the sensor electronics housing 352 to the overlay 364 using double-sided tape 366. Furthermore, it is also easier to automate the process of bonding the sensor electronics unit housing 352 and the overlay 364 together using double-sided tape 366, as compared to a heat stake process. Furthermore, double-sided tapes are generally inexpensive and simple to form. In addition, waste from defects resulting from manufacturing can be reduced. For example, if the double-sided tape is not applied correctly during manufacturing, it can be simply removed without damaging the adhered parts (e.g., the sensor electronics unit housing). Unlike some other processes described herein (e.g. heat staking), the process of applying double-sided tape is reversible.

In still another embodiment, as illustrated in FIG. 14B, the adhesive pad 362' is similar to the adhesive pad 362 illustrated in FIG. 14A, except for the removal of the double-sided tape 366 from the design and also for a change with regard to having the cushioning layer 326 disposed on top of the overlay 364, instead of the other way around. With this configuration, the top layer of the adhesive pad 362' during use (i.e., after removal of the outer liner 330) is the cushion layer 326. As described elsewhere herein, in some embodiments, the transmitter housing may be heat-staked to the outermost layer of the adhesive pad. It has been unexpectedly found that certain materials used for the cushioning layer (e.g., a spunlace material or another woven material) provide a better material for heat-staking than certain materials (e.g., polyurethane or other thin polymer materials) used to form the overlay. In addition, because of the use of heat-staking to adhere the sensor electronics housing to the adhesive pad, a double-sided tape, such as the one shown in FIG. 14A may be omitted, thereby simplifying the adhesive design and reducing the risk of complications.

Figure 20:
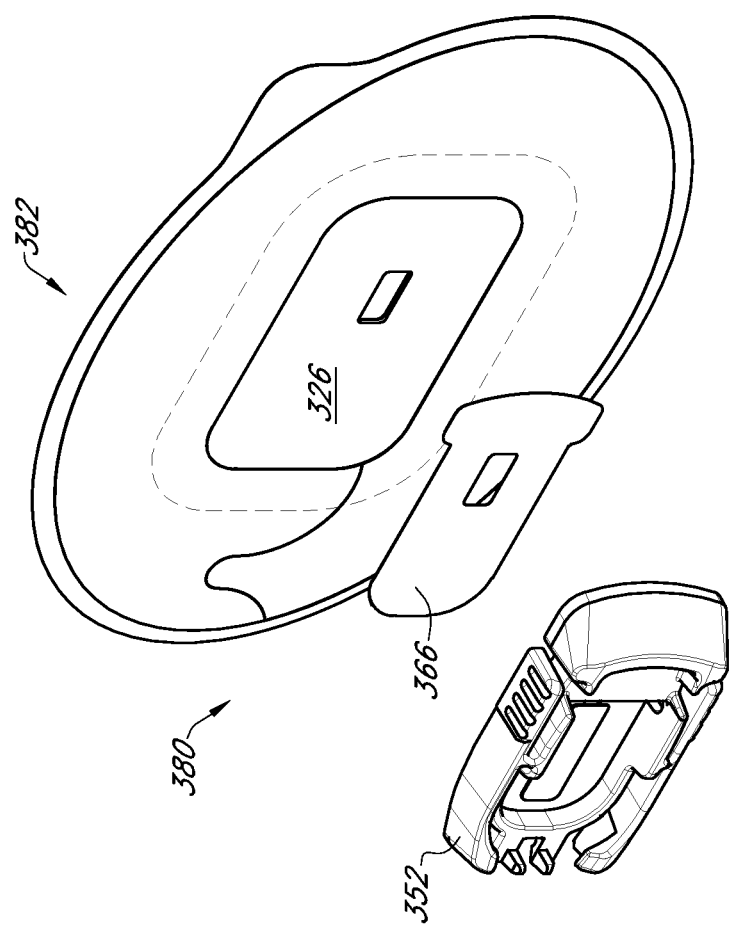
FIG. 20 is a partially exploded upper perspective view of the multilayer adhesive pad of FIG. 19 and a housing for a sensor electronics unit.
Figure 21:
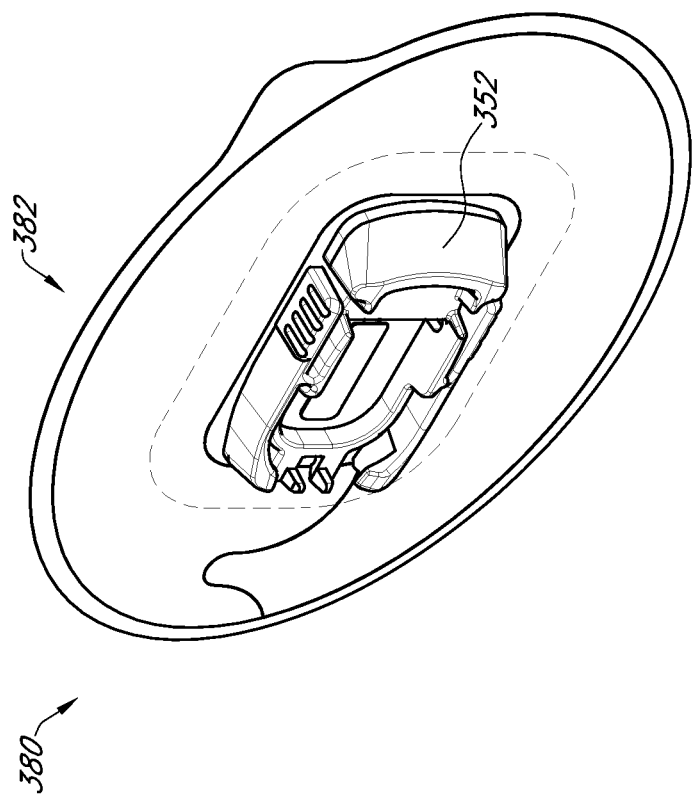
FIG. 21 is an assembled upper perspective view of the multilayer adhesive pad and the housing of FIG. 20.

FIGS. 18-21 illustrate another example embodiment of an adhesive sensor system 380 (FIGS. 20-21) including a multilayer adhesive pad 382. The system 380 of FIGS. 18-21 is similar to both the system 320 of FIGS. 10-13 and the system 360 of FIGS. 14-17. However, with reference to FIG. 18, the system 380 of FIGS. 18-21 combines the overlay 328 of the system 320 of FIGS. 10-13 and the layer of double-sided tape 366 of the system 360 of FIGS. 14-17. The double-sided tape 366 thus secures the sensor electronics unit housing 352 to the cushioning layer 326, as shown in FIGS. 20-21.

4. Perforated Overlay

Another aspect of the present embodiments includes the realization that removing the overlay covering the inner layer(s) can be challenging. For example, with reference back to FIGS. 2 and 3, the overlay 206 may begin peeling around the edges before the end of a sensor session. Thus, it is advantageous to remove the overlay and replace it with a fresh overlay so that the current sensor session can be extended. But it can sometimes be difficult to remove the overlay without disturbing the adhesive pad. If the adhesive pad is disturbed during the removal of the overlay, there can be movement that translate from the ex vivo portion of the sensor to the in vivo portion of the sensor. As described elsewhere herein, movement at the ex vivo portion of the sensor that contacts the electronics housing can translate across the length of the sensor to the in vivo portion of the sensor and cause complications and undesired effects. For example, movement translated to the in vivo portion of the sensor and cause complications, such as, irritation and inflammation, for example. In turn, these conditions can cause various forms of wound healing response from the patient's body, all of which can result in sensor inaccuracy, sensor failure, and/or shortened sensor life.

In recognition of the foregoing problem, as well as in recognition of any of the other problems discussed herein, some of the present embodiments provide an overlay having perforations dividing the overlay into at least two portions. For example, as described in detail below, a first portion of the overlay may be located radially outward from a second portion of the overlay, with a series of perforations forming a border between the first and second portions. When the edges of the first portion of the overlay begin to peel, the first portion may be easily removed by peeling it off the host's skin. The first and second portions separate at the perforations as the first portion is peeled off, leaving the adhesive pad undisturbed. The removed first portion can then be discarded, and a fresh overlay can be applied over the second portion of the first overlay and over the adhesive pad.

It should be understood that perforations can also be used for the adhesive pad. For example, a first portion of the adhesive pad may be located radially outward from a second portion of the adhesive pad, with a series of perforations forming a border between the first and second portions. When the edges of the first portion of the adhesive pad begin to peel, the first portion may be easily removed by peeling it off the host's skin. The first and second portions separate at the perforations as the first portion is peeled off, leaving the second portion of the adhesive pad undisturbed. The removed first portion can then be discarded. In some embodiments, an overlay can then be applied over the second portion of the adhesive pad.

Figure 43A:
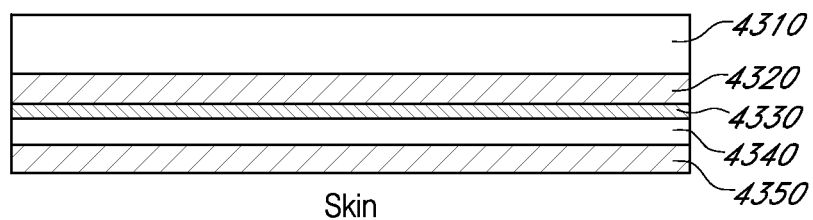
FIG. 43A-B are cross-sectionals view of one embodiment of a multi-adhesive-layer adhesive pad.
Figure 43B:
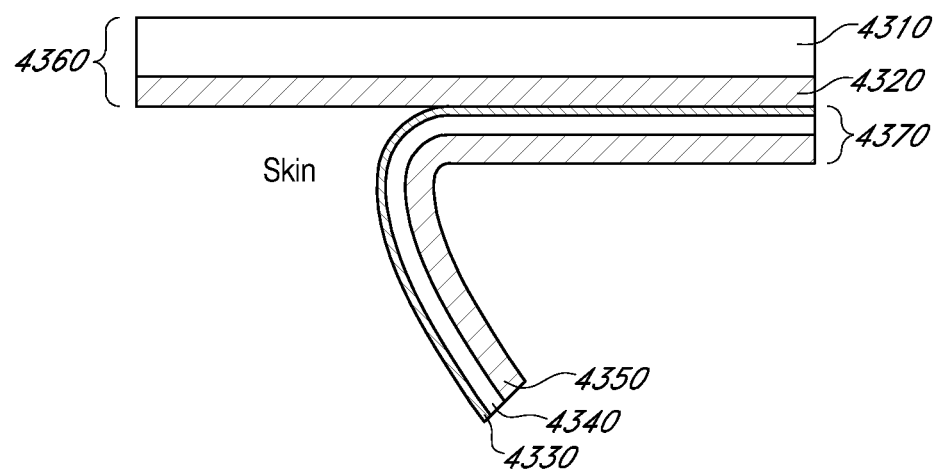

FIGS. 43A and 43B illustrate another example embodiment of an adhesive sensor system designed to provide long-term securing of the mounting unit to the skin of the user. In the embodiment shown in FIG. 43A, the adhesive pad comprises two adhesive layers 4320, 4350. However, in other embodiments the adhesive layers can comprise more than two adhesive layers, for example, two, three, four, five, seven, ten, or more adhesive layers. On the top layer 4360, a base (e.g., the sensor electronics unit housing) is affixed thereto. During use, after removal of a backing layer (not shown) the multilayer adhesive patch 4300 is first adhered to the user's skin. During this time, the first adhesive layer 4350 provides adherence to the skin. Optionally, between the first adhesive layer and the second adhesive layer is a backing layer 4340 for providing some mechanical rigidity or other desired properties to the first adhesive layer 4350. On top of the backing layer 4340, an optional low-stick layer 4330 (e.g., a silicone layer) may be provided. The low-stick layer 4330 allows the removal of the first adhesive layer 4350 while the affixed device is kept in place. Preferably, the low-stick will have properties that allow it to keep the two layers together during a period of use (e.g., 5-7 days), while still allowing the peeling off of the first adhesive layer 4350. After a period of use (e.g., 5-7 days), the first adhesive layer 4350 may start to detach from the skin. At this time, the user can peel of the bottom layer 4370. While removing the bottom layer 4370 from the skin, the second adhesive layer 4320 becomes exposed and can now be used to adhere to the skin, thereby allowing the device to be worn for an additional period of use (e.g., 5-7 days).

Figure 43C:
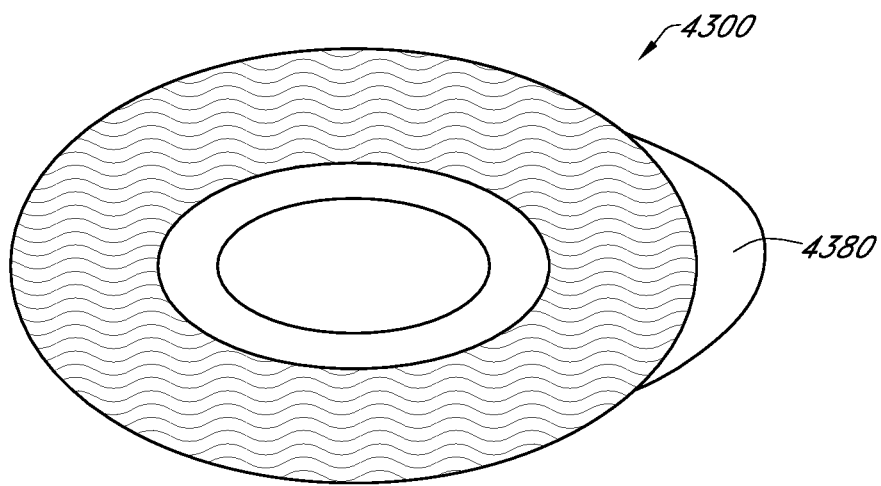
FIG. 43C is a top view of the embodiment illustrated in FIG. 43A.
Figure 43D:
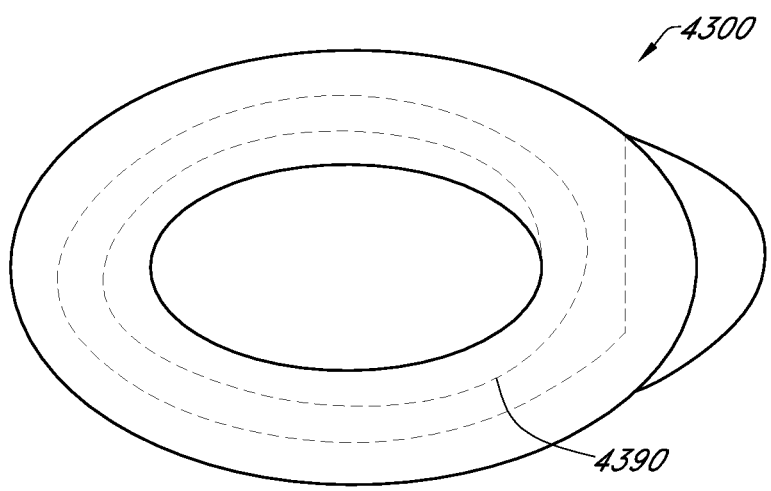
FIG. 43D is a bottom view of the embodiment illustrated in FIG. 43A.

FIGS. 43B and 43C illustrate a top and bottom view, respectively, of the adhesive pad 4300. The top view, as illustrated in FIG. 43B, shows the patch backing 4310 (e.g., a spunlace material or another woven material) on top of which a base (e.g., the sensor electronics unit housing) is affixed thereto. As illustrated in FIG. 43B, the adhesive pad 4300 may include a peel-off tab 4380 that may be used to initiate the peeling off of the first adhesive layer 4350. As illustrated in FIG. 45C, which provides a bottom view, the first adhesive layer 4350 of the adhesive pad 4300 may have a spiral cut 4390 that allows the first adhesive layer 4350 to be removed in a defined, circling manner.

Figure 22:
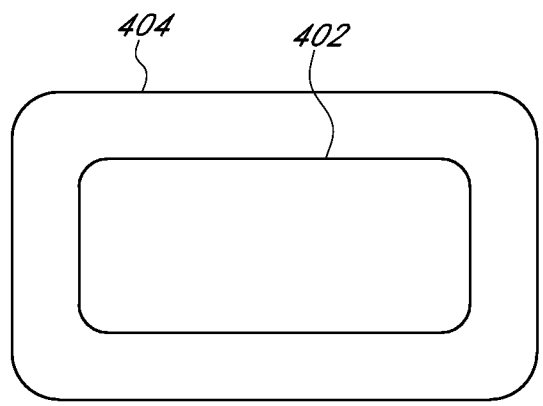
FIGS. 22-25 are schematic top plan views of one embodiment of an adhesive sensor system including a perforated overlay.
Figure 23:
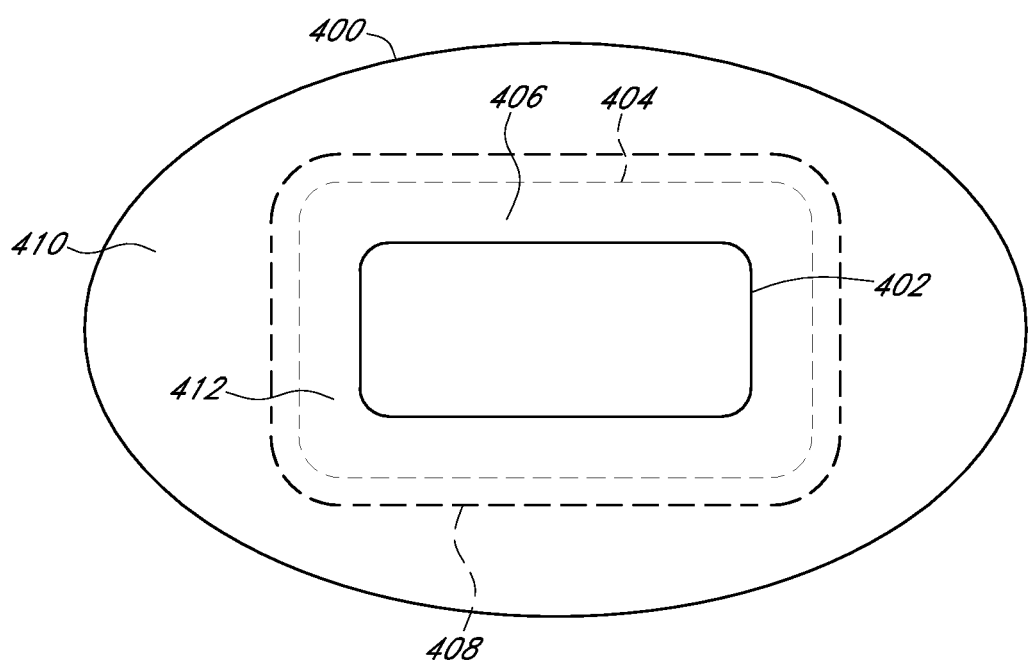

FIGS. 22-25 illustrate one example embodiment of an adhesive sensor system including a perforated overlay 400 (FIG. 23). With reference to FIG. 22, the sensor electronics unit housing 402 and the adhesive pad 404 are illustrated schematically. The adhesive pad 404 is secured to the host's skin (not shown). With reference to FIG. 23, the overlay 400 is subsequently placed over the adhesive pad 404. The overlay 400 includes a central opening 406 to accommodate the sensor electronics unit (not shown) and the sensor electronics unit housing 402, as shown and described above with respect to previous embodiments.

The overlay 400 includes perforations 408 that mark a boundary between a first radially outward portion 410 and a second inner portion 412. In some embodiments, the path traced by the perforations 408 may be substantially the same size and shape as the perimeter of the adhesive pad 404. In other embodiments, the path traced by the perforations 408 may have a larger or smaller perimeter dimension than the adhesive pad 404, and/or may have a different shape than the adhesive pad 404.

Figure 24:
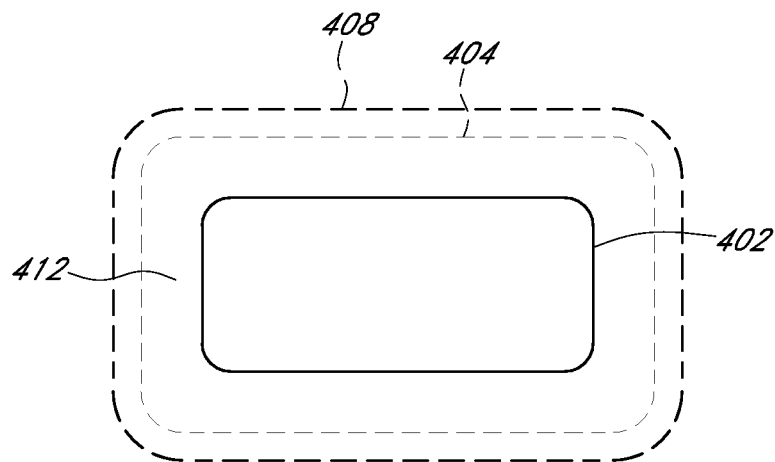
Figure 25:
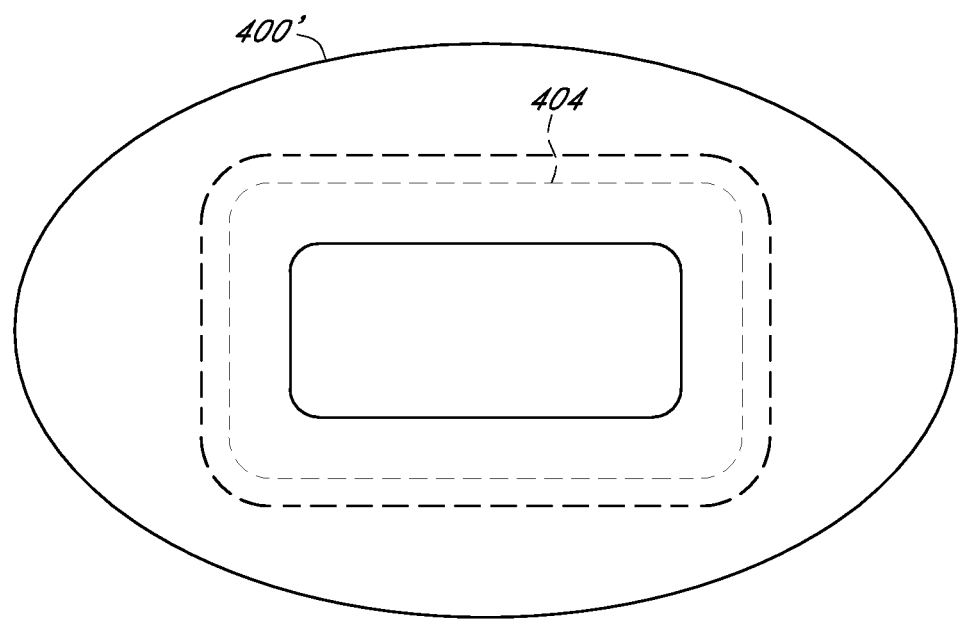

After the overlay 400 is secured to the host's skin, and as the sensor session progresses over a number of days, the edges of the overlay 400 may begin to peel away from the host's skin. Whenever desired, the host may remove the first (outer) portion 410 of the overlay 400 and discard the first portion 410. To remove the first portion 410, the host grasps any edge portion of the overlay 400 and peels it away from the skin. During this process, the first and second portions 410, 412 of the overlay 400 separate at the perforations 408 due to the strong adhesion of the overlay 400 to the underlying adhesive pad 404. Thus, after the first portion 410 of the overlay 400 has been removed, the second portion 412 of the overlay 400, the adhesive pad 404, and the sensor electronics unit housing 402 remain secured to the host's skin, as shown in FIG. 24. The host may then place a fresh overlay 400' over the second portion 412 of the first overlay 400 and the adhesive pad 404, as shown in FIG. 25. The fresh overlay 400' may remain secured to the host's skin for the remaining duration of the sensor session, thereby prolonging the usable life of the sensor.

In alternative embodiments, the overlay 400 and the adhesive pad 404 may be preassembled, such that the host need not perform the separate steps of applying the adhesive pad 404 to his or her skin and then placing the overlay 400 over the adhesive pad 404. Instead, the host applies the adhesive pad 404 and the preassembled overlay 400 to his or her skin in a single step.

In the embodiments described above, the overlay 400 includes a radially outward portion 410 that is easy to remove without disturbing the adhesive pad 404, because the outward portion 410 easily tears away from the inward portion 412 at the perforations 408. The removed portion can then be discarded, and a fresh overlay 400' can be applied over the remaining inward portion 412 of the first overlay 400 and over the adhesive pad 404.

In further alternative embodiments, a single component may be substituted for the overlay 400 and the adhesive pad 404. For example, the adhesive pad 404 may be extended radially outward and divided into first and second portions by a series of perforations. The separate overlay 400 component may be omitted from such embodiments. The perforated adhesive pad is secured to the host's skin, and when the edges of the perforated adhesive pad begin to peel, the host may remove the first (outer) portion of the perforated adhesive pad by peeling it away from the skin and separating the first and second portions of the perforated adhesive pad at the perforations. The host may then apply a fresh overlay that is substantially the same as the overlay 400' described in the foregoing embodiment. The overlay would cover the second portion of the perforated adhesive pad, which remains secured to the host's skin, and also provides a radially outward portion that adheres to the host's skin.

In the embodiments described above, the adhesive pad 404 and the overlay 400 both include adhesive material on their respective undersurfaces. In some embodiments, the adhesive material on the adhesive pad 404 may be the same adhesive material as that on the overlay 400. In other embodiments, the adhesive material on the adhesive pad 404 may be different from the adhesive material on the overlay 400. For example, the adhesive material on the adhesive pad 404 may be weaker or stronger than the adhesive material on the overlay 400. In embodiments that include a perforated adhesive pad and no overlay 400, the inner and outer portions of the perforated adhesive pad may include the same adhesive material or different adhesive materials. For example, the adhesive material on the inner portion of the perforated adhesive pad may be weaker or stronger than the adhesive material on the outer portion of the perforated adhesive pad.

5. Adhesive Pad and Overlay Comprising Different Materials

Another aspect of the present embodiments includes the realization that different materials in an adhesive sensor system may provide different advantages. For example, fabric materials are well suited for securing the sensor electronics unit housing to the adhesive pad using a heat staking process, while polymeric materials are well suited for strong adhesion to the host's skin using a thin layer that is difficult to peel off.

Figure 26:
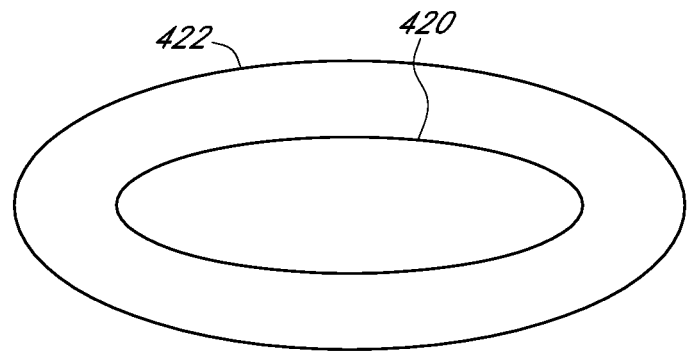
FIG. 26 is a schematic top plan view of one embodiment of an adhesive pad and overlay combination.

In recognition of the foregoing aspect, as well as in recognition of any of the other problems and/or aspects discussed herein, some of the present embodiments provide an adhesive pad and an overlay comprising different materials. For example, with reference to FIG. 26, the adhesive pad 420 may comprise a fabric material while the overlay 422 may comprise a polymeric material. The fabric adhesive pad 420 advantageously provides a surface on which the sensor electronics unit housing may be secured using a heat staking process, while the polymeric overlay 422 advantageously provides strong adhesion to the host's skin using a thin layer that is difficult to peel off.

In some embodiments, the adhesive pad may comprise a plurality of layers, with one or more layers formed of a first material configured to provide cushioning for the mounting unit and with one or more layers formed of a third material configured to provide adhesive strength with respect to adhesion to the skin. In further embodiments, the adhesive pad may comprise at least three layers, with each layer formed of a different material. For example, in one embodiment, the adhesive pad comprises a first layer may comprising a material configured for heat-staking, a second layer comprising a material configured to provide cushion against the mounting unit to provide patient comfort, and a third layer to provide adhesion strength with respect to adhesion to the skin. In still other embodiments, the adhesive pad may comprises four layers, each formed of a different material and each configured to serve a different function (e.g., for heat-staking, cushioning, wicking, breathability, structural integrity, certain mechanical properties, strong adhesion, etc.)

In any of the embodiments described herein that include an adhesive pad and an overlay, the adhesive pad and the overlay may comprise the same material. For example, the adhesive pad and the overlay may both comprise a polymeric material, such as a transparent polymeric material.

6. Different Adhesives

Another aspect of the present embodiments includes the realization that different adhesive materials may be advantageous for different applications. For example, some hosts may prefer a stronger adhesive for a reduced likelihood of the adhesive peeling off the skin, while other hosts may prefer a weaker adhesive to make it easier to remove the sensor system when desired.

Figure 27:
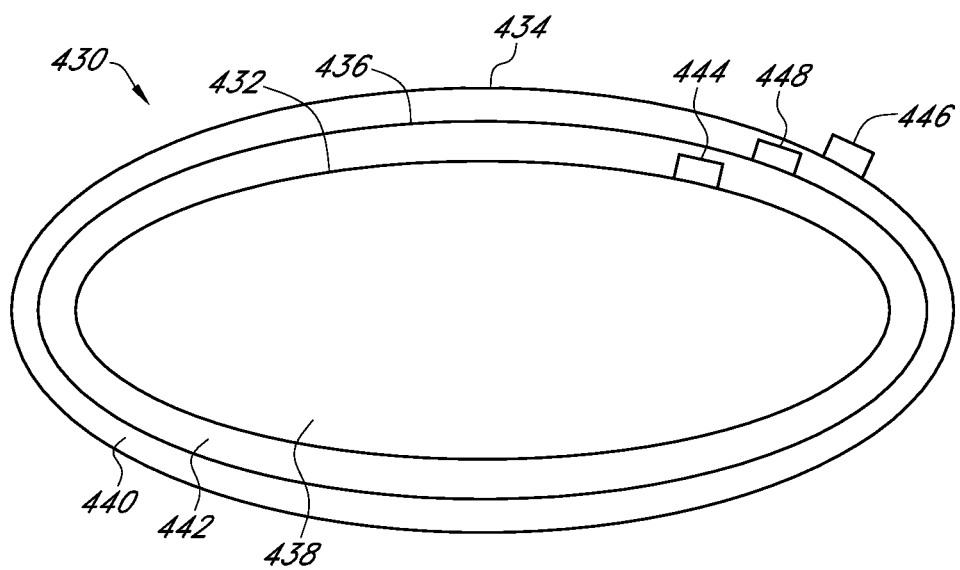
FIG. 27 is a schematic bottom plan view of another embodiment of a multilayer adhesive pad for an adhesive sensor system.

In recognition of the foregoing aspect, as well as in recognition of any of the other problems and/or aspects discussed herein, some of the present embodiments provide an adhesive pad having a plurality of layers, where each layer includes an adhesive material of a different strength. Furthermore, the present embodiments provide an adhesive configured to provide secured, stable adhesion to the skin (or both the skin and the adhesive pad in the case of the overlay) for at least 7 days, preferably 14 days, and can be easily removed with minimal force. For example, with reference to FIG. 27, the adhesive pad 430 comprises an innermost layer 432, an outermost layer 434, and an intermediate layer 436. Each of the layers 432, 434, 436 is coated on its undersurface with a different adhesive material, and/or with the same adhesive material in different strengths. For example, the innermost layer 432 may have the weakest adhesive, the outermost layer 434 may have the strongest adhesive, and the intermediate layer 436 may have an adhesive with a strength somewhere between the weakest adhesive and the strongest adhesive. In another example, the innermost layer 432 may have the strongest adhesive, the outermost layer 434 may have the weakest adhesive, and the intermediate layer 436 may have an adhesive with a strength somewhere between the weakest adhesive and the strongest adhesive.

Each of the layers 432, 434, 436 is covered with a removable backing 438, 440, 442, and each backing includes a pull tab 444, 446, 448 at its periphery. The host may select one of the innermost layer 432, the outermost layer 434, or the intermediate layer 436 for use by pulling a selected one of the pull tabs 444, 446, 448. The host thus may advantageously select a most desired one of the adhesive layers 432, 434, 436 based upon personal preference.

In the foregoing embodiments, the provision of three adhesive layers 432, 434, 436 is just one non-limiting example. In various embodiments, any number of layers may be provided, including two layers, or four layers, or any other number of layers.

The adhesive pad 430 described above and shown in FIG. 27, as well as all of the adhesive pads described herein, may be provided as a part of an adhesive sensor system. Such adhesive sensor systems may include any or all of a continuous analyte sensor, a sensor electronics unit, and/or a housing for receiving the sensor electronics unit.

7. Small Surface Area Adhesive Pad

Another aspect of the present embodiments includes the realization that edges of the adhesive pad tend to fray and/or peel off first, which may cause a cascading effect in which the rate of peel increases. More surface area for the adhesive pad does not necessarily provide better adhesion. In fact, a larger surface area results in a larger perimeter, which can increase the likelihood of the adhesive pad peeling at its edges.

Figure 28:
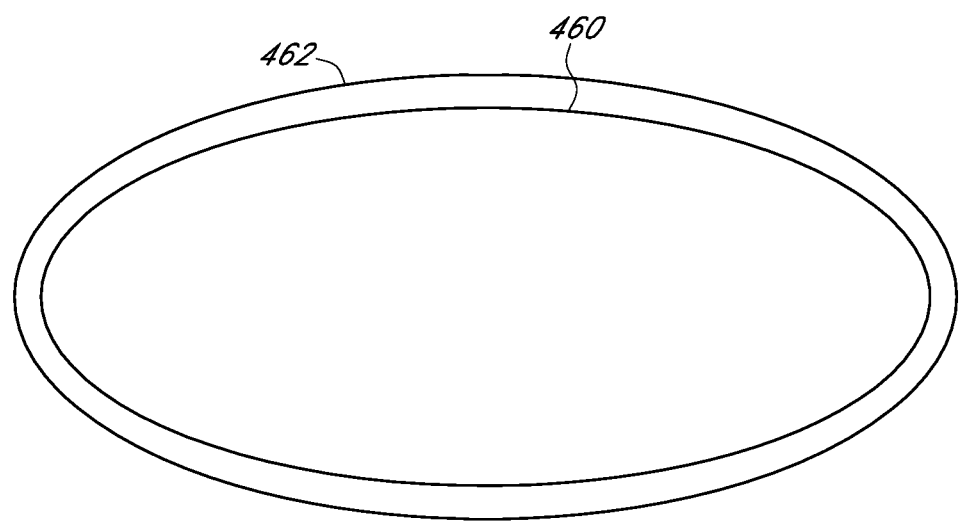
FIG. 28 is a schematic bottom plan view of one embodiment of an adhesive pad and sensor electronics unit housing combination.

In recognition of the foregoing problem, as well as in recognition of any of the other problems discussed herein, some of the present embodiments provide an adhesive pad with a smaller area than the sensor electronics unit housing. With this arrangement, the adhesive pad is configured to resist early peel-off and premature detachment, because pressure from the sensor electronics unit housing is constant being applied onto the adhesive pad in the direction of skin surface. For example, with reference to FIG. 28, the adhesive pad 460 is the same shape as the housing 462, but has a smaller perimeter dimension. In some embodiments, the adhesive pad 460 may have a perimeter dimension that is no larger than 1/32 inch, no larger than 1/16 inch, no larger than 1/8 inch, no larger than 1/4 inch, or no larger than 1/2 inch. The housing 462 thus completely covers the entire perimeter of the adhesive pad 460, which provides several advantages. For example, the edges of the adhesive pad 460 are recessed behind the perimeter of the housing 462, and therefore are not susceptible to peeling as a result of friction applied by objects that might otherwise come into contact with the adhesive pad 460. Further, any downward pressure on the sensor electronics unit housing 462, which may occur as the host moves about, is translated into pressure on the edges of the adhesive pad 460, which may further reinforce the bond between the adhesive pad 460 and the host's skin.

8. Adhesive Pad that does not Require Sterilization

Another aspect of the present embodiments includes the realization that, according to current practice, the mounting unit of a continuous analyte monitoring system typically undergoes sterilization after assembly, e.g., after the adhesive pad has been assembled to the mounting unit. One type of sterilization process is electron beam processing, also referred to as electron irradiation or e-beaming. E-beaming is a process using electrons, usually of high energy, to kill microbes that may be resident on the object being irradiated. The e-beaming process, which may take place under elevated temperature and/or in a nitrogen atmosphere, typically weakens the adhesiveness of the adhesive pad. Therefore, there is a need for an adhesive pad system having resistance to e-beaming or one designed to avoid e-beaming (or other forms of sterilization) all together.

In recognition of the foregoing problem, as well as in recognition of any of the other problems discussed herein, some of the present embodiments provide a continuous analyte monitoring system in which the adhesive pad does not undergo sterilization. For example, the system may include a first assembly comprising an inserter configured to insert a continuous analyte sensor into a host and the continuous analyte sensor itself, which is disposed at least in part in the inserter. The system may include a second assembly, which comprises a mounting unit that includes an electronics housing and an adhesive pad having an upper surface and an undersurface. The mounting unit is configured to be placed over a host's skin. The electronics housing of the mounting unit is attached to the upper surface of the adhesive pad, and the undersurface of the adhesive pad includes an adhesive material for adhering to the host's skin. The inserter may be configured to insert the continuous analyte sensor into the host. The continuous analyte sensor is disposed in the inserter prior to sensor insertion. In some embodiments, the inserter is configured to be secured to a fastener of the mounting unit prior to sensor insertion. With the above-described design, the mounting unit may be adapted to undergo a different sterilization process than the inserter and/or the continuous analyte sensor. In some embodiments, the mounting unit is designed to not undergo sterilization. During use, the user is provided with the first assembly with an inserter and a sensor disposed therein and with the second assembly that comprises a mounting unit that includes an electronics housing and an adhesive pad. The user then secures the inserter onto the mounting unit. The fastening mechanism may employ any of a variety of techniques for securing components to each other including, but not limited to, bolts, clamps, buckles, hooks, latches, snap fastener, threaded fastener, for example. The fastening mechanism may be designed such that when the inserter is fastened and secured to the mounting unit, the inserter is positioned and oriented in a predetermined configuration (e.g., location and angle) that will allow for suitable sensor insertion. Next, the user employs the inserter to insert the sensor through the skin. After sensor insertion, the user may then unsecure and unfasten the inserter from the mounting unit. Afterwards, in some embodiments, a transmitter or other electronic is placed onto the mounting unit.

In some embodiment, a kit is formed including a first assembly comprising a mounting unit comprising an sensor inserter and a sensor disposed therein and a second assembly comprising a mounting unit configured to fasten onto the inserter prior to sensor insertion. The mounting unit comprises a sensor electronics housing configured to receive a sensor electronics unit (e.g., a transmitter) and an adhesive pad system. In some embodiments, the first assembly may be disposed in a first package and the second assembly may be disposed in a second package. In addition, the first assembly is sterilized, while the second assembly is not sterilized. In one embodiment, the adhesive pad is designed such that sterilization is not required. For example, the adhesive pad may comprise an opening with a boundary that is spaced at distance sufficiently far from the insertion/wound site, such that sterilization is not required. In other words, in this embodiment, there is no contact between the adhesive pad system and the insertion/wound site.

Figure 29:
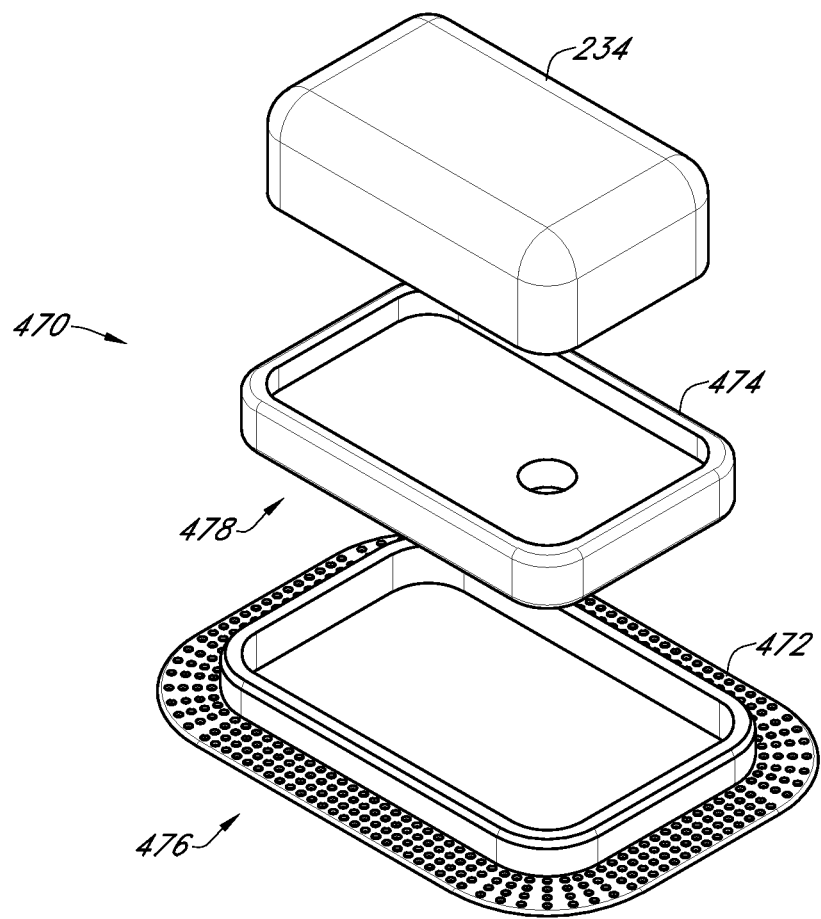
FIG. 29 is an exploded upper perspective view of another embodiment of an adhesive sensor system.

In another example, with reference to FIG. 29, the system 470 may include a mounting frame 472 and a housing 474 that are formed separately from the sensor electronics unit 234. Properties of the mounting frame 472 and/or the housing 474 may be similar to the corresponding components of the embodiment described above and shown in FIGS. 4 and 5. For example, one or both of the mounting frame 472 and the housing 474 may include an adhesive material on their undersurfaces 476, 478. In a process for making the system 470 of FIG. 29, the sensor electronics unit 234 may undergo sterilization, such as an e-beaming process, while the mounting frame 472 and/or the housing 474 do not undergo sterilization. The adhesive material on the mounting frame 472 and/or the housing 474 thus is not subjected to processing that may tend to weaken its adhesiveness. The sensor electronics unit 234 may subsequently be combined with the mounting frame 472 and the housing 474, for example by the host during a process for inserting the sensor into his or her skin. The sensor electronics unit 234 may, for example, be combined with an insertion apparatus, which may also undergo sterilization, either separately or together with the sensor electronics unit 234. In alternative embodiments, the mounting frame 472 and the housing 474 may comprise an integral unit rather than separate components.

While the foregoing embodiment has been described with reference to FIG. 29, the concepts embodied therein are adaptable to any of the other embodiments described herein, as well as to embodiments that are not explicitly described herein but are clearly contemplated by the present disclosure. For example, the concept of sterilizing some components of a continuous analyte monitoring system and later combining the sterilized components with other components, such as an adhesive pad, that have not been sterilized, is adaptable to other embodiments. Depending on characteristics of the adhesive pad, such as its dimensions, it may be unnecessary to sterilize the adhesive pad, thereby preventing it from risk of damage from sterilization. For example, if the adhesive pad includes an aperture through which the sensor extends into the host's skin, and this aperture is large enough to provide sufficient distance between the sensor insertion site and the adhesive pad, sterilization of the adhesive pad (and the mounting unit attached thereto) may not be necessary.

Figure 30:
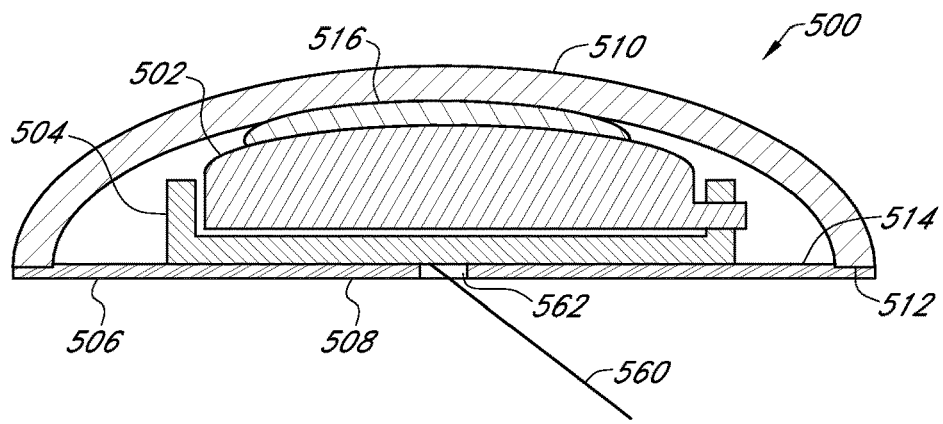
FIG. 30 is a partial cross-sectional view of one embodiment of an adhesive sensor system including a cover.
Figure 31:
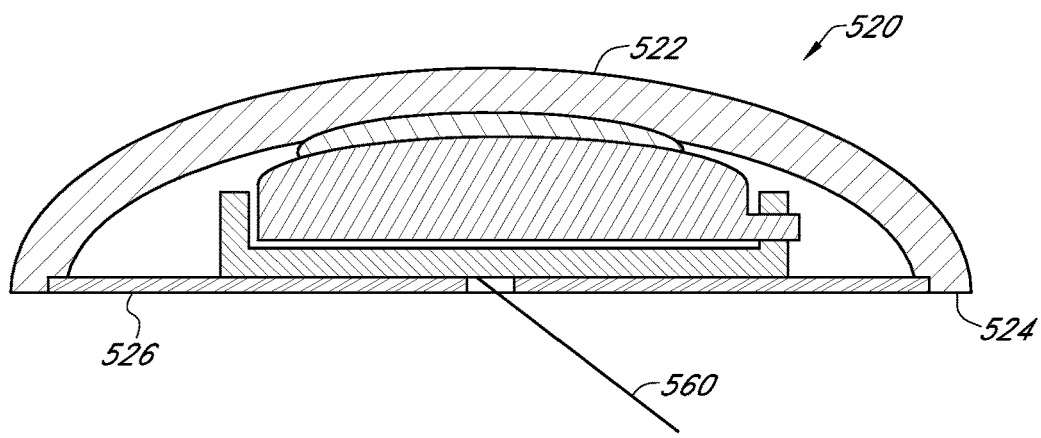
FIG. 31 is a partial cross-sectional view of another embodiment of an adhesive sensor system including a cover.
Figure 32:
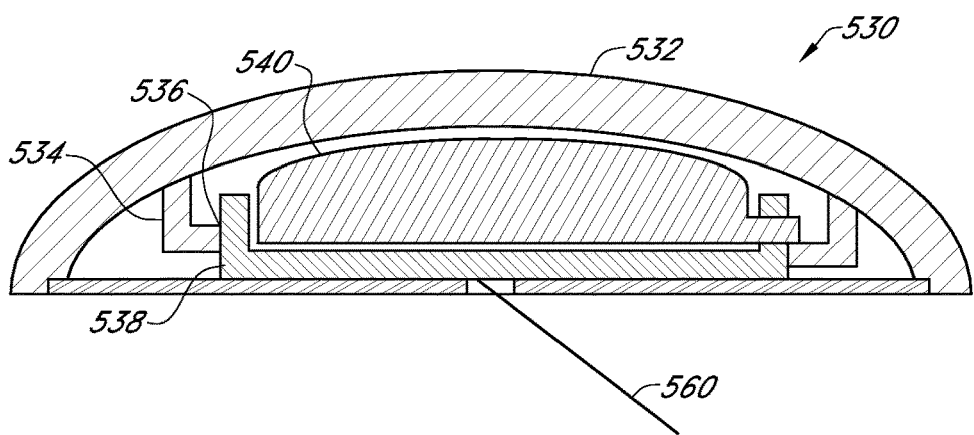
FIG. 32 is a partial cross-sectional view of another embodiment of an adhesive sensor system including a cover.

FIGS. 30-32 illustrate further embodiments of an adhesive sensor system having a cover over the sensor electronics unit. With reference to FIG. 30, one embodiment of a system 500 includes a sensor electronics unit 502 that is received in a housing 504. The sensor electronics unit 502 and/or the housing 504 may be similar to the corresponding components of other embodiments described herein. The housing 504 is secured to an adhesive pad 506, which includes an adhesive material on its undersurface 508 for securing the system 500 to the host's skin (not shown). The adhesive pad 506 and/or the adhesive material may be similar to the corresponding components of other embodiments described herein.

The system 500 further includes a cover 510 that extends over the sensor electronics unit 502, the housing 504, and the adhesive pad 506. As illustrated, a sensor 560 extends from the housing 405 through an opening 562 in the adhesive pad 506 and ultimately through a user's skin during use. Although the sensor is shown to extend from the opening 562 of the adhesive pad 506 at about a 45 degree angle, in other embodiments, the sensor may extend from the opening 562 at any of a variety of angles, such as, a 10 degree angle, a 30 degree angle, a 60 degree angle, a 90 degree angle, a 120 degree angle, a 150 degree angle, or a 170 degree angle, for example. In the illustrated embodiment, the cover 510 includes an arcuate or dome-shaped body that advantageously provides the cover 510 with an unobtrusive profile. However, the illustrated shape is just one non-limiting example. In other example embodiments, the cover may have any shape, such as rectangular.

The cover 510 includes a perimeter surface 512 that abuts an upper surface 514 of the adhesive pad 506 at an outer periphery thereof. This configuration reinforces adhesion of the adhesive pad 506 at the perimeter edge, which is the portion of the adhesive pad that typically is more likely to peel off first. Either one or both of the cover perimeter surface 512 and the adhesive pad upper surface 514 may include an adhesive material to secure the cover 510 and the adhesive pad 506 to one another. The adhesive material(s) may be similar to any of the adhesive materials described herein or may be any other adhesive material(s) not described herein, and the adhesive material on the cover perimeter surface 512 may be the same as or different from the adhesive material on the upper surface 514 of the adhesive pad 506.

With continued reference to FIG. 30, an adhesive material 516 may be interposed between an inner surface of the cover 510 and an outer surface of the sensor electronics unit 502. The cover 510 may thus be secured directly to the sensor electronics unit 502 to enhance the sturdiness of the system 500. The adhesive material 516 between the cover 510 and the sensor electronics unit 502 may be similar to any of the adhesive materials described herein or may be any other adhesive material not described herein.

FIG. 31 illustrates another embodiment of an adhesive sensor system 520 having a cover 522. The embodiment of FIG. 31 is similar to the embodiment of FIG. 30, except that at least a portion of the perimeter surface 524 of the cover 522 is exposed from the adhesive pad 526. The exposed portion of the cover perimeter surface 524 may include an adhesive material so that the cover 522 can be secured directly to the host's skin. The adhesive material on the cover perimeter surface 524 may be similar to any of the adhesive materials described herein or may be any other adhesive material not described herein.

FIG. 32 illustrates another embodiment of an adhesive sensor system 530 having a cover 532. The embodiment of FIG. 32 is similar to the embodiment of FIG. 31, except that the inside of the cover 532 includes structure 534 for mechanically mating with corresponding structure 536 on the sensor electronics unit housing 538. The structure 534, 536 on the housing 538 and the cover 532 may comprise, for example, a tongue and groove, a tab and slot, etc. so that the cover 532 engages the housing 538 with a snap fit. In the illustrated embodiment, the adhesive material interposed between the cover 532 and the sensor electronics unit 540 is omitted. However, in alternative embodiments the adhesive material may be present in addition to the mechanical mating structure 534, 536.

In the embodiments of FIGS. 30-32, the cover 510, 522, 532 advantageously shields and protects the components of the adhesive sensor system 500, 520, 530 from mechanical stresses that may result from being bumped, jostled, etc. The cover 510, 522, 532 also shields and protects the components of the adhesive sensor system 500, 520, 530 from intrusion by moisture, dust, etc. By distributing forces applied to the sensor system 500, 520, 530, the cover 510, 522, 532 may reduce an increase in sensor accuracy following implantation of the sensor. This phenomenon is often referred to as "dip and recover." A material of the cover 510, 522, 532 may be hard or soft, rigid or flexible, depending upon desired characteristics for a given application. The cover may be constructed of any suitable biocompatible material, such as one or more polymers, metals, ceramics, etc. Non-limiting examples of polymers from which the cover may be constructed include nylon, polyethylene, polyurethane, ethylene-vinyl acetate (EVA), polyether block amide (PEBAX), acrylonitrile butadiene styrene (ABS), polyether ether ketone (PEEK), polytetrafluoroethylene (PTFE), thermoplastic polyetherimide (ULTEM), etc. Non-limiting examples of metals from which the cover may be constructed include stainless steel, titanium, cobalt-chromium, etc. Non-limiting examples of ceramics from which the cover may be constructed include porcelain, alumina, hydroxyapatite, zirconia, etc. The cover may be customizable with graphic prints, patterns, cartoon characters, etc. The cover also may be any color, such as various skin tones to enable the adhesive sensor system to be less conspicuous.

C. Additional Features

1. Channels and Wicking Material(s)

Another aspect of the present embodiments includes the realization that moisture, such as from sweat, typically reduces the adhesiveness of an adhesive pad. This is an important consideration because the adhesive pad of a wearable sensor has to be capable of supporting the mass and volume of the sensor assembly, and be robust to resist pushing and pulling forces on that mass and volume (to resist detachment of the sensor assembly from the skin). Also, in contrast to bandages or other conventional medical tapes, if the adhesive fails before seven days have elapsed since sensor insertion, the wearer cannot simply swap out the failed adhesive pad for another adhesive pad, at least not without destroying the sensor and/or ending the sensor session. But sensors are quite costly. Therefore, it is highly desirable to avoid destroying the sensor before its useful life has elapsed (typically seven days according to the current state of the art).

In recognition of this problem, as well as in recognition of any of the other problems discussed herein, some of the present embodiments provide a wicking material and/or channels to remove moisture from the adhesive pad. These embodiments advantageously enable moisture to be removed from the adhesive pad without needing to remove the adhesive pad from the host. In some embodiments, the adhesive patch comprises a wicking material (e.g., in the form of strands) that accelerate the transport of moisture droplets from the skin to the surface where evaporation would occur more quickly.

Figure 33:
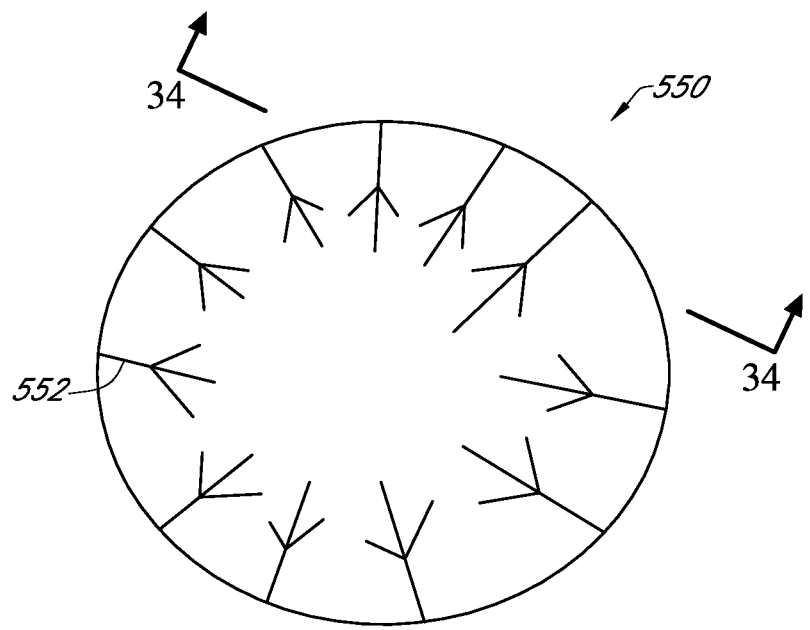
FIG. 33 is a schematic top plan view of one embodiment of an adhesive pad for an adhesive sensor system, the adhesive pad having a plurality of channels for enabling outflow of moisture.

FIG. 33 illustrates, schematically, one embodiment of an adhesive pad 550 for an adhesive sensor system, the adhesive pad 550 having a plurality of channels 552 for enabling outflow of moisture. Although in the embodiment illustrated in FIG. 33 uses a channel system with a spoke pattern to move moisture to the edge of the adhesive pad 550, it should be understood that any of a variety of other channel designs that move moisture to the edge or the surface of the adhesive pad 500 are also contemplated. In some embodiments, the channels extend radially outwards to the edge of the adhesive pad. In certain embodiments, one or more channels of the channel system extend outwardly from a center point of the adhesive pad to certain points along the edge of the adhesive pad. In any of the channel systems contemplated herein, the channel can extend either in a straight line, in a substantially straight line, or in a curve.

Figure 34:
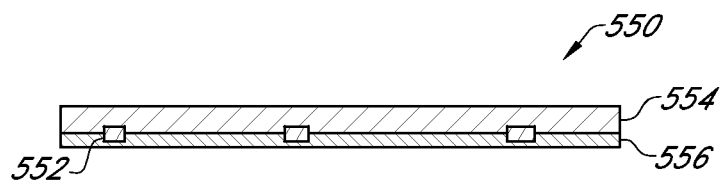
FIG. 34 is a cross-sectional view of the adhesive pad of FIG. 33, taken through the line 34-34 in FIG. 33.

FIG. 34 is a cross-sectional view of the adhesive pad 550 of FIG. 33, taken through the line 34-34 in FIG. 33. With reference to FIG. 34, the adhesive pad 550 includes a body portion 554 comprising an upper layer 554 of the pad 550, and an adhesive material 556 comprising a lower layer 556 of the pad 550. The adhesive material 556, or lower layer 556, is configured to abut the host's skin to secure the adhesive pad 550 to the host. The adhesive material 556 may be similar to any of the adhesive materials described herein or may be any other adhesive material not described herein.

With reference to FIGS. 33 and 34, the adhesive pad 550 further includes a plurality of channels 552. The channels 552 may be formed in either or both of the body portion 554 (upper layer 554) and the adhesive material 556 (lower layer 556). In the illustrated embodiment, the channels 552 extend in a generally radial direction from the center of the adhesive pad 550 to the edges thereof. The channels 552 may extend all the way to the center of the adhesive pad 550, and may be interconnected, either at a common point of connection at or near the center of the adhesive pad 550, and/or through additional channels (not shown) that connect adjacent ones of the channels 552 and extend in directions transverse to the radial channels 552. Similarly, the channels 552 may extend all the way to the edges of the adhesive pad 550, or may stop short of the edges. The channels 552 may also comprise a combination of channels 552 that extend all the way to either or both of the center and the edges and some channels 552 that do not extend all the way to either or both of the center and the edges. The pattern of channels 552 may be selected to provide a desired moisture channeling behavior.

In some embodiments, the channels 552 may comprise open space, e.g. spaces that are not filled with any solid material. In other embodiments, the channels 552 may comprise one or more wicking materials embedded within the adhesive pad 550. Wicking materials draw moisture away from the host's skin due to capillary action. Example wicking materials include, without limitation, nitrocellulose, wool, synthetic materials such as polyester, polyethylene, polyethylene terephthalate (PETE), and microfiber-based fabrics. Such wicking material(s) may be prepared with hydrophilic coatings and/or hydrophobic coatings and/or other coatings and chemistries in order to facilitate a desired direction of moisture transpiration. Such wicking material(s) may also be prepared with coatings for the purpose of applying calibration constants and/or medicines for the host. In various embodiments, wicking may be structured in a manner to provide a microfluidic behavior, such as transfer of liquids and/or gases in a single direction by use of channel size and/or surface coatings.

In the above-described embodiments, moisture, such as from sweat, is advantageously transported away from the dermal surface beneath the adhesive pad 550. The deleterious effects of such moisture, such as compromising the adhesive properties of the adhesive pad 550, are thereby reduced. Wicking materials and/or channels 552 may additionally be used to apply chemicals and/or other materials to the host's skin without needing to remove the adhesive pad 550 from the skin. Wicking materials that can be used include, for example, nitrocellulose, polyester weave, cotton, linen, and any other material with absorbent properties. Further advantages may include leveraging the wicking behavior to refresh the adhesive by movement of liquid adhesive through the wicking material.

Figure 44A:
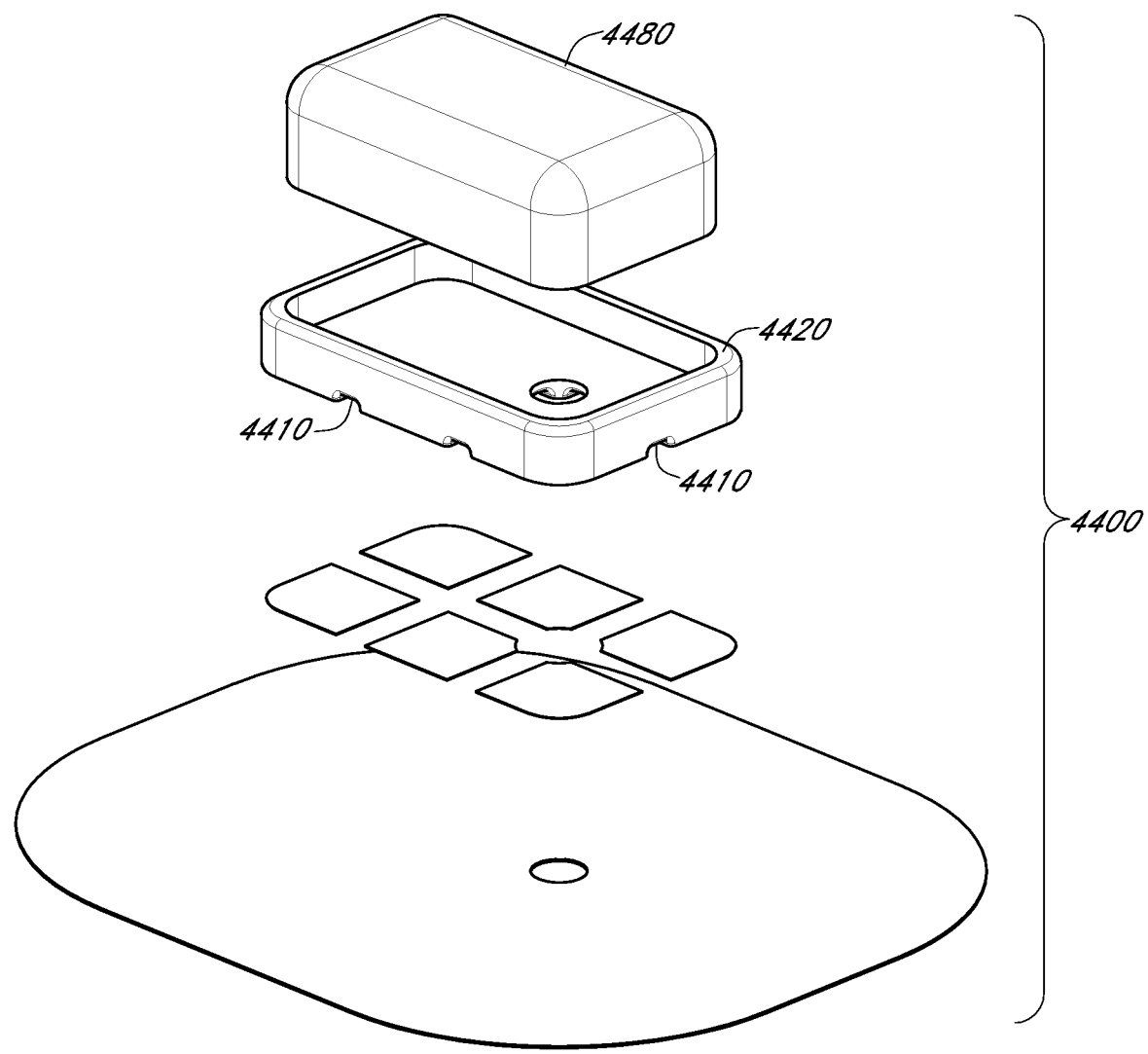
FIG. 44A is an exploded upper perspective view of one embodiment of an adhesive sensor system including electronics unit housing with a channel system formed in its bottom surface.
Figure 44B:
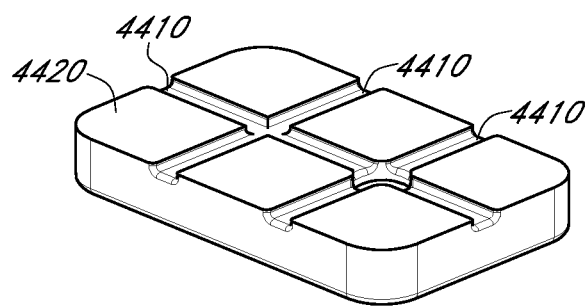
FIG. 44B is perspective view of the bottom surface of the electronics unit housing illustrated in FIG. 44A.

FIG. 44A illustrates one embodiment of an adhesive sensor system 4400 comprising an electronics unit housing 4420 that has a plurality of channels 4410 on its bottom surface for enabling outflow of moisture. For a better view of the channels 4410, FIG. 44B provides a perspective view of the bottom surface of the electronics unit housing 4420. The top portion of the electronics unit housing 4420 is configured to receive an electronics unit 4480. Although the embodiment illustrated in FIG. 44A uses a channel system with a grid-like pattern to move moisture to the edge of the electronics unit housing 4420, it should be understood that any of a variety of other channel designs that move moisture to the edge electronics unit housing 4420 may also be used. In some embodiments, not shown, the channels 4410 extend from a center portion of the electronics units housing 4420 in a straight line outwards to its edge in a spoke-like pattern. In any of the channel systems contemplated herein, the channel 4410 can extend either in a straight line, in a substantially straight line, or in a curve.

2. Flexible Applicator

Another aspect of the present embodiments includes the realization that for some devices used to secure an adhesive pad of a continuous analyte monitoring system to a host, a rigid applicator surface presses the adhesive pad against the host's skin across the entirety of the adhesive pad. In this process, air bubbles may be trapped between the adhesive pad and the host's skin. These air bubbles provide potential oxidation zones that can reduce the life of the adhesive material on the adhesive pad. The air bubbles also provide boundary edges for the adhesive pad from which lifting of the pad may begin to propagate. All of these potential issues can cause the early peel-off and/or premature detachment of the adhesive pad. Early peel-off and/or premature detachment issues can be more severe, as compared to a simple bandage, because there is a mounting unit attached thereto. The mounting unit adds additional weight and height/volume, which in turn increase the risk of pushing and pulling forces on that mass and volume that can facilitate detachment of the mounting unit/adhesive pad from the skin. In recognition of this problem, as well as in recognition of any of the other problems discussed herein, some of the present embodiments provide an applicator having a flexible surface configured for applying pressure to the adhesive pad. Applying uniform pressure across the surface of the adhesive pad advantageously reduces or prevents formation of air bubbles.

Figure 35:
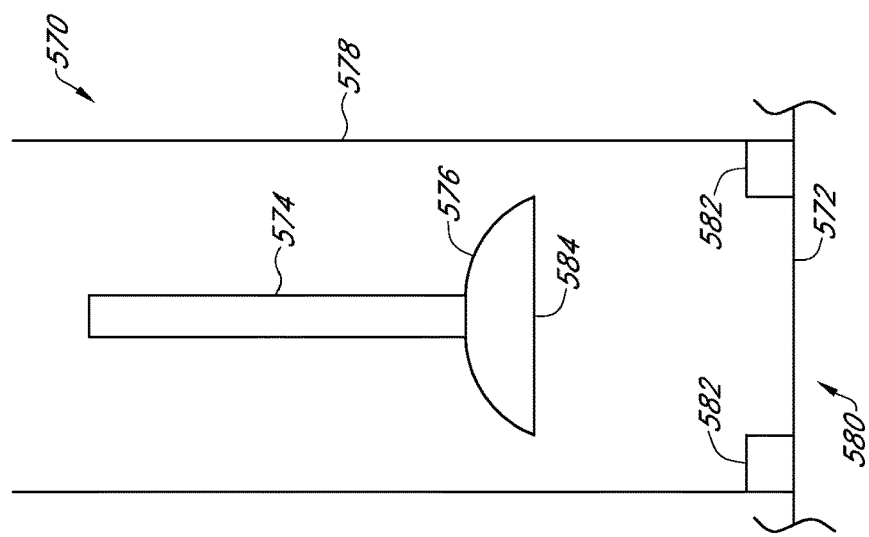

FIGS. 35-40 illustrate, schematically, one embodiment of an applicator device 570 for an adhesive pad of an adhesive sensor system. FIGS. 35-40 show successive stages of a process for securing the adhesive pad to a host's skin 572 using the applicator device 570. With reference to FIG. 35, the applicator device 570 comprises an actuator portion 574 and a flexible applicator portion 576 at a distal end of the actuator portion 574. The actuator portion 574 may comprise, for example, a piston-like member that is translatable within a cylinder 578. A distal end, or outlet end 580, of the cylinder 578 includes a reduced diameter as represented schematically by the blocks 582 on either side of the outlet end 580 of the cylinder 578 in FIG. 35. The reduced diameter may be provided with, for example, an inwardly extending flange at the outlet end 580. An adhesive pad (not shown) abuts a distal face 584 of the applicator portion 576, such that actuation of the applicator device 570 applies the adhesive pad to the host's skin 572, as further described below.

The applicator portion 576 preferably comprises a flexible and resilient material. For example, and without limitation, the applicator portion 576 may comprise silicone, polyamides (e.g. nylon), rubber (e.g. synthetic rubber), polyethylene terephthalate (PET), low-density polyethylene (LDPE), thermoplastic polyurethane, thermoplastic elastomer, and combinations thereof.

Figure 37:
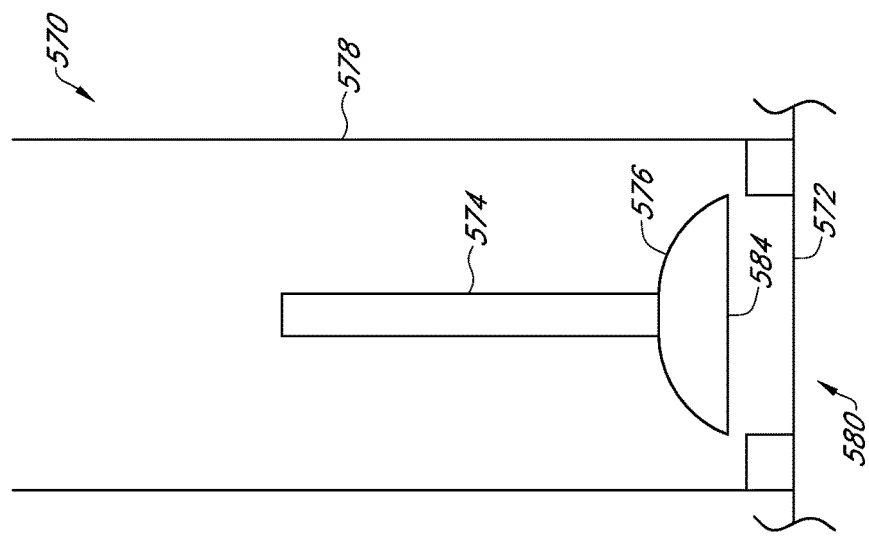
Figure 36:
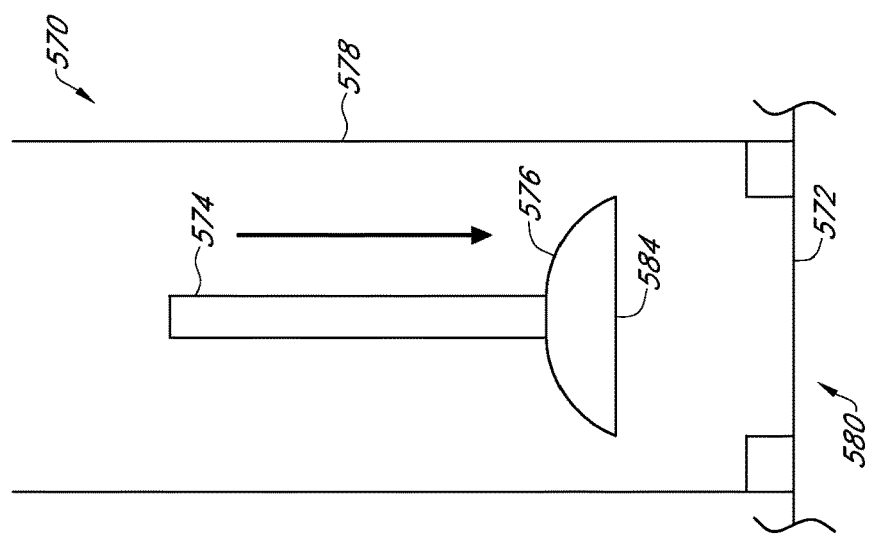

With reference to FIG. 36, in operation of the applicator device 570 the distal end 580 of the cylinder 578 is placed against the host's skin 572. The actuator portion 574 and the applicator portion 576 then move downward within the cylinder 578 until the applicator portion 576 reaches the distal end 580 of the cylinder 578, as shown in FIG. 37. A diameter of the distal face 584 of the applicator portion 576 is slightly greater than a diameter of the outlet end 580 of the cylinder 578. Thus, as the actuator portion 574 continues moving downward within the cylinder 578, the applicator portion 576 flexes as shown in FIG. 38 as the actuator portion 574 forces the center of the applicator portion 576 downward while the edge 582 of the outlet end 580 of the cylinder 578 impedes the distal movement of the edges 586 of the applicator portion 576. The center of the adhesive pad on the distal face 584 of the applicator portion 576 thus contacts the host's skin 572 first, as shown in FIG. 38. Eventually, the edges 586 of the applicator portion 576 move distally through the outlet end 580 of the cylinder 578, as shown in FIG. 39, due to the temporary reduction in the width of the applicator portion 576 that results from the flexing of the applicator portion 576. As the edges 586 of the applicator portion 576 move distally, the entire adhesive pad is forced against the host's skin 572 in a progression that starts at the center of the adhesive pad and proceeds outward in all directions toward the edges of the adhesive pad. This progression results from the flexing and unflexing of the applicator portion 576 as it is forced through the smaller diameter of the outlet end 580 of the cylinder 578. Eventually, the entire applicator portion 576 emerges from the cylinder 578 and returns to its unstressed shape, as shown in FIG. 40.

The foregoing motion of the applicator portion 576 advantageously reduces or eliminates the formation of air bubbles between the adhesive pad and the host's skin 572. Because the applicator portion 576 flexes as it exits the cylinder 578, the center of the adhesive pad contacts the host's skin 572 first. Then, as the applicator portion 576 flattens out, it pushes the adhesive pad against the host's skin 572 in a smooth progression from the center toward the edges. As the adhesive pad flattens out, it pushes air out of the space between the adhesive pad and the host's skin 572. The reduction or elimination of air bubbles avoids the problems discussed above, such as oxidation zones and boundary edges. Thus, the above-described potential issues (e.g., increased risk of early peel-off and/or premature detachment of the adhesive pad because of a mounting unit attached thereto) are minimized.

In alternative embodiments, the applicator portion 576 may have different shapes than as illustrated in FIGS. 35-40. For example, the applicator portion 576 may have a shape that does not apply pressure to the center, because the adhesive pad may not be present there. The adhesive pad may be, for example, ring shaped such that no portion of the adhesive pad lies over the center of the applicator portion 576. Also in alternative embodiments, the applicator portion 576 may be configured to apply variously directed forces. For example, the applicator portion 576 and/or the system for actuating the applicator portion 576 may be configured to apply force in a radially inward direction, from the perimeter of the applicator portion 576 toward the center. Such an embodiment might be well suited for applying an adhesive pad to the host's skin 572 wherein the adhesive pad has an opening in its center, e.g. a ring-shaped adhesive pad. The opening may be configured to allow for passage of a sensor, for example.

3. Smearing Adhesive

Another aspect of the present embodiments includes the realization that some adhesive pads do not have a flat undersurface (the surface that abuts the host's skin). For example, the adhesive pad may comprise a woven material.

For such pads, areas between adjacent fibers may be spaced from the host's skin, and therefore the bond between the adhesive pad and the skin may not be as strong as possible. As described elsewhere herein, a weak bond between the adhesive pad and the skin can result in early peel-off and/or premature detachment of the adhesive pad from the skin. As described elsewhere herein, early peel-off of the adhesive pad can be problematic even before the adhesive pad completely detaches from the skin. When the adhesion between the adhesive pad and the skin becomes weak and not sufficiently stable, the electronics housing and the sensor in contact therewith may become susceptible to undesired shaking and movement. Movement at the ex vivo portion of the sensor that contacts the electronics housing can translate across the length of the sensor to the in vivo portion of the sensor and cause complications and undesired effects. For example, movement translated to the in vivo portion of the sensor and cause complications, such as, irritation and inflammation, for example. In turn, these conditions can cause various forms of wound healing response from the patient's body, all of which can result in sensor inaccuracy, sensor failure, and/or shortened sensor life.

In recognition of this problem, as well as in recognition of any of the other problems discussed herein, some of the present embodiments provide an applicator that applies a laterally directed force, such as a rotational force, as the adhesive pad is pressed against the host's skin to thereby generate shear force between the adhesive pad and the host's skin. The shear force "smears" the adhesive material, causing it to fill in spaces and push out air bubbles. For example, the applicator portion may follow a small "jog and reverse" path as the adhesive pad is pressed against the host's skin, in which the jog and reverse path is directed laterally across the surface of the host's skin. Alternatively, the applicator portion may undergo a small rotation about an axis normal to the host's skin as the adhesive pad is pressed against the host's skin. These motion paths for the applicator portion may be achieved with guides, rails, or other structure on the apparatus for securing the adhesive pad to the host. In some embodiments, the applicator may be a part of a sensor inserter device that is configured to insert the sensor into the patient, but in other embodiments, the applicator may be a separate device.

4. Anti-Fraying Edge

Another aspect of the present embodiments includes the realization that the edge of the adhesive pad is typically the first portion to peel away from the host's skin. This problem is particularly acute with fabric adhesive pads, which may have threads that have a tendency to fray at the edges. In recognition of this problem, as well as in recognition of any of the other problems discussed herein, some of the present embodiments provide various treatments for reducing the thickness of the edges to resist fraying. By resisting fraying, the useful life of the adhesive pad can be extended to 7 days, 14 days, or preferably longer. In turn, the useful life of the sensor can also be extended to 7 days, 14 days, or preferably longer.

In one example embodiment, pressure and/or elevated temperature may be applied at the edges of the adhesive pad. Pressure may be applied, for example, by passing the adhesive pad, or just the edges of the adhesive pad, through a die to compress the edges. Heat may be applied, for example, to the edges to melt the adhesive pad material and thereby inhibit formation of fine strings that can get caught on clothes or other objects. This embodiment is particularly suited to meltable materials. Other example processes include, without limitation, ultrasonic welding to compress the edges of the adhesive pad, and solvent melting or solvent bonding at the edges of the adhesive pad.

The contour of the adhesive pad and the thickness profile corresponding to the contour may be designed to provide comfort to the wearer without sacrificing susceptibility to premature detachment. It has been found that adhesive pads with increased thickness provide more cushion to skin against the device disposed on the adhesive pad. However, it has also been found that relatively thicker adhesive pads are more susceptible to premature detachment, as compared to relatively thinner adhesive pads. In some embodiments, the perimeter edge of the adhesive pad may have a thickness that is less than the thickness of another portion (e.g. the interior portion(s)) of the adhesive pad. In certain embodiments, the perimeter edge has a thickness that is from about 5% to about 95% of the thickness of the interior, sometimes from about 10% to about 80%, sometimes from about 25% to about 75%, and sometimes from about 33% to about 50%.

5. Piezochromic Material

Another aspect of the present embodiments involves the realization that inadequate and/or non-uniform pressure applied across the adhesive pad during the process of applying the adhesive pad to the host's skin can result in premature peeling of the adhesive pad from the skin. When insufficient pressure is applied to a section of the adhesive pad, that section may not be properly adhered to the skin. Similarly, if there is substantial non-uniformity in pressure applied across the adhesive pad, certain sections may not adhere well, thereby creating a bulge that is susceptible to early peeling. Thus, it is advantageous to prevent un-depressed areas from forming bulges or bubbles of un-adhered material. In recognition of the foregoing potential complications, as well as in recognition of any of the other advantages or disadvantages discussed herein, some of the present embodiments provide an adhesive pad comprising an indicator that notifies the user whether sufficient pressure has been applied to promote proper adherence of the adhesive pad to the skin. In some embodiments, the indicator may be in the form of a piezochromic material that changes color when a threshold pressure is applied. The piezochromic material may, for example, be embedded in the adhesive material on the undersurface of the pad.

In one example embodiment, the color changes when a sufficient pressure has been applied. In another embodiment, the material changes to one color (e.g., green) when a desired amount of pressure is applied, and changes to another color (e.g., red) when too much pressure is applied. A lack of color change in the material may indicate that not enough pressure has been applied. The color change may help to ensure that a substantially uniform pressure is applied across the surface of the adhesive pad. In some embodiments, the entire adhesive pad may include the color-changing material. In other embodiments, only certain portions of the adhesive pad (e.g., the edges) may include the color-changing material.

6. Antimicrobial Material and/or Agents

Another aspect of the present embodiments includes the realization that long-term use of a transcutaneous device may increase the risk of infection. In recognition of this problem, as well as in recognition of any of the other problems discussed herein, some of the present embodiments provide an antimicrobial material integrated into the adhesive pad and/or applied on the surface(s) of the adhesive pad and/or other portions of the adhesive sensor system that are in close proximity to the sensor insertion site. Example antimicrobial materials include, without limitation, silver compounds, copper compounds, zinc compounds, brass compounds, and alloys and/or combinations thereof. Examples include, but are not limited to, silver oxide, silver nitrate, silver acetate, silver lactate, silver sulfate, copper chloride, copper oxide, copper nitrate, copper acetate, copper lactate, copper sulfate, zinc chloride, zinc oxide, zinc nitrate, zinc acetate, zinc lactate, and zinc sulfate. In addition to antimicrobial properties, some of these materials also possess antifungal properties that may provide additional relief to the wearer. The antimicrobial material could, for example, be molded or bonded to the adhesive pad and/or the sensor electronics unit housing. Brass components could also double as temperature transfer points to measure skin surface temperature. In addition to the antimicrobial materials described above (e.g. silver, copper, and zinc compounds), an antimicrobial agent can be incorporated into the adhesive pad. Examples include, but are not limited to, antimicrobial agents such as parachlorometaxylenol, chlorhexidine and salts thereof, iodine, and iodophores, and antibiotics such as neomycin, bacitracin, and polymyxin B.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An adhesive pad system for securing a continuous analyte sensor assembly to a skin surface of a host, the system comprising:
   a housing configured to receive a sensor electronics unit, the housing having an undersurface, the housing comprising one or more channels located in the undersurface, the one or more channels configured to promote flow of moisture present from the skin surface of the host;
   an adhesive pad comprising a nonwoven spunlace material and having an upper surface and an undersurface, the adhesive pad configured to secure the continuous analyte sensor assembly to the skin surface of the host, wherein the housing is secured to the upper surface of the adhesive pad by heatstaking, and wherein the undersurface of the adhesive pad includes an adhesive material configured to adhere the adhesive pad to the skin surface of the host;
   an overlay having an upper surface, an undersurface, and a central opening configured to allow at least a portion of the housing to protrude therefrom,
      wherein the undersurface of the overlay includes an adhesive material configured to adhere a first portion of the overlay to the adhesive pad and to adhere a second portion of the overlay to the skin surface of the host,
      wherein the overlay has a larger perimeter dimension than the adhesive pad, and
      wherein the overlay extends outwardly on all sides from a periphery of the adhesive pad when the overlay is positioned over the adhesive pad with the housing protruding through the central opening;

a first lower liner including a first peel tab, the first lower liner having an upper surface and an undersurface, wherein the upper surface of the first lower liner is configured to adhere to the first portion of the overlay; and a second lower liner including a second peel tab, the second lower liner having an upper surface and an undersurface, wherein the upper surface of the second lower liner is configured to adhere to the second portion of the overlay.

2. The system of claim 1, wherein the first portion of the overlay comprises from about 10% to about 65% of a total area of the overlay.

3. The system of claim 2, wherein the first portion of the overlay comprises from about 20% to about 55% of the total area of the overlay.

4. The system of claim 1, wherein the adhesive pad has an area from about 1 square inch to about 2 square inches.

5. The system of claim 4, wherein the overlay has an area from about 4 square inches to about 7 square inches.

6. The system of claim 1, wherein application of the overlay onto the adhesive pad results in an increased adhesive strength that is from about 40% to about 45% of the adhesive strength of the adhesive pad alone.

7. The system of claim 1, wherein the overlay is configured to be removed from the adhesive pad and from the skin surface of the host without disturbing continued operation of the sensor electronics unit.

8. The system of claim 1, wherein the one or more channels are located on an exterior of the undersurface.

9. A method for securing a continuous analyte sensor assembly to a skin surface of a host, the method comprising:
   securing the continuous analyte sensor assembly to the skin surface of the host,
      wherein the continuous analyte sensor assembly comprises a continuous analyte sensor, an adhesive pad, and a housing configured to receive a sensor electronics unit, the housing having an undersurface, the housing comprising one or more channels located in the undersurface, the one or more channels configured to promote flow of moisture present from the skin surface of the host,
      wherein the adhesive pad comprises an upper surface and an undersurface,
      wherein the housing is secured to the upper surface of the adhesive pad by heatstaking,
      wherein the undersurface of the adhesive pad includes an adhesive material configured to adhere the adhesive pad to the skin surface of the host, and
      wherein the adhesive pad comprises a nonwoven spunlace material;
   removing a first lower liner and a second lower liner from a reinforcing overlay; and
   applying the reinforcing overlay to the adhesive pad and to the skin surface,
      wherein the overlay includes an upper surface, an undersurface, and a central opening configured to allow at least a portion of the housing to protrude therefrom,
      wherein the undersurface of the overlay includes an adhesive material configured to adhere a first portion of the overlay to the adhesive pad and to adhere a second portion of the overlay to the skin surface of the host,
      wherein the overlay has a larger perimeter dimension than the adhesive pad,
      wherein the overlay extends outwardly on all sides from a periphery of the adhesive pad when the overlay is positioned over the adhesive pad with the housing protruding through the central opening,
      wherein the overlay, prior to the applying, comprises the first lower liner including a first peel tab, the first lower liner having an upper surface and an undersurface, wherein the upper surface of the first lower liner is configured to adhere to the first portion of the overlay, and
      wherein the overlay, prior to the applying, comprises a second lower liner including a second peel tab, the second lower liner having an upper surface and an undersurface, wherein the upper surface of the second lower liner is configured to adhere to the second portion of the overlay.

10. The method of claim 9, wherein the first portion of the overlay comprises from about 10% to about 65% of a total area of the overlay.

11. The method of claim 10, wherein the first portion of the overlay comprises from about 20% to about 55% of a total area of the overlay.

12. The method of claim 9, wherein the adhesive pad has an area from about 1 square inch to about 2 square inches.

13. The method of claim 12, wherein the overlay has an area from about 4 square inches to about 7 square inches.

* * * * *